US011951127B2

(12) United States Patent
Blyth et al.

(10) Patent No.: US 11,951,127 B2
(45) Date of Patent: Apr. 9, 2024

(54) ADOPTIVE T CELL THERAPY 2

(71) Applicants: THE WESTMEAD INSTITUTE FOR MEDICAL RESEARCH, New South Wales (AU); THE UNIVERSITY OF SYDNEY, New South Wales (AU); WESTERN SYDNEY LOCAL HEALTH DISTRICT, New South Wales (AU); NEW SOUTH WALES HEALTH PATHOLOGY, New South Wales (AU)

(72) Inventors: Emily Blyth, New South Wales (AU); Leighton Clancy, New South Wales (AU); David Gottlieb, New South Wales (AU); Kenneth Micklethwaite, New South Wales (AU)

(73) Assignees: THE WESTMEAD INSTITUTE FOR MEDICAL RESEARCH, New South Wales (AU); THE UNIVERSITY OF SYDNEY, New South Wales (AU); WESTERN SYDNEY LOCAL HEALTH DISTRICT, New South Wales (AU); NEW SOUTH WALES HEALTH PATHOLOGY, New South Wales (AU)

(*) Notice: Subject to any disclaimer, the term of this patent is extended or adjusted under 35 U.S.C. 154(b) by 762 days.

(21) Appl. No.: 16/625,443

(22) PCT Filed: Jun. 22, 2018

(86) PCT No.: PCT/AU2018/050630
§ 371 (c)(1),
(2) Date: Dec. 20, 2019

(87) PCT Pub. No.: WO2018/232467
PCT Pub. Date: Dec. 27, 2018

(65) Prior Publication Data
US 2022/0226373 A1 Jul. 21, 2022

(30) Foreign Application Priority Data
Jun. 22, 2017 (AU) .................... 2017902407

(51) Int. Cl.
A61K 35/17 (2015.01)
A61K 39/00 (2006.01)
A61K 39/12 (2006.01)
A61P 31/10 (2006.01)
A61P 31/12 (2006.01)
A61P 35/00 (2006.01)
A61P 39/00 (2006.01)

(52) U.S. Cl.
CPC .......... A61K 35/17 (2013.01); A61K 39/0002 (2013.01); A61K 39/001153 (2018.08); A61K 39/12 (2013.01); A61P 31/10 (2018.01); A61P 31/12 (2018.01); A61P 35/00 (2018.01); A61K 2039/5158 (2013.01); A61K 2039/70 (2013.01)

(58) Field of Classification Search
None
See application file for complete search history.

(56) References Cited

FOREIGN PATENT DOCUMENTS

| EP | 3079715 A2 | 10/2016 |
|---|---|---|
| WO | 2006/060878 A1 | 6/2006 |
| WO | 2009/053109 A1 | 4/2009 |
| WO | 2015/086590 A2 | 6/2015 |
| WO | 2017/004678 A1 | 1/2017 |
| WO | 2018/232467 A1 | 12/2018 |

OTHER PUBLICATIONS

International Search Report and Written Opinion, dated Oct. 5, 2018, for International Application No. PCT/AU2018/050630.
Deo et al., Stimulation with lysates of Aspergillus terreus, Candida krusei and Rhizopus oryzae maximizes cross-reactivity of antifungal T cells. Cytotherapy, vol. 18, pp. 65-79 (2016).
Blyth et al., Cytotoxic T cells specific for Adenovirus, BK Virus, Cytomegalovirus, Epstein Barr Virus and Varicella Zoster Virus produced for clinical use in immune reconstitution post allogeneic stem cell transplantation. Blood, vol. 116(21), Abstract 830 (2010).
Ma et al., Addition of Varicella Zoster Virus-specific T cells to Cytomegalovirus, Epstein-Barr virus and Adenovirus tri-specific T cells as adoptive immunotherapy in patients undergoing allogeneic hematopoietic stem cell transplantation. Cytotherapy, vol. 17, pp. 1406-1420 (2015).
Wang et al., Adoptive transfer of tumor-primed, in vitro-activated, CD4+ T effector cells (TES) combined with CD8+ TES provides intratumoral TE proliferation and synergistic antitumor response. Blood, vol. 109, No. 11, pp. 4865-4876 (2007).
Zandvliet et al., Simultaneous isolation of CD8+ and CD4+ T cells specific for multiple viruses for broad antiviral immune reconstitution after allogeneic stem cell transplantation. Journal of Immunotherapy, vol. 34, No. 3, pp. 307-319 (2011).
Supplementary European Search Report, dated Mar. 23, 2021, for European Patent Application No. 18820696 (search completed on Mar. 11, 2021).

(Continued)

Primary Examiner — Oluwatosin A Ogunbiyi

(74) Attorney, Agent, or Firm — Gary J. Gershik

(57) ABSTRACT

The present disclosure relates to compositions comprising isolated T cells, with activity against a fungal antigen, a viral antigen or a tumour antigen, wherein the composition comprises a defined number or defined ratio of T cells. Described herein are compositions comprising at least two populations of T cells, the compositions being suitable for treating various diseases and disorders.

22 Claims, 23 Drawing Sheets

(56) References Cited

OTHER PUBLICATIONS

Gjertsen et al., Intradermal ras peptide vaccination with granulocyte-macrophage colony stimulating factor as adjuvant: Clinical and immunological responses in patients with pancreatic adenocarcinoma. International Journal of Cancer, vol. 92, No. 3, pp. 441-450 (2001).
Hunger et al., Successful induction of immune responses against mutant ras in melanoma patients using intradermal injection of peptides and GM-CSF as adjuvant. Experimental Dermatology, vol. 10, No. 3, pp. 161-167 (2001).
Weden et al., Long-term follow-up of patients with resected pancreatic cancer following vaccination against mutant K-ras. International Journal of Cancer, vol. 128, No. 5, pp. 1120-1128 (2010).
Prior et al., A comprehensive survey of Ras mutations in cancer. Cancer Research, vol. 72, No. 10, pp. 2457-2467 (2012).

E

F

ADOPTIVE T CELL THERAPY 2

FIELD

The present disclosure relates to T cell products with activity against a fungal antigen, a viral antigen or a tumour antigen, wherein the product comprises a defined number or defined ratio of T cells.

BACKGROUND

Invasive pathogenic infections are significant causes of morbidity and mortality, particularly in patients undergoing haematological stem cell transplantation who are increasingly susceptible to infection.

Amongst the most common infections seen during treatment for haematological malignancy are those caused by viral and/or fungal pathogens. Despite the introduction of better diagnostic tools and new antifungal and antiviral drugs, clinical outcomes remain poor. Drug resistance is a particular problem in the treatment of both fungal and viral infections. Multiple fungal species have demonstrated resistance to Amphotericin B and newer azole and echinocandins. Toxicity including myelosuppression and nephrotoxicity frequently prevents prolonged administration of antiviral drugs. Antifungal and antiviral antibiotic treatment does not correct the immunosuppression that has led to the opportunistic infection in the first place.

T cells belong to a group of white blood cells known as lymphocytes, and play a central role in cell-mediated immunity and, to a lesser degree the adaptive immune response. Generally, T cells are distinguished from other lymphocytes (e.g., B cells and natural killer cells) by the presence of T cell receptors (TCRs). T cells have diverse roles, which are accomplished by differentiation of distinct populations of T cells, recognizable by discrete gene expression profiles and phenotypes. Exemplary T cell populations include naïve T cells, T helper cells ($T_H$ cells), terminally differentiated effector T cells ($T_{eff}$ cells), effector memory T cells ($T_{em}$ cells), central memory T cells ($T_{cm}$ cells), stem cell memory cells (Tscm), cytotoxic T cells (CTLs) and regulatory T cells (Treg cells).

Fungus, viral and tumour-specific T cell production is fundamental to the body's defence against invasive diseases, and defective in vitro T cell immunity has been shown to correlate with the period when patients are at highest risk of infection.

Adoptive immunotherapy by providing T cells specific for the fungal infection has been shown. However, defined T cell compositions to fungal, viral and/or tumour antigens have not been described.

It will be clear to the skilled person from the foregoing, that there is a need in the art for restoration of effective adaptive antifungal, antiviral and/or antitumoural immunity.

SUMMARY

The present disclosure is based on the inventors' identification of a defined T cell product with specificity against a fungal, viral or tumour pathogen.

The inventors isolated T cells from peripheral blood and hematopoietic stem cells mobilized with G-CSF and expanded pathogen (i.e., fungal, viral or tumour) specific T cells using fungal antigens from fungal extracts, viral antigens from viruses or tumour antigens. Using these T cells, the inventors prepared compositions comprising a defined number or defined ratio of at least two populations of T cells where each population of T cells is reactive with a fungal antigen, a viral antigen or a tumour antigen. Previous multipathogen T cell compositions were undefined in their content of T cells specific for each pathogen and, as a consequence, of unknown specificity. By preparing compositions based on defined T cell populations, the inventors of the present disclosure proceeded against this conventional wisdom, and as such prepared compositions with broader protection.

The present disclosure is broadly directed to a composition comprising at least two populations of T cells each population reactive with a fungal antigen, a viral antigen or a tumour antigen, and wherein the composition comprises a defined number or defined ratio of T cells in each population.

In one example, the T cells are isolated from a sample from a subject, e.g. a blood sample or fraction thereof (e.g., buffy coat fraction or peripheral blood mononuclear cell fraction) or a thymus or part thereof. Accordingly, the present disclosure also encompasses a method additionally comprising providing or obtaining a sample from a subject. Such a sample may have been isolated previously from a subject, e.g., the method is performed in vitro or ex vivo. The population of cells can also be an isolated population of cells, e.g., produced using tissue culture techniques.

In one example, each population of T cells are expanded, e.g., in vitro or ex vivo. For example, the isolated cells are culture expanded.

As will be apparent to the skilled artisan, the isolated and/or expanded cell population of the present disclosure is not necessarily the same as naturally-occurring T cell populations. This is because the T cells in the population are expanded against a fungal, a viral or a tumour antigen and multiple T cell populations are combined in a way which does not necessarily occur in nature. Moreover, each population of T cells are expanded against individual antigens and the composition prepared from a combination of at least two T cell populations that may not occur in a subject at the same time. Furthermore, each population of T cells are expanded against individual antigens (i.e., a subset of infective organisms) as opposed to all antigens that may occur in a subject at the same time.

In one example, the fungal antigen is in the form of a fungal extract.

In one example, the fungal extract is a water soluble fungal lysate. In one example, the water soluble lysate is formed from cellular extracts. For example, the water soluble lysate is formed from lysed fungal spores. In one example, the water soluble lysates are produced by lysing germinated spores of the fungus in water and obtaining the lysate. For example, the water soluble lysates are obtained by homogenizing germinated spores of the fungus in water and obtaining the lysate.

In one example, the viral antigen is in the form of overlapping peptides from viral proteins or a lysate of virally infected cells. For example, the viral antigen is a viral protein or a peptide or peptides from a viral protein or is within a lysate of a virus infected cell or is expressed by a cell modified to express the viral antigen.

In one example, the tumour antigen is in the form of overlapping peptides from tumour proteins. For example, the tumour antigen is a tumour protein or a peptide or peptides from a tumour protein or is expressed by a cell modified to express the tumour antigen.

Exemplary T cell populations include naïve T cells, T helper cells ($T_H$ cells), terminally differentiated effector T cells ($T_{eff}$ cells), effector memory T cells ($T_{em}$ cells), central memory T cells ($T_{cm}$ cells), cytotoxic T cells (CTLs) and regulatory T cells (Treg cells).

The present disclosure provides a composition comprising at least two populations of T cells. For example, the composition comprises two populations of T cells, or three populations of T cells, or four populations of T cells, or five populations of T cells, or six populations of T cells, or seven populations of T cells, or eight populations of T cells, or nine populations of T cells, or ten populations of T cells, or eleven populations of T cells, or twelve populations of T cells, or thirteen populations of T cells, or fourteen populations of T cells, or fifteen populations of T cells, or sixteen populations of T cells, or seventeen populations of T cells, or eighteen populations of T cells, or nineteen populations of T cells, or twenty populations of T cells. In one example, the composition comprises four populations of T cells.

The present disclosure provides a composition comprising at least two T cell populations wherein each population comprises a defined number or defined ratio of T cells. In one example, the defined number or defined ratio of T cells in each population is based on a) the total number of nucleated cells; b) the number of CD3+ cells, or CD4+ cells, or CD8+ cells; c) the number of activation marker positive cells; and/or the number of cytokine producing cells on re-stimulation.

In one example, the defined number or defined ratio of T cells in each population is based on the total number of nucleated cells.

In one example, the defined number or defined ratio of T cells in each population is based on the number of CD3+ cells, or CD4+ cells, or CD8+ cells.

In one example, the defined number or defined ratio of T cells in each population is based on the number of activation marker positive cells.

In one example, the composition comprises an equal number of T cells in each population.

In one example, the composition comprises at least two populations of T cells, wherein each population is combined in a ratio of between about 1:1 and about 1:99. For example, each population of T cells is combined in a ratio of about 1:1, or about 1:2, or about 1:3, or about 1:4, or about 1:5, or about 1:6, or about 1:7, or about 1:8, or about 1:9, or about 1:10. In one example, each population of T cells is combined in a ratio of about 1:10, or about 1:15, or about 1:20, or about 1:25, or about 1:30, or about 1:35, or about 1:40, or about 1:45, or about 1:50, or about 1:55, or about 1:60, or about 1:65, or about 1:70, or about 1:75, or about 1:80, or about 1:85, or about 1:90, or about 1:95, or about 1:99.

In one example, the defined number or defined ratio is based on a subject's clinical diagnosis.

In one example, the defined number or defined ratio is based on a subject's serology or infectious status.

In one example, the defined number or defined ratio is based on a subject's previous serology or infectious status. For example, the defined number or defined ratio is based on a known profile for an infection.

In one example, the composition comprises a total of between about $1 \times 10^7$ cells/m$^2$ and about $10 \times 10^7$ cells/m$^2$. For example, the composition comprises a total of about $1 \times 10^7$ cells/m$^2$, or about $1.5 \times 10^7$ cells/m$^2$, or about $2 \times 10^7$ cells/m$^2$, or about $2.5 \times 10^7$ cells/m$^2$, or about $3 \times 10^7$ cells/m$^2$, or about $3.5 \times 10^7$ cells/m$^2$, or about $4 \times 10^7$ cells/m$^2$, or about $4.5 \times 10^7$ cells/m$^2$, or about $5 \times 10^7$ cells/m$^2$, or about $5.5 \times 10^7$ cells/m$^2$, or about $6 \times 10^7$ cells/m$^2$, or about $6.5 \times 10^7$ cells/m$^2$, or about $7 \times 10^7$ cells/m$^2$, or about $7.5 \times 10^7$ cells/m$^2$, or about $8 \times 10^7$ cells/m$^2$, or about $8.5 \times 10^7$ cells/m$^2$, or about $9 \times 10^7$ cells/m$^2$, or about $9.5 \times 10^7$ cells/m$^2$, or about $10 \times 10^7$ cells/m$^2$. In one example, the composition comprises a total of about $4 \times 10^7$ cells/m$^2$.

In one example, each population of T cells in the composition comprises between about $1 \times 10^6$ cells/m$^2$ and about $10 \times 10^7$ cells/m$^2$ of total nucleated cells. In one example, each population of T cells in the composition comprises between about $1 \times 10^6$ cells/m$^2$ and about $10 \times 10^6$ cells/m$^2$ of total nucleated cells. For example, each population of T cells in the composition comprises a total of about $1 \times 10^6$ cells/m$^2$, or about $1.5 \times 10^6$ cells/m$^2$, or about $2 \times 10^6$ cells/m$^2$, or about $2.5 \times 10^6$ cells/m$^2$, or about $3 \times 10^6$ cells/m$^2$, or about $3.5 \times 10^6$ cells/m$^2$, or about $4 \times 10^6$ cells/m$^2$, or about $4.5 \times 10^6$ cells/m$^2$, or about $5 \times 10^6$ cells/m$^2$, or about $5.5 \times 10^6$ cells/m$^2$, or about $6 \times 10^6$ cells/m$^2$, or about $6.5 \times 10^6$ cells/m$^2$, or about $7 \times 10^6$ cells/m$^2$, or about $7.5 \times 10^6$ cells/m$^2$, or about $8 \times 10^6$ cells/m$^2$, or about $8.5 \times 10^6$ cells/m$^2$, or about $9 \times 10^6$ cells/m$^2$, or about $9.5 \times 10^6$ cells/m$^2$, or about $10 \times 10^6$ cells/m$^2$ of total nucleated cells. In one example, the composition comprises a total of about $3.5 \times 10^6$ of total nucleated cells/m$^2$. In another example, each population of T cells in the composition comprises between about $1 \times 10^7$ cells/m$^2$ and about $10 \times 10^7$ cells/m$^2$ of total nucleated cells. For example, each population of T cells in the composition comprises a total of about $1 \times 10^7$ cells/m$^2$, or about $1.5 \times 10^7$ cells/m$^2$, or about $2 \times 10^7$ cells/m$^2$, or about $2.5 \times 10^7$ cells/m$^2$, or about $3 \times 10^7$ cells/m$^2$, or about $3.5 \times 10^7$ cells/m$^2$, or about $4 \times 10^7$ cells/m$^2$, or about $4.5 \times 10^7$ cells/m$^2$, or about $5 \times 10^7$ cells/m$^2$, or about $5.5 \times 10^7$ cells/m$^2$, or about $6 \times 10^7$ cells/m$^2$, or about $6.5 \times 10^7$ cells/m$^2$, or about $7 \times 10^7$ cells/m$^2$, or about $7.5 \times 10^7$ cells/m$^2$, or about $8 \times 10^7$ cells/m$^2$, or about $8.5 \times 10^7$ cells/m$^2$, or about $9 \times 10^7$ cells/m$^2$, or about $9.5 \times 10^7$ cells/m$^2$, or about $10 \times 10^7$ cells/m$^2$ of total nucleated cells.

In one example, the composition of the present disclosure comprises about 60-100% CD3+ cells, or about 70-100% CD3+ cells, or about 70-90% CD3+ cells. For example, the composition comprises about 70-80% CD3+ cells, such as about 70% CD3+ cells, or about 75% CD3+ cells, or about 80% CD3+ cells. For example, the composition comprises about 80-90% CD3+ cells, such as about 85% CD3+ cells, or about 90% CD3+ cells. For example, the composition comprises about 90-100% CD3+ cells, such as about 95% CD3+ cells, or about 100% CD3+ cells.

In one example, the percentage of CD3+ T cells is detected by flow cytometry analysis of cells expressing CD3.

In one example, the composition of the present disclosure comprises about 10-40% CD4+ cells, or about 10-20%, or about CD4+ cells, or about 20-30% CD4+ cells, or about 3-40% CD4+ cells, or about 50-100% CD4+ cells, or about 60-100% CD4+ cells, or about 60-90% CD4+ cells. For example, the composition comprises about 60-70% CD4+ cells, such as about 60% CD4+ cells, or about 65% CD4+ cells, or about 70% CD4+ cells. For example, the composition comprises about 70-80% CD4+ cells, such as about 75% CD4+ cells, or about 80% CD4+ cells. For example, the composition comprises about 80-90% CD4+ cells, such as about 85% CD4+ cells, or about 90% CD4+ cells. For example, the composition comprises about 90-100% CD4+ cells, such as about 95% CD4+ cells, or about 100% CD4+ cells.

In one example, the percentage of CD4+ T cells is detected by flow cytometry analysis for cells expressing CD4.

In one example, the composition of the present disclosure comprises about 10-40% CD8+ cells, or about 10-20%, or about CD8+ cells, or about 20-30% CD8+ cells, or about 3-40% CD8+ cells, or about 50-100% CD8+ cells, or about 60-100% CD8+ cells, or about 60-90% CD8+ cells. For example, the composition comprises about 60-70% CD8+ cells, such as about 60% CD8+ cells, or about 65% CD8+ cells, or about 70% CD8+ cells. For example, the composition comprises about 70-80% CD8+ cells, such as about 75% CD8+ cells, or about 80% CD8+ cells. For example, the composition comprises about 80-90% CD8+ cells, such as about 85% CD8+ cells, or about 90% CD8+ cells. For example, the composition comprises about 90-100% CD8+ cells, such as about 95% CD8+ cells, or about 100% CD8+ cells.

In one example, the percentage of CD8+ T cells is detected by flow cytometry analysis for cells expressing CD8.

The present disclosure provides a composition comprising at least two T cell populations each population reactive with a fungal antigen, a viral antigen or a tumour antigen. In one example, the composition comprises:
a) T cells reactive with fungal antigens only; or
b) T cells reactive with viral antigens only; or
c) T cells reactive with tumour antigens only; or
d) one or more population(s) of T cells each population reactive with a fungal antigen and one or more populations of T cells each population reactive with a viral antigen; or
e) one or more population(s) of T cells each population reactive with a fungal antigen and one or more population(s) of T cells each population reactive with a tumour antigen; or
f) one or more population(s) of T cells each population reactive with a viral antigen and one or more population(s) of T cells reactive with a tumour antigen; or
g) one or more population(s) of T cells each population reactive with a fungal antigen, one or more population of T cells each population reactive with a viral antigen and one or more population(s) of T cells each population reactive with a tumour antigen.

In one example, the composition comprises at least two T cell populations, wherein each population is reactive with a fungal antigen. For example, the composition does not comprise a population of T cells reactive with a viral or tumour antigen.

In one example, the composition comprises at least two T cell populations, wherein each population is reactive with a viral antigen. For example, the composition does not comprise a population of T cells reactive with a fungal antigen or a tumour antigen.

In one example, the composition comprises at least two T cell populations, wherein each population is reactive with a tumour antigen. For example, the composition does not comprise a population of T cells reactive with a fungal antigen or a viral antigen.

In one example, the composition comprises at least two T cell populations wherein at least one population of T cells is reactive with a fungal antigen and at least one population of T cells is reactive with a viral antigen. For example, the composition does not comprise a population of T cells reactive with a tumour antigen.

In one example, the composition comprises at least two T cell populations wherein at least one population of T cells is reactive with a fungal antigen and at least one population of T cells is reactive with a tumour antigen. For example, the composition does not comprise a population of T cells reactive with a viral antigen.

In one example, the composition comprises at least two T cell populations wherein at least one population of T cells is reactive with a viral antigen and at least one population of T cells is reactive with a tumour antigen. For example, the composition does not comprise a population of T cells reactive with a fungal antigen.

In one example, the composition comprises at least two T cell populations wherein at least one population of T cells is reactive with a fungal antigen, at least one population of T cells is reactive with a viral antigen and at least one population of T cells is reactive with a tumour antigen.

In one example, the composition comprises a population of T cells reactive with a fungal antigen from a fungal extract selected from the group consisting of *Aspergillus terreus, Candida krusei, Rhizopus oryzae, A. fumigatus, A. flavus, A. terreus, C. albicans, C. krusei, F. oxysporum, F. solani* and *L. prolificans*.

In one example, the composition comprises a population of T cells reactive with an extract of *C. krusei* and a population of T cells reactive with an extract of *A. terreus*.

In one example, the composition comprises a population of T cells reactive with an extract of *A. fumigatus*.

In one example, the composition comprises a population of T cells reactive with an extract of *C. krusei*.

In one example, the composition comprises a population of T cells reactive with an extract of *A. terreus*.

In one example, the composition comprises a population of T cells reactive with an extract of *R. oryzae*.

In one example, the composition comprises a population of T cells reactive with an extract of *A. flavus*.

In one example, the composition comprises a population of T cells reactive with an extract of *C. albicans*.

In one example, the composition comprises a population of T cells reactive with an extract of *F. oxysporum*.

In one example, the composition comprises a population of T cells reactive with an extract of *F. solani*.

In one example, the composition comprises a population of T cells reactive with an extract of *L. prolificans*.

In one example, the composition comprises a population of T cells reactive with a viral antigen from a virus selected from the group consisting of cytomegalovirus, Epstein-Barr virus, adenovirus, varicella zoster virus, influenza and BK virus, John Cunningham virus, respiratory syncytial virus, parainfluenzae, rhinovirus, human metapneumovirus, herpes simplex virus 1, herpes simplex virus II, human herpesvirus 6, human herpesvirus 8, hepatitis A virus, hepatitis B virus, hepatitis C virus, hepatitis E virus, rotavirus, papillomavirus, parvovirus and mixtures thereof.

In one example, the composition comprises a population of T cells reactive with cytomegalovirus, a population of T cells reactive with Epstein-Barr virus and a population of T cells reactive with adenovirus.

In one example, the composition comprises a population of T cells reactive with cytomegalovirus, a population of T cells reactive with Epstein-Barr virus, a population of T cells reactive with adenovirus and a population of T cells reactive with varicella zoster virus.

In one example, the composition comprises a population of T cells reactive with cytomegalovirus or a viral antigen thereof. For example, the composition comprises a population of T cells reactive with CMV pp65.

In one example, the composition comprises a population of T cells reactive with Epstein-Barr virus or a viral antigen thereof. For example, the composition comprises a population of T cells reactive with EBV BZLF1, LMP2A and/or EBNA1.

In one example, the composition comprises a population of T cells reactive with adenovirus or a viral antigen thereof. For example, the composition comprises a population of T cells reactive with AdV hexon.

In one example, the composition comprises a population of T cells reactive with varicella zoster virus or a viral antigen thereof.

In one example, the composition comprises a population of T cells reactive with BK virus or a viral antigen thereof. For example, the composition comprises a population of T cells reactive with BKV VPT, VP2, STA and/or LTA.

In one example, the composition comprises a population of T cells reactive with the influenza virus or a viral antigen thereof.

In one example, the composition comprises a population of T cells reactive with the JC virus or a viral antigen thereof.

In one example, the composition comprises a population of T cells reactive with RSV or a viral antigen thereof.

In one example, the composition comprises a population of T cells reactive with the parainfluenzae virus or a viral antigen thereof.

In one example, the composition comprises a population of T cells reactive with the rhinovirus or a viral antigen thereof.

In one example, the composition comprises a population of T cells reactive with the human metapneumovirus or a viral antigen thereof.

In one example, the composition comprises a population of T cells reactive with HSV 1 or HSV II or a viral antigen thereof.

In one example, the composition comprises a population of T cells reactive with the HHV6 or HHV8 or a viral antigen thereof.

In one example, the composition comprises a population of T cells reactive with hepatitis A virus or hepatitis B virus or hepatitis C virus or hepatitis E virus or a viral antigen thereof.

In one example, the composition comprises a population of T cells reactive with the rotavirus or a viral antigen thereof.

In one example, the composition comprises a population of T cells reactive with a papillomavirus or a viral antigen thereof.

In one example, the composition comprises a population of T cells reactive with a parvovirus or a viral antigen thereof.

In one example, the present disclosure provides a composition comprising a population of T cells reactive with a tumour antigen selected from the group consisting of Wilms tumour antigen (WT1), beta chain of human chorionic gonadotropin (hCG beta) antigen, carcinoembryonic antigen (CEA), alphafetoprotein (AFP), CD19, CD20, CA-125, epithelial tumor antigen (ETA), abnormal products of ras, p53, glycosphingolipid GD2, prostatic acid phosphatase (PAP), preferentially expressed antigen in melanoma (PRAME), B melanoma antigen (BAGE), cancer-testis antigen (NY ESO-1), sarcoma antigen 1 (SAGE), helicase antigen (HAGE), cancer-germline antigen (GAGE), prostein (P501S), six-transmembrane epithelial antigen of the prostate (STEAP), Plu-1, human achaete-scute homolog-1 (hASH1), Cripto, Criptin, EGFRvIII antigen, Globo H antigen, GM2 antigen, GP100 antigen, HER2/neu antigen, KSA antigen, Le (y) antigen, Melanoma-associated antigen (MAGE), MUC1 antigen, MUC2 antigen, MUC3 antigen, MUC4 antigen, MUC5AC antigen, MUC5B antigen, MUC7 antigen, prostate specific antigen (PSA), PSCA antigen, early prostate cancer antigen (EPCA-2, prostate-specific membrane antigen (PSMA), Thompson-Friedenreich antigen (TF), Tn antigen, sTn antigen, tyrosinase-related protein 1 (TRP 1) antigen, tyrosinase-related protein 2 (TRP 2) antigen, tumor-specific immunoglobulin variable region and tyrosinase antigen.

In one example, the composition comprises a population of T cells reactive with an extract of *C. krusei* and a population of T cells reactive with an extract of *A. terreus*.

In one example, the composition comprises a population of T cells reactive with a Wilms tumour antigen (WT1).

In one example, the composition comprises a population of T cells reactive with an extract of *A. fumigatus*, a population of T cells reactive with cytomegalovirus, a population of T cells reactive with Epstein-Barr virus and a population of T cells reactive with adenovirus.

In one example, the composition comprises a population of T cells reactive with cytomegalovirus, a population of T cells reactive with Epstein-Barr virus, a population of T cells reactive with adenovirus and a population of T cells reactive with varicella zoster virus. In one example, the composition additionally comprises a population of T cells reactive with WT1.

In one example, administration of the composition of the present disclosure to a subject confers a therapeutic or protective immune response. For example, the composition confers an immune response against a fungal pathogen or a viral pathogen or a tumour antigen. In one example, the composition confers an immune response against a fungal pathogen. In another example, the composition confers an immune response against a viral pathogen. In a further example, the composition confers an immune response against a tumour antigen.

In one example, one of the at least two populations of T cells is enriched for CD137 expressing cells.

In one example, methods for producing a composition of the present disclosure are also provided.

In one example, the present disclosure provides a method for producing the composition described herein, comprising:
a) contacting a population of cells comprising T cells with a fungal antigen, a viral antigen or a tumour antigen;
b) repeating step a) for each population of cells in the composition;
c) isolating the populations comprising T cells following the contacting; and
d) combining the populations of T cells in a defined ratio or defined number.

In one example, the isolated populations comprise activated T cells. For example, the activated T cells are isolated using an activation marker. In one example, the activation marker is CD137. In one example, the activation marker is CD154.

In one example, the population of isolated cells comprising T cells is enriched for CD137 expressing cells.

In one example, each isolated CD137 enriched T cell population comprises about 10-40% CD4+ cells, or about 10-20%, or about CD4+ cells, or about 20-30% CD4+ cells, or about 3-40% CD4+ cells, or about 50-100% CD4+ cells, or about 60-100% CD4+ cells, or about 60-90% CD4+ cells. For example, each isolated CD137 enriched T cell population comprises about 60-70% CD4+ cells, such as about 60% CD4+ cells, or about 65% CD4+ cells, or about 70% CD4+ cells. For example, each isolated CD137 enriched T cell population comprises about 70-80% CD4+ cells, such as about 75% CD4+ cells, or about 80% CD4+ cells. For example, each isolated CD137 enriched T cell population comprises about 80-90% CD4+ cells, such as about 85% CD4+ cells, or about 90% CD4+ cells. For example, each isolated CD137 enriched T cell population comprises about 90-100% CD4+ cells, such as about 95% CD4+ cells, or about 100% CD4+ cells.

In one example, each isolated CD137 enriched T cell population comprises about 10-40% CD8+ cells, or about 10-20%, or about CD8+ cells, or about 20-30% CD8+ cells, or about 3-40% CD8+ cells, or about 50-100% CD8+ cells, or about 60-100% CD8+ cells, or about 60-90% CD8+ cells. For example, each isolated CD137 enriched T cell population comprises about 60-70% CD8+ cells, such as about 60% CD8+ cells, or about 65% CD8+ cells, or about 70% CD8+ cells. For example, each isolated CD137 enriched T cell population comprises about 70-80% CD8+ cells, such as about 75% CD8+ cells, or about 80% CD8+ cells. For example, each isolated CD137 enriched T cell population comprises about 80-90% CD8+ cells, such as about 85% CD8+ cells, or about 90% CD8+ cells. For example, each isolated CD137 enriched T cell population comprises about 90-100% CD8+ cells, such as about 95% CD8+ cells, or about 100% CD8+ cells.

In one example, the method comprises expanding the isolated populations comprising T cells in vitro. In one example, the isolated T cell populations are enriched for CD137 expressing cells prior to in vitro expansion. For example, the isolated populations comprising T cells are expanded in vitro prior to combining in a defined ratio or defined number. In one example, the method comprises expanding the population of cells comprising T cells in vitro prior to combining, for example, using one or more cytokines.

In one example, the method comprises contacting a population of cells comprising T cells with a fungal antigen, a viral antigen or a tumour antigen. In one example, the method comprises contacting each population of cells comprising T cells with a fungal antigen, a viral antigen or a tumour antigen. For example, the method of contacting is repeated for each population of T cells in the composition. In one example, the method comprises contacting the population(s) of cells comprising T cells with the fungal antigen, viral antigen or tumour antigen at least twice.

In one example, the method comprises isolating the populations comprising T cells following contacting with a fungal antigen, a viral antigen or a tumour antigen. Methods of isolating populations of T cells will be apparent to the skilled person, or are described herein.

In one example, the method comprises combining the populations (i.e., at least two populations) of T cells in a defined number or a defined ratio to produce the composition of the present disclosure.

In one example, the population(s) comprising T cells are populations of peripheral blood mononuclear cells or G-CSF mobilized hematopoietic stem cells or bone marrow cells.

In one example, the method of the present disclosure comprises:
a) contacting a first population of cells comprising T cells with an extract of *A. fumigatus*;
b) contacting a second population of cells comprising T cells with cytomegalovirus;
c) contacting a third population of cells comprising T cells with Epstein-Barr virus;
d) contacting a fourth population of cells comprising T cells with adenovirus;
e) isolating the populations comprising T cells following the contacting; and
f) combining the populations of T cells in a defined ratio or defined number.

In one example, the method of the present disclosure comprises:
a) contacting a first population of cells comprising T cells with an extract of *C. krusei*;
b) contacting a second population of cells comprising T cells with an extract of *A. terreus*;
c) isolating the populations comprising T cells following the contacting; and
d) combining the populations of T cells in a defined ratio or defined number.

In one example, the method of the present disclosure comprises:
a) contacting a first population of cells comprising T cells with cytomegalovirus;
b) contacting a second population of cells comprising T cells with Epstein-Barr virus;
c) contacting a third population of cells comprising T cells with adenovirus; and
d) contacting a fourth population of cells comprising T cells with varicella zoster virus;
e) isolating the populations comprising T cells following the contacting; and
f) combining the populations of T cells in a defined ratio or defined number.

In one example, the method additionally comprises formulating the population(s) of T cells into a pharmaceutically acceptable carrier.

In one example, the present disclosure comprises a composition produced by the methods described herein.

In one example, the present disclosure provides a method of treating a subject in need thereof, the method comprising administering the composition of the present disclosure or the population of cells comprising T cells produced by the method of the present disclosure.

For example, the method comprises administering an effective amount of the composition of the present disclosure or the population of cells comprising T cells produced by the method of the present disclosure, such as a therapeutically effective amount of the composition of the present disclosure or the population of cells comprising T cells produced by the method of the present disclosure.

In one example, the subject is undergoing or is about to commence or has completed chemotherapy and/or hematopoietic stem cell transplantation and/or immunoablation therapy and/or solid organ transplantation and/or has an inherited familial or congenital immunodeficiency syndrome and/or has an acquired immunodeficiency syndrome and/or is receiving or has received immunosuppressive therapy for an immune mediated disease.

In one example, the subject has completed chemotherapy, e.g., a subject who has received chemotherapy for a blood cancer, such as lymphoma or leukemia.

In one example, the subject has completed hematopoietic stem cell transplantation.

In one example, the subject is receiving immunosuppressive therapy following solid organ transplantation.

In one example, the subject is about to receive or has received a solid organ transplantation, e.g., transplantation of kidney, liver, pancreas, pancreatic islets, heart, lung, small bowel or other solid organ. In one example, the subject is receiving or has received immunosuppressive therapy, antibody treatment or soluble receptor treatment or another immunomodulating treatment for an immune mediated disease, e.g., inflammatory bowel disease, rheumatoid arthritis, multiple sclerosis, hepatitis, glomerulonephritis and kidney failure, cancer, lymphoma, leukemia, myelodysplasia, myeloma.

In one example, the subject is suffering from a disease or condition.

In one example, the subject suffers from an inherited familial or congenital immunodeficiency, e.g., severe combined immune deficiency, common variable immunodeficiency, alymphocytosis, Wiskott Aldrich syndrome, ataxia telangiectasia, di George syndrome, leucocyte adhesion defects, immunoglobulin deficiency. In one example, the subject has acquired immunodeficiency through infection with the human immunodeficiency virus or another pathogenic organism that has led to incompetence of the immune system or is suffering from chronic relapsing fungal infections, e.g., chronic or relapsing oral or vaginal fungal infections such as candidiasis, chronic or relapsing fungal skin infection, chronic or relapsing fungal nail infections, chronic or relapsing fungal bronchial infections, chronic or relapsing fungal sinus infections, chronic or relapsing fungal myocardial infections, chronic or relapsing fungal cerebral infections, chronic or relapsing fungal bone infections, chronic or relapsing fungal liver infections, chronic or relapsing fungal kidney or bladder infection.

In one example, the subject suffers from a cancer, such as a blood or bone marrow cancer, for example the cancer includes multiple myeloma, leukemia, lymphoma, neuroblastoma, Ewing sarcoma, myelodysplastic syndromes and gliomas. In another example, the disease or condition is a non-malignant condition, for example thalassemia, aplastic anemia, fanconi anemia and immune deficiency syndromes. In a further example, the condition or disease is associated with infection or graft-versus host disease.

In one example, the method comprises obtaining the cells from a subject and administering the composition to the same subject. For example, the T cells are autologous to the subject.

In one example, the method comprises obtaining cells from a fully HLA matched donor (i.e., a donor who has the same HLA antigens as the subject) and administering the composition to the subject. In one example, the donor is a stem cell donor. For example, the cells are allogeneic, e.g., HLA-matched allogeneic cells.

In one example, the method comprises obtaining cells from a partially HLA matched donor (i.e., a donor who has one or more HLA antigens the same as the subject) and administering the composition to the subject. In one example, the donor is a stem cell donor. For example, the cells are allogeneic, e.g., partially HLA-matched allogeneic cells. For example, the HLA antigen is HLA-A, HLA-B, HLA-C, HLA-DQ or HLA-DR. In one example, the HLA antigen is HLA-DR.

In one example, the method comprises matching at least one HLA antigen in the cells to at least one HLA antigen in the subject and administering the composition to the subject. For example, the matching HLA antigen is the antigen presenting an infection or tumour antigen to the T cells in the subject. In one example, the HLA antigen is the same for each population of cells in the composition. In one example, the HLA antigen is different for different infection and tumor specificities. For example, the HLA antigen in each population of T cells in the final composition matches different HLA antigens in the subject depending on the infection and tumor specificity. For example, the shared HLA antigen is an HLA-DR antigen, or an HLA-A antigen, or an HLA-B antigen, or an HLA-C antigen, or an HLA-DP antigen, or an HLA-DQ antigen, or combinations thereof.

In one example, the T cells are non-autologous or allogeneic to the subject.

In one example, the term "obtaining cells" from a donor encompasses obtaining the cells from a bank of donor cells. For example, the cells are obtained from a cryopreserved bank of donor cells. For example, HLA-matched allogeneic cells or partially HLA-matched allogeneic cells are obtained from the bank and administered to the subject.

In one example, the banked cells are selected for a stem cell transplant recipient with an invasive fungal infection. For example, banked cells are obtained from a third party donor, stimulated with one or more fungal extracts, CD137 selected and culture expanded with one or more cytokines. In one example, at least one HLA-allele in the banked cells is matched to a HLA-DR allele in the stem cell transplant recipient (i.e., subject) to which the composition is administered.

In one example, the method comprises isolating T cells from multiple donors (e.g., healthy donors), identifying at least one HLA antigen in the T cells, producing a composition according to the present disclosure and banking the composition for future use. For example, the HLA antigen in the T cells matches the antigen presenting the infection or tumour antigen to the T cells in the subject.

In one example, the method further comprises matching at least one HLA antigen in the banked composition with at least one HLA antigen (i.e., the HLA antigen presenting an infection or tumor antigen) in the subject and administering the composition to the subject. For example, the HLA antigen is an HLA-DR antigen, or an HLA-A antigen, or an HLA-B antigen, or an HLA-C antigen, or an HLA-DP antigen, or an HLA-DQ antigen.

In one example, the present disclosure provides a bank comprising a plurality of compositions of the present disclosure. For example, at least one of the HLA antigens in the T cells in each composition in the bank has been identified. In one example, the HLA is an HLA-DR antigen, or an HLA-A antigen, or an HLA-B antigen, or an HLA-C antigen, or a HLA-DP antigen, or an HLA-DQ antigen.

In one example, the present disclosure provides a method of treating a subject in need thereof, the method comprising determining an HLA antigen in the subject, matching the HLA antigen to an HLA antigen in T cells in a composition in the bank of the present disclosure and administering to the subject a composition comprising T cells having the same HLA antigen as that in the subject. In one example, the HLA antigen of the T cell in the composition is the same as the HLA antigen presenting an infection or tumour antigen in the subject. In one example, the HLA antigen of the T cell in the composition is the same as the HLA antigen presenting an infection or tumour antigen in the subject. In one example, the HLA antigen of the T cell in the composition is the same as the HLA antigen present an infection or tumour antigen in the subject but is a different allelic subtype of the HLA antigen.

Figure 2:
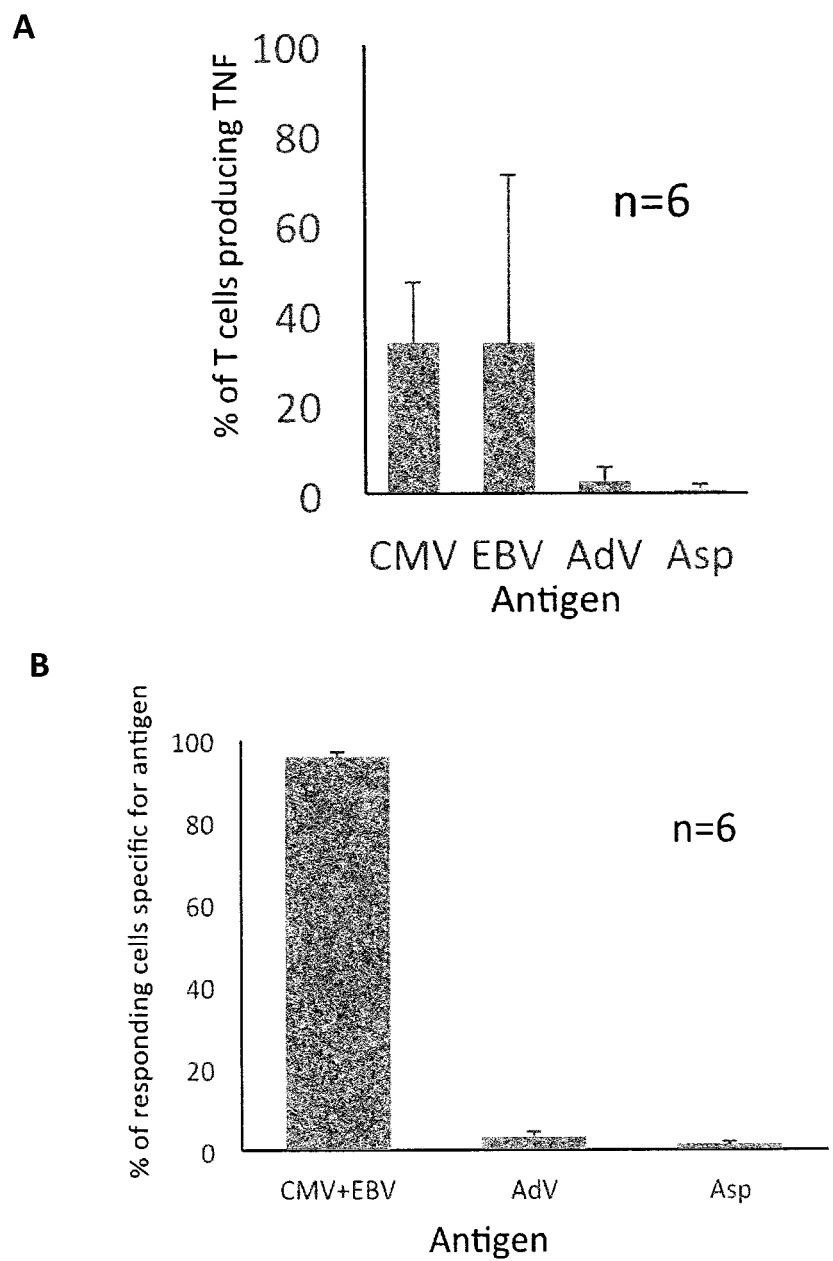
Figure 2:
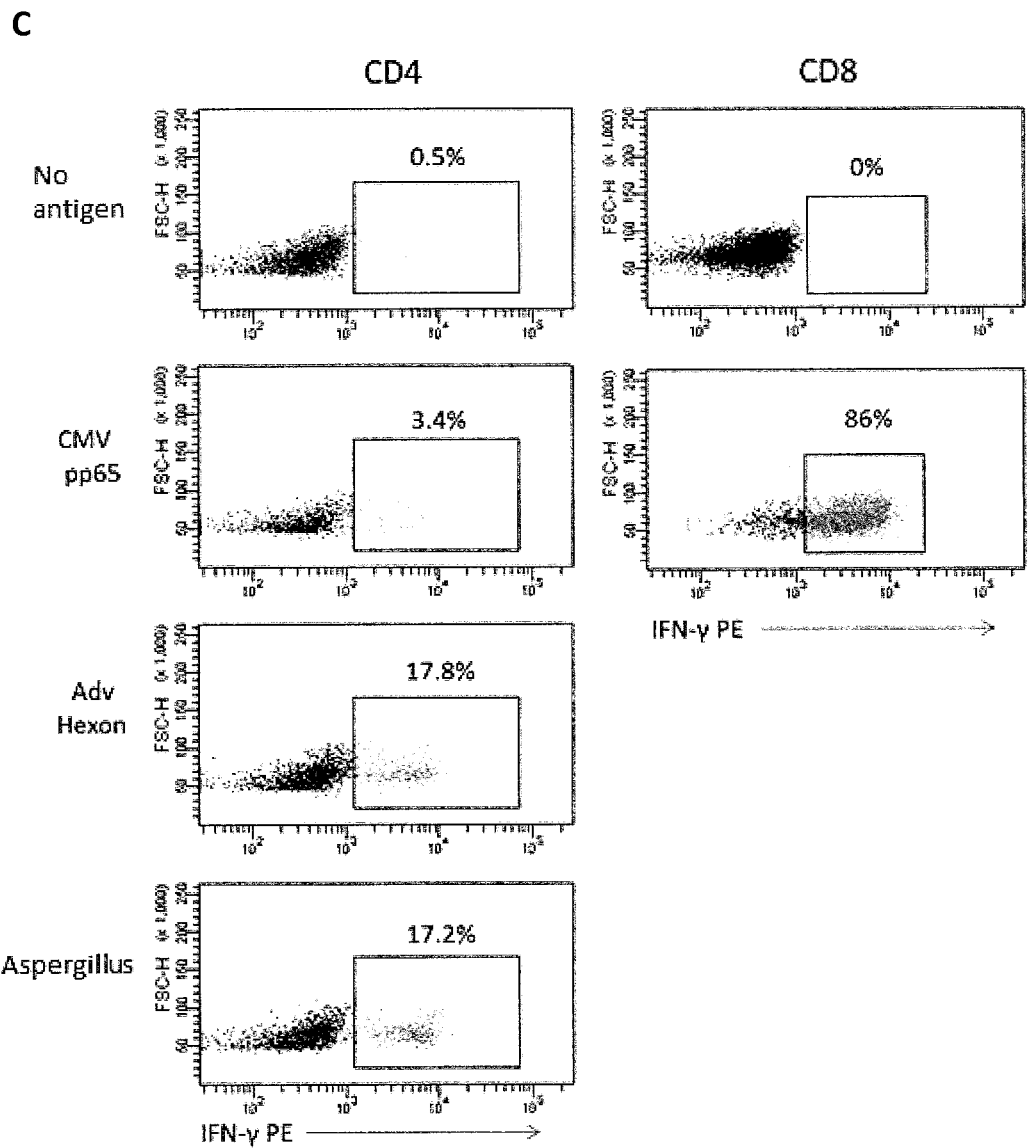

FIG. 2 is a graphical characterisation of multipathogen T cell cultures initiated with simultaneous stimulation of cultures with antigens from CMV, EBV, Adenovirus and *A fumigatus* lysate. A. Percentage of CD4$^+$ cells producing TNFα in response to re-stimulation with individual viral or fungal antigens. Bars indicate mean±SD (n=6). B. Proportion of TNFα producing T cells specific for either CMV and/or EBV compared to AdV and *A. fumigatus*. Bars indicate mean±SD (n=6). C. Proportion of IFNγ producing CD4$^+$ or CD8$^+$ T cells specific for CMV, AdV or *A. fumigatus*.

Figure 3:
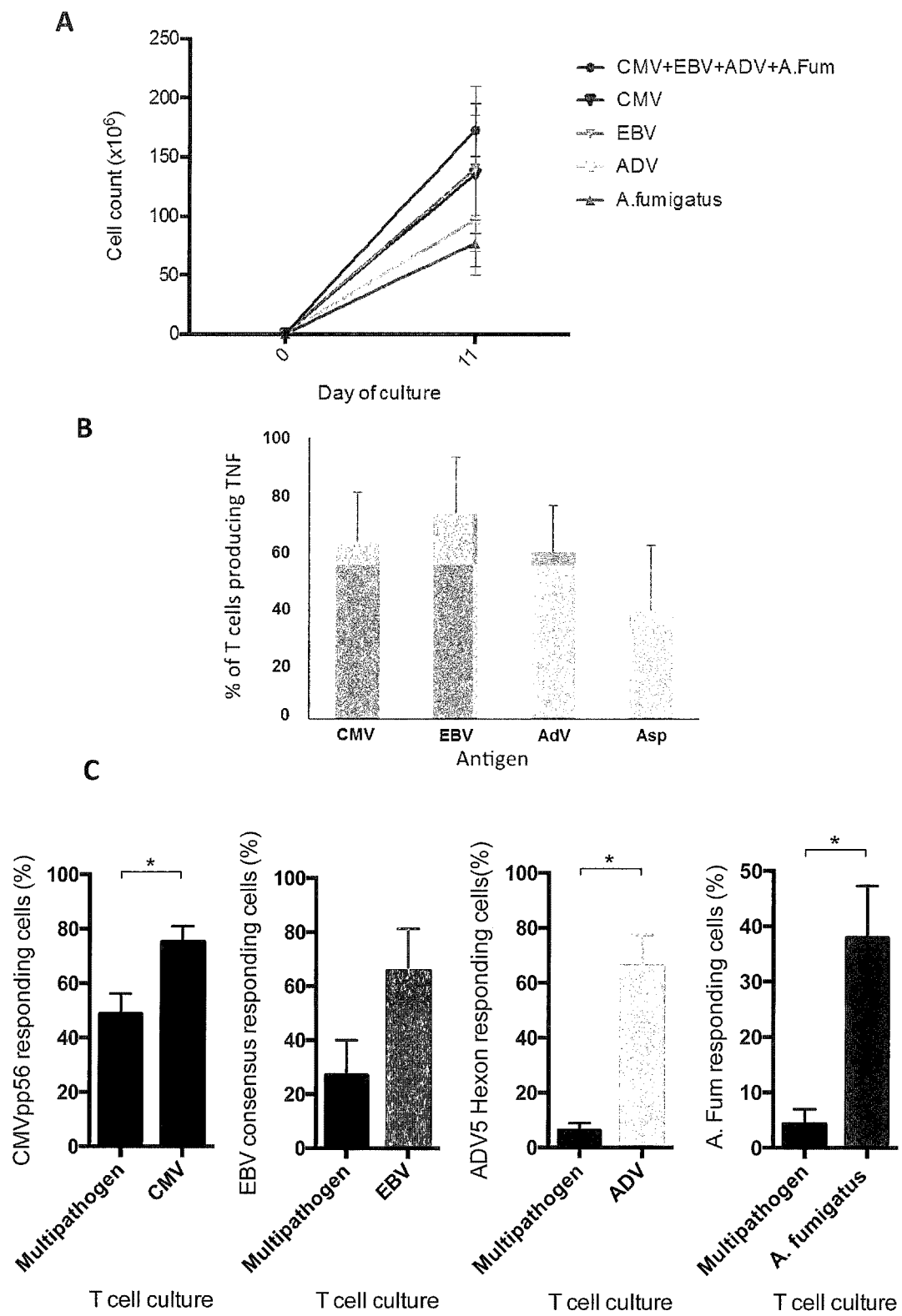

FIG. 3 is a graphical characterisation of individual viral and fungal T cell cultures. A. Expansion of T cell cultures stimulated with individual fungal or viral antigens followed by CD137 selection and expansion. Data expressed as mean cell number ±SEM. B. Percentage of T cells producing TNFα in response to re-stimulation with individual viral or fungal antigens following individual viral or fungal stimulation, CD137 selection and expansion and rechallenge with originating antigen. Bars indicate mean±SD (n=4-8). C. Percentage of responding cells in cultures stimulated with multiple antigens or with individual antigens prior to CD137 selection and expansion and subsequently rechallenged with CMV, EBV, ADV and *A. fumigatus*. Data expressed as mean±SEM (n=3-9) *p<0.05 (multipathogen versus individual peptide/protein lysate; Student's t-test).

Figure 4:
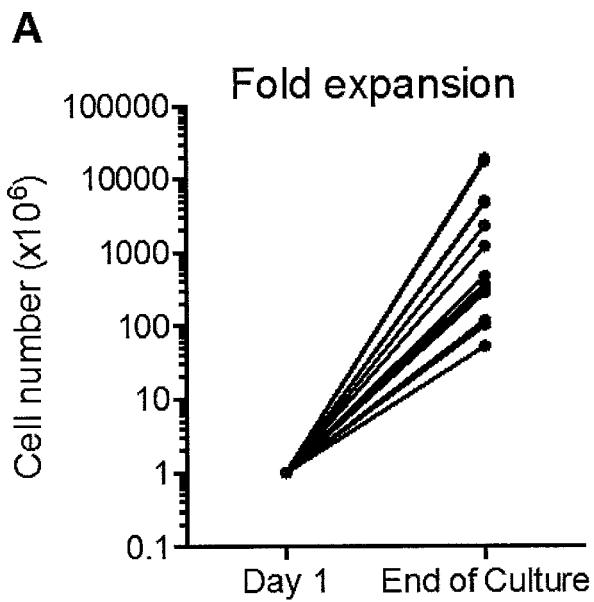
Figure 4:
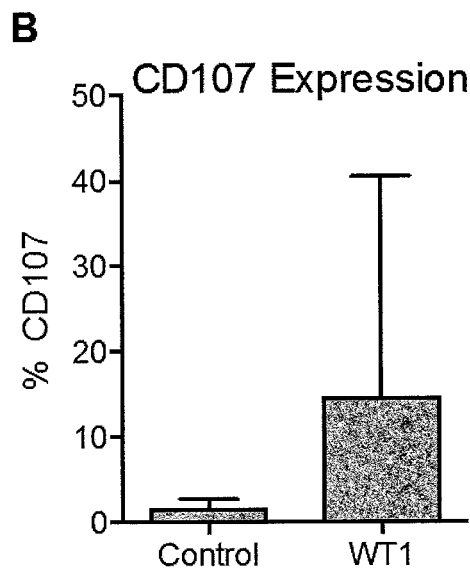
Figure 4:
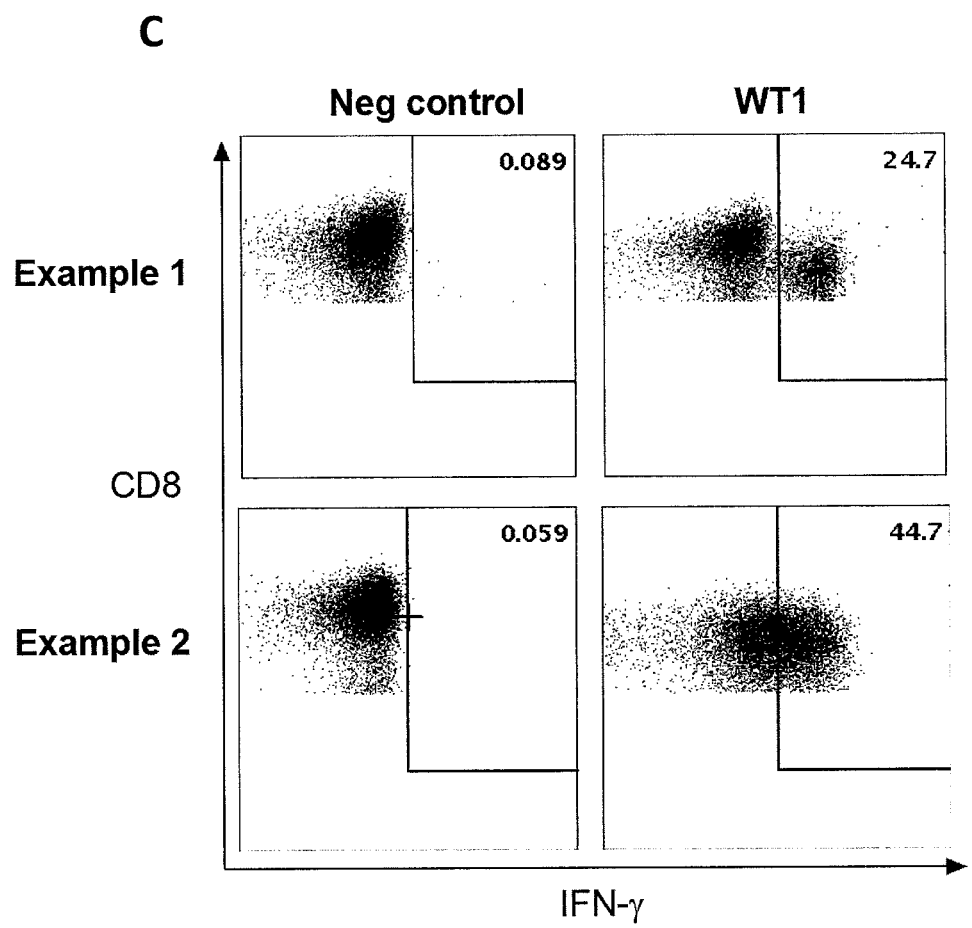

FIG. 4 is a graphical characterisation of WT1 T cell cultures A. Expansion of T cell cultures stimulated with WT1 antigen followed by CD137 selection and expansion. (n=14). B. WT1 specificity as measured by CD107 expression after re-stimulation of cultures generated in A and restimulated with WT1 peptide mixture. Data expressed as mean±SEM; p<0.05). C. Proportion of IFN-γ CD8 T cells specific for WT1.

Figure 5:
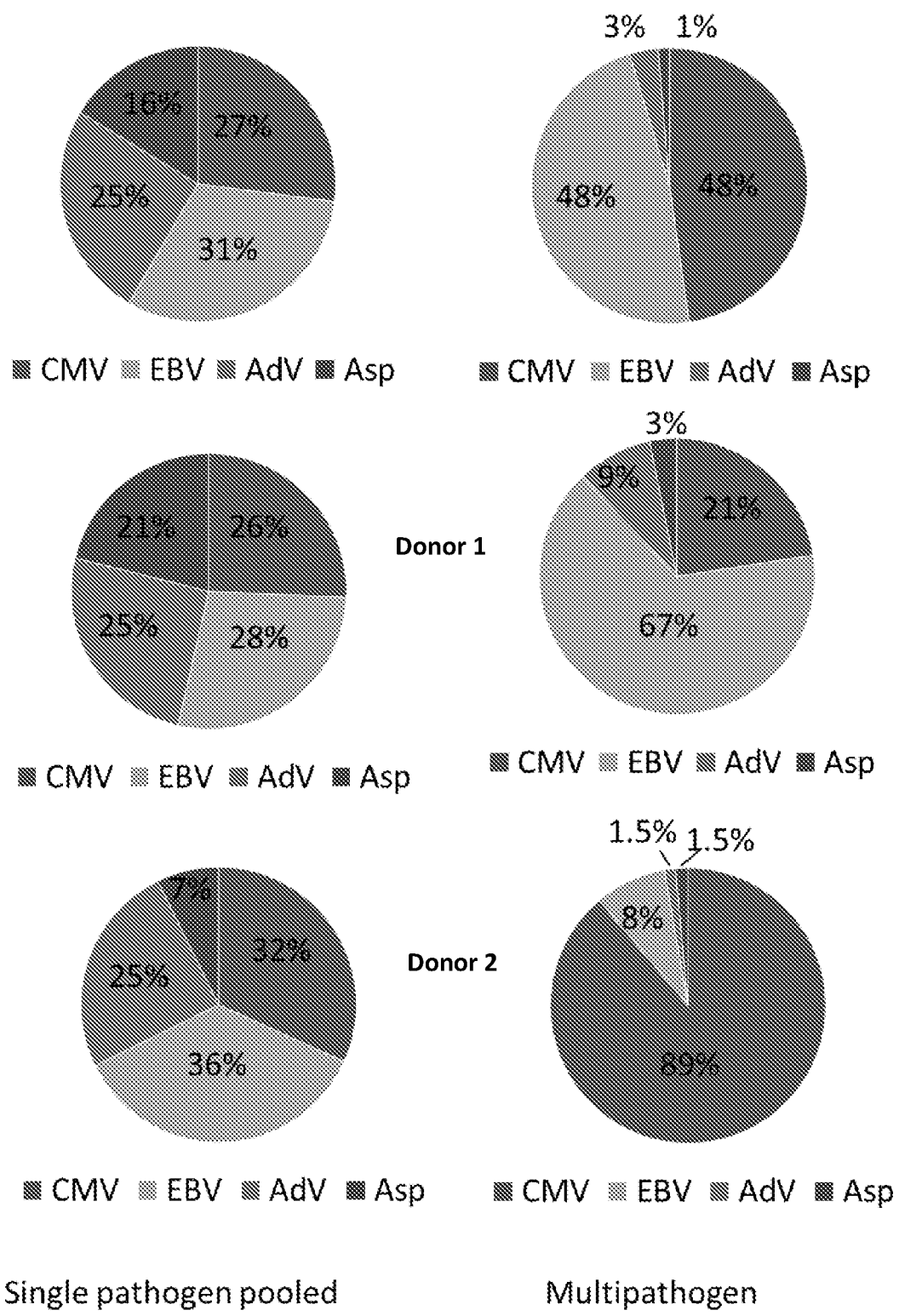

FIG. 5 is a graphical characterisation of T cell products generated from single T cell cultures pooled in defined ratios compared to cultures initiated with simultaneous stimulation with antigens from multiple pathogens. Percentages show responding cells from cultures following rechallenge with individual antigens.

Figure 6:
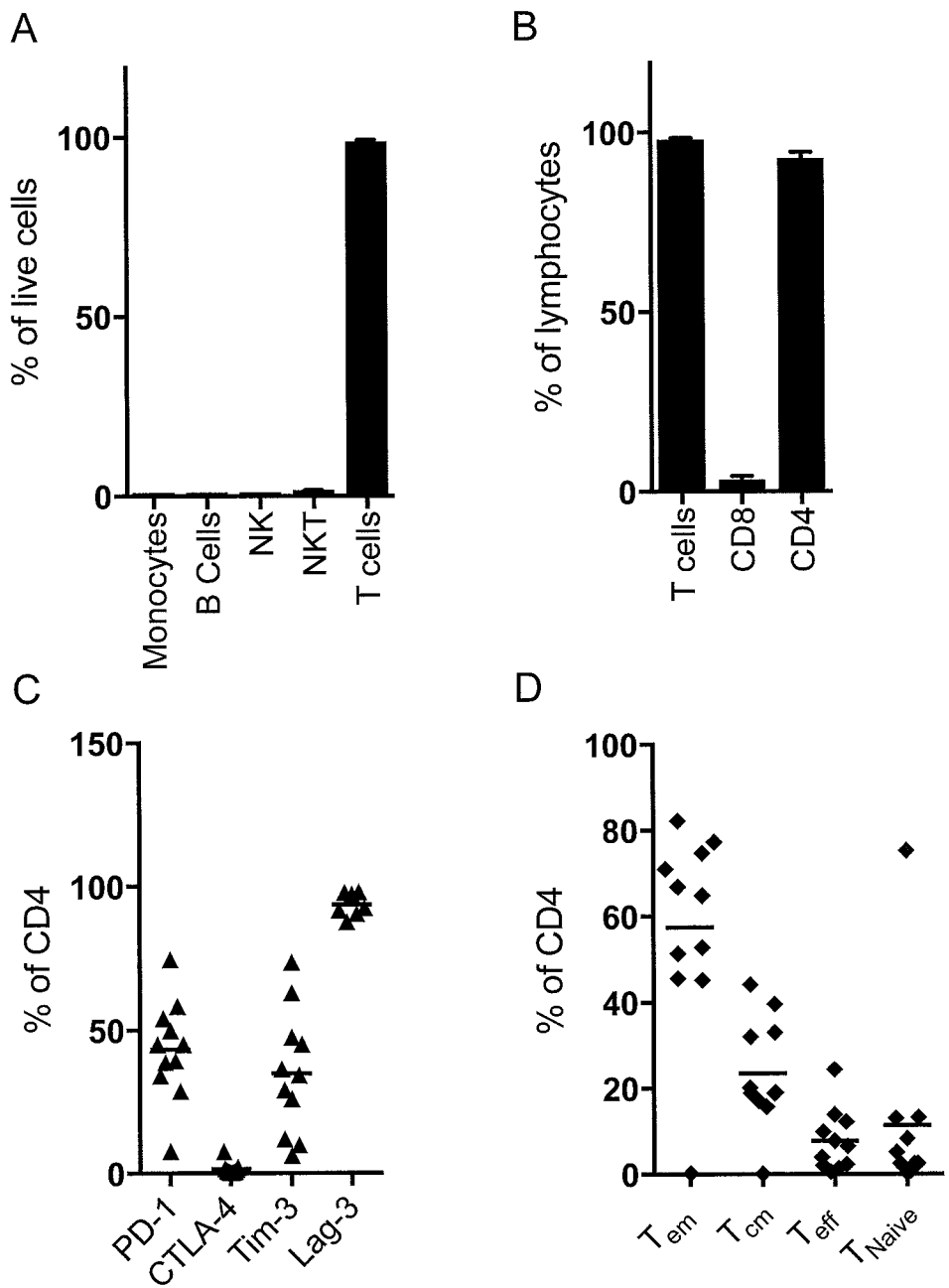

FIG. 6 is a graphical characterisation of multipathogen T cell cultures initiated by simultaneous stimulation with antigens from *A. terreus* and *C. krusei*, followed by CD137 selection and in vitro expansion. A. Percentage of T cells (CD3+) NK (CD3$^-$ CD56$^+$), NKT (CD3$^+$CD56$^+$), B cells (CD19$^+$) and monocytes (CD14$^+$). B. Percentage of CD4 T cells and CD8 T cells. C. Exhaustion markers expression profile (PD-1, Tim-3, CTLA-4 and Lag-3). D. T central memory (CD45RA$^-$62L$^+$), T terminal effector (CD45RA$^+$ 62L$^-$), T Naive (CD45RA$^+$62L$^+$) and T effector memory (CD45RA$^-$ 62L$^-$) at the end of culture. Results are means of 3 to 6 experiments (±s.e.m) and shown as percent of live cells, lymphocytes or CD4 T cells.

Figure 7:
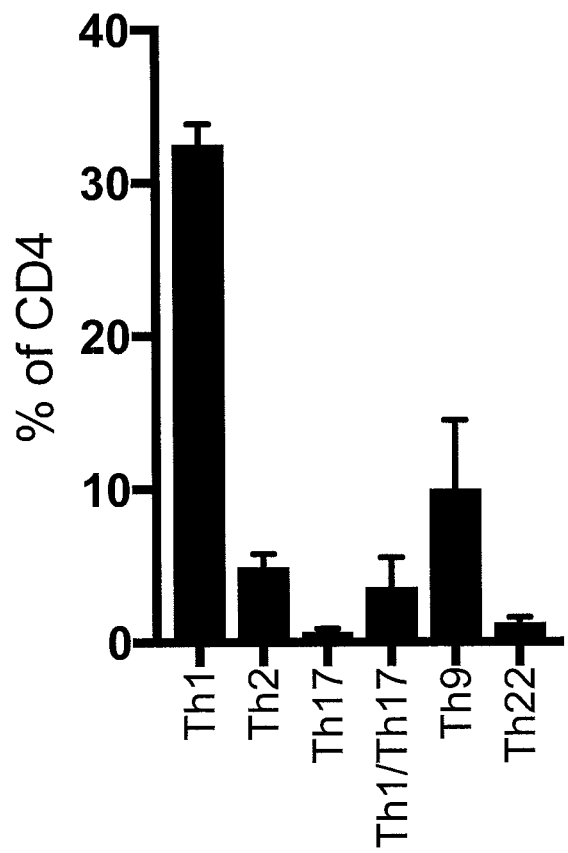

FIG. 7 shows the percentage of different CD4 T helper subtypes present in the panfungal T cell product; $T_h1$ (CCR4$^-$CCR6$^-$CCR10$^-$CXCR3$^+$), $T_h2$ (CCR4$^+$CCR6$^-$ CXCR3$^-$), $T_h9$ (CCR4$^-$CCR6$^+$), $T_h17$ (CCR4$^+$CCR6$^+$ CCR10$^-$CXCR3$^-$), $T_h22$ (CCR4$^+$CCR6$^+$CCR10$^+$), $T_h1$/ $T_h17$ (CCR4$^-$CCR6$^+$CXCR3$^+$). Results are means of 3 experiments (±s.e.m) and shown as percent of CD4 T cells.

Figure 8:
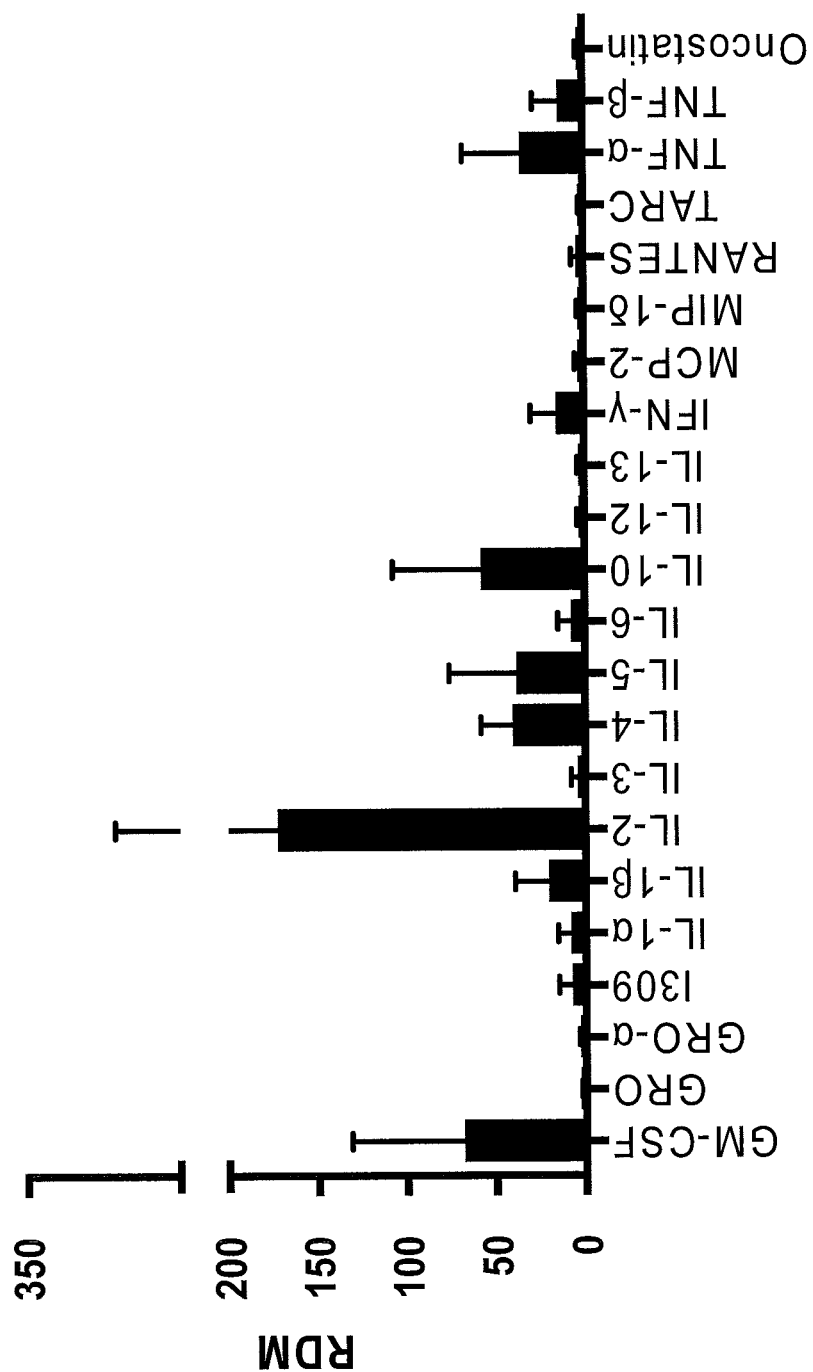

FIG. 8 shows results from an immunoblot analysis of cytokine in supernatants of fungus-specific T cells cultured for 24 h with non-pulsed DCs (control) or fungus-pulsed DCs (activated). Data (means±s.e.m of 2 experiments) are presented as relative density measurement (RDM) in activated fungus-specific T cells relative to control.

Figure 9:
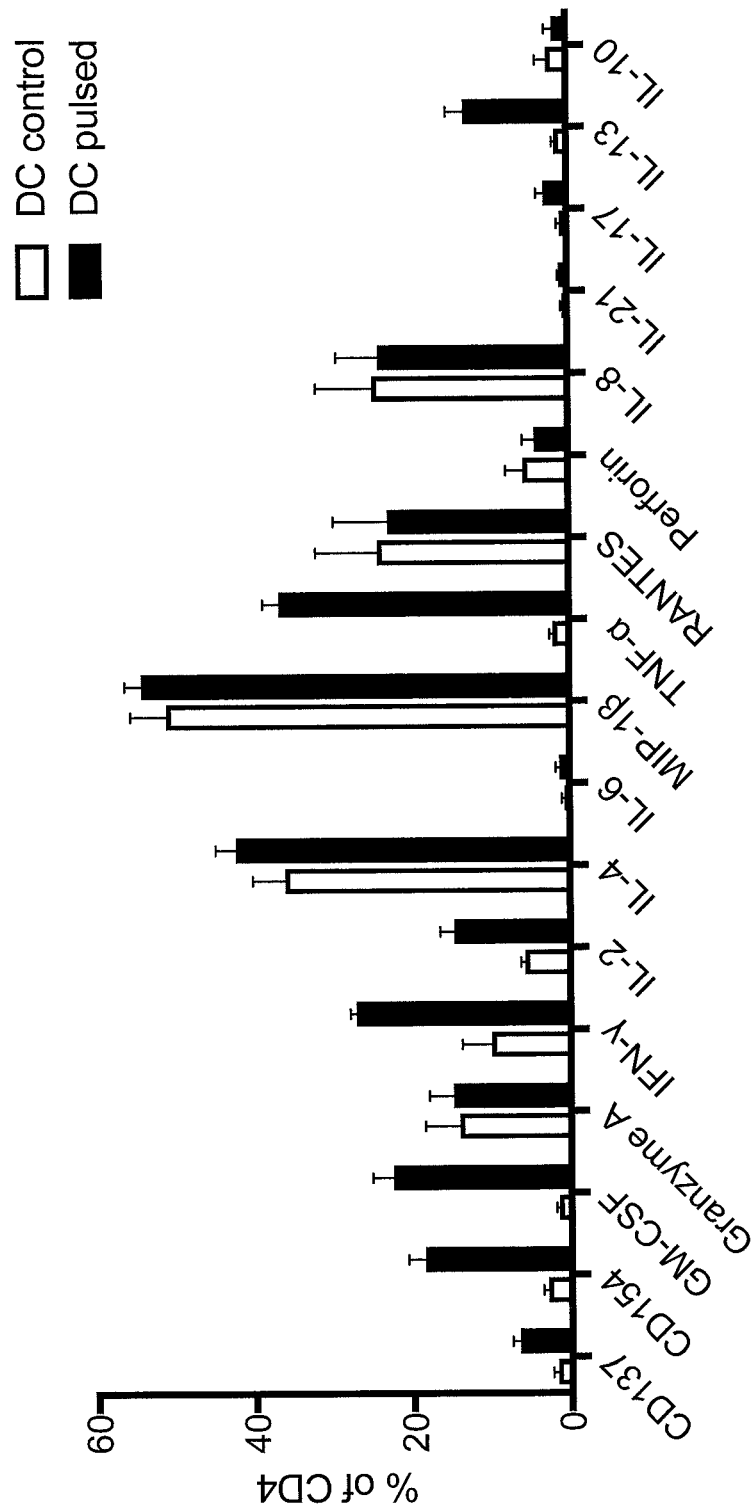

FIG. 9 shows the cytokine expression profile of panfungal T cells cultured for 5 h with non-pulsed DCs or fungus-pulsed DCs. Results are means of 3 experiments (±s.e.m) and shown as percentage of CD4$^+$ T cells.

Figure 10:
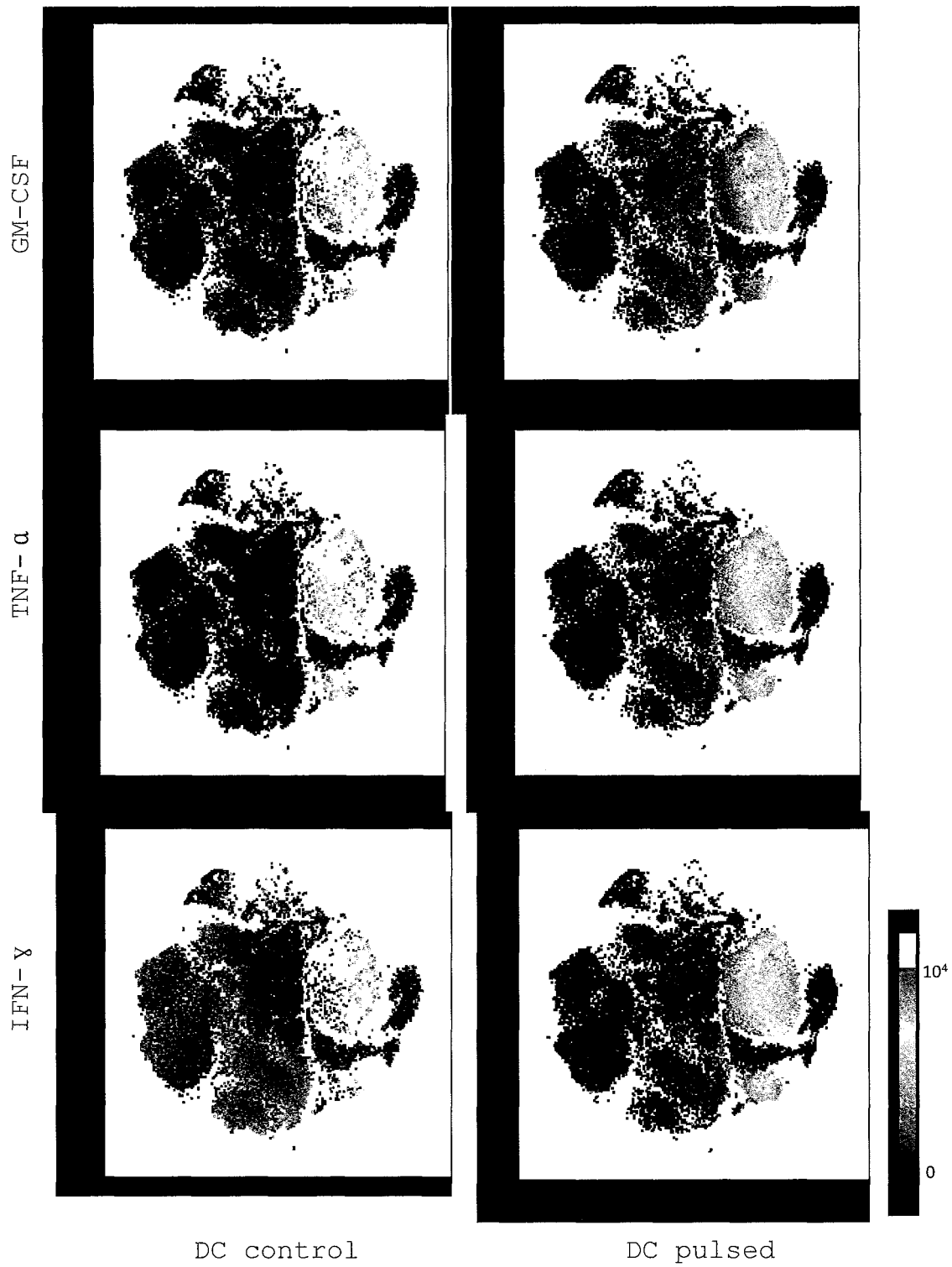

FIG. 10 is a t-distribution stochastic neighbourhood embedding (t-SNE) plot showing the mapping of panfungal T cells cultured for 5 h with non-pulsed DCs or fungus-pulsed DCs. Responding fungus-specific T cells correspond to the cell cluster showing higher GM-CSF, IFN-γ and TNF-α expression, indicative of a majority cells with similar phenotype. t-SNE plots for CD3, CD4, CD8, CD45RA, CD62L, CCR7, TIM3, LAG3, PD-1, CTLA-4, HLA-DR, IL-2, IL-4, IL-6, IL-8, IL-10, IL-13, IL-21, TNF-α, IFN-γ, GM-CSF, MIP-1β, RANTES, Foxp3, Tbet, CD154, CD137, CD57, IL2R, CD28, CD27, CD28, CD25, CD127, CCR4, CCR6 and CCR10 and CXCR3 are representative of control and pulsed DC treated panfungal T cells from 3 experiments.

Figure 11:
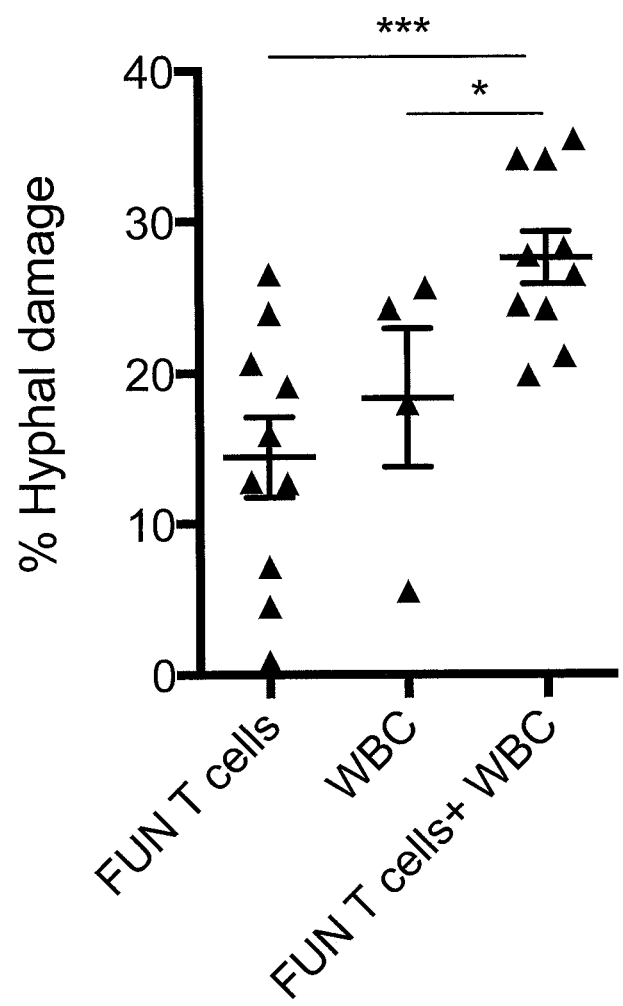

FIG. 11 shows the percent of hyphal damage (assessed by XTT colorimetric assay) induced by T cells, white blood cells (WBC) and combination of both after 2 h incubation with germinated conidia from *A. fumigatus*. Results are means of 4 experiments (±s.e.m) and shown as percent of hyphal damage relative to non-treated hyphae (*p≤0.05 and **p≤0.001 treatment versus none; Student's t-test).

Figure 12:
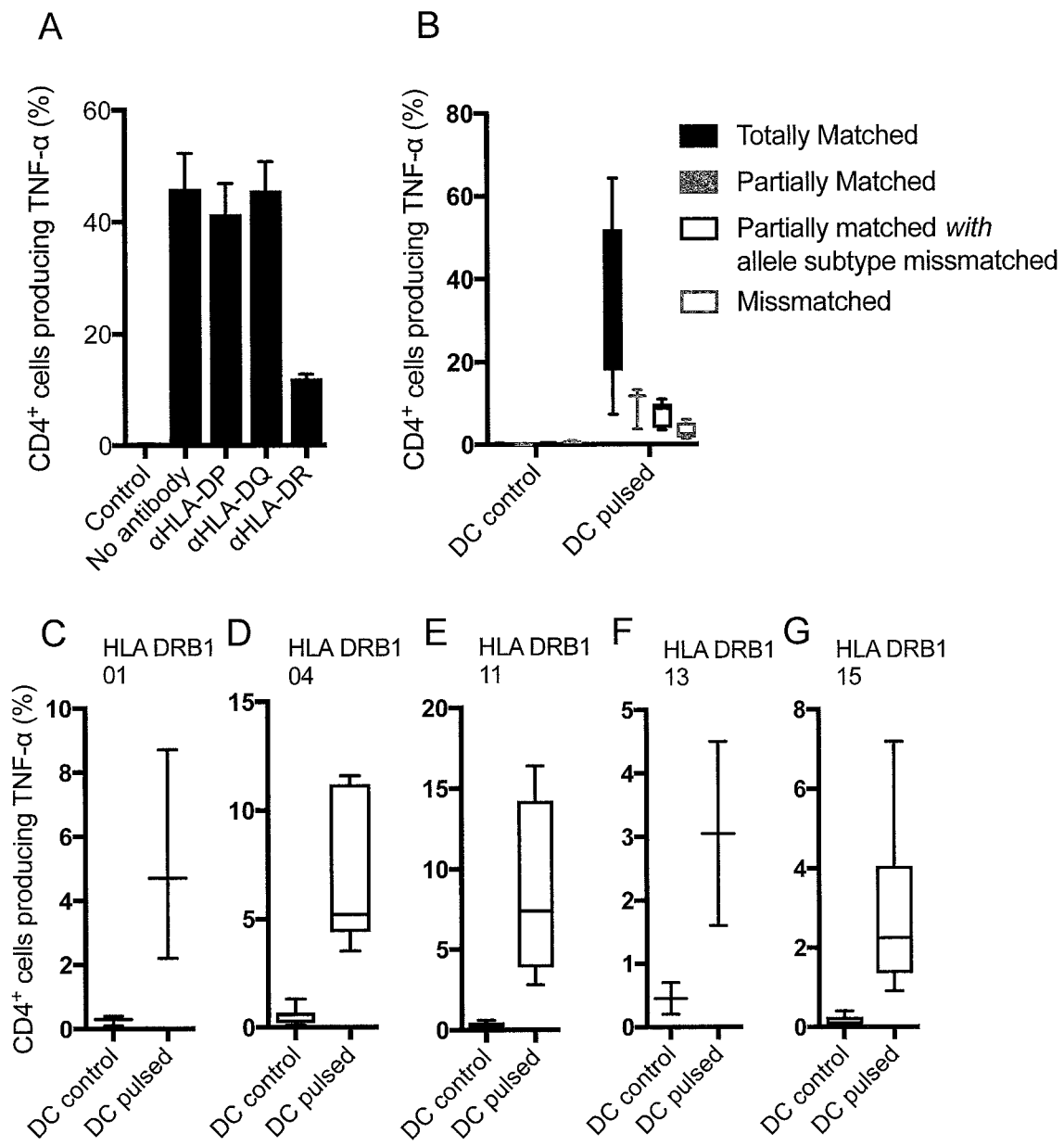

FIG. 12 is a graphical characterisation of multipathogen T cell cultures initiated by simultaneous stimulation with antigens from *A. terreus* and *C. krusei*, followed by CD137 selection and in vitro expansion. A. Inhibition of CD4+ production of TNF-α following incubation of dendritic cells pulsed with fungal lysate and fungus specific T cells in the presence of specific HLA DRB1, DP and DQ antibodies showing that the production of TNF-α is mediated principally via HLA DRB1. B. Percentage of CD4+ cells producing TNF-α following presentation of fungal antigen by DCs that are autologous to the fungus specific T cells, partially matched at HLA DRB1 (ie, one of two HLA DRB1 antigens fully allelic matched), partially matched with allele subtype mismatched (one of two HLA DRB1 antigen matched but allelic mismatched). C.-G. Percentage of CD4+ panfungal T cells generated using starting populations of DRB1 01:01, 04:01, 11:01, 13:01 or 15:01 able to recognize fungal antigens presented through other allelic subtypes of each of those DRB1 antigens. C. Panfungal T cells generated using HLA DRB1 01:01 T cells respond to fungal antigens presented on DCs expressing HLA DRB1 01:02. D. Panfungal T cells generated using HLA DRB1 04:01 T cells respond to fungal antigens presented on DCs expressing HLA DRB1 04:03, HLA DRB1 04:04 and HLA DRB1 04:05. E. Panfungal T cells generated using HLA DRB1 11:01 T cells respond to fungal antigens presented on DCs expressing HLA DRB1 11:04. F. Panfungal T cells generated using HLA DRB1 13:01 T cells respond to fungal antigens presented on DCs expressing HLA DRB1 13:02. G. Panfungal T cells generated using HLA DRB1 15:01 T cells respond to fungal antigens presented on DCs expressing HLA DRB1 15:02. Results are means of 3 to 6 experiments (±s.e.m) and shown as percent of CD4 T cells.

Figure 13:
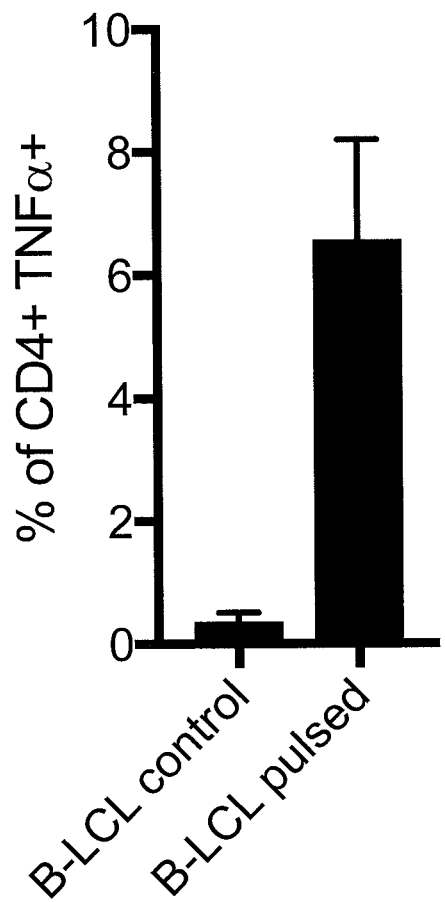

FIG. 13 shows that HLA DRB1 homozygous B cell lymphoblastoid cell lines (B-LCL) present fungal antigen to CD4+ fungus T cells and can be used for screening of HLA element of restriction. TNF-α production by HLA DRB1 heterozygous fungal T cells (originally expanded with *A. terreus* and *C. krusei*) following presentation of fungal antigen by HLA DRB1 homozygous B cell lymphoblastoid cell lines (B-LCL) on a single matched HLA DRB1 shared with the T cells. Results are means of 5 experiments (±s.e.m) and shown as percent of CD4+ T cells.

Figure 14:
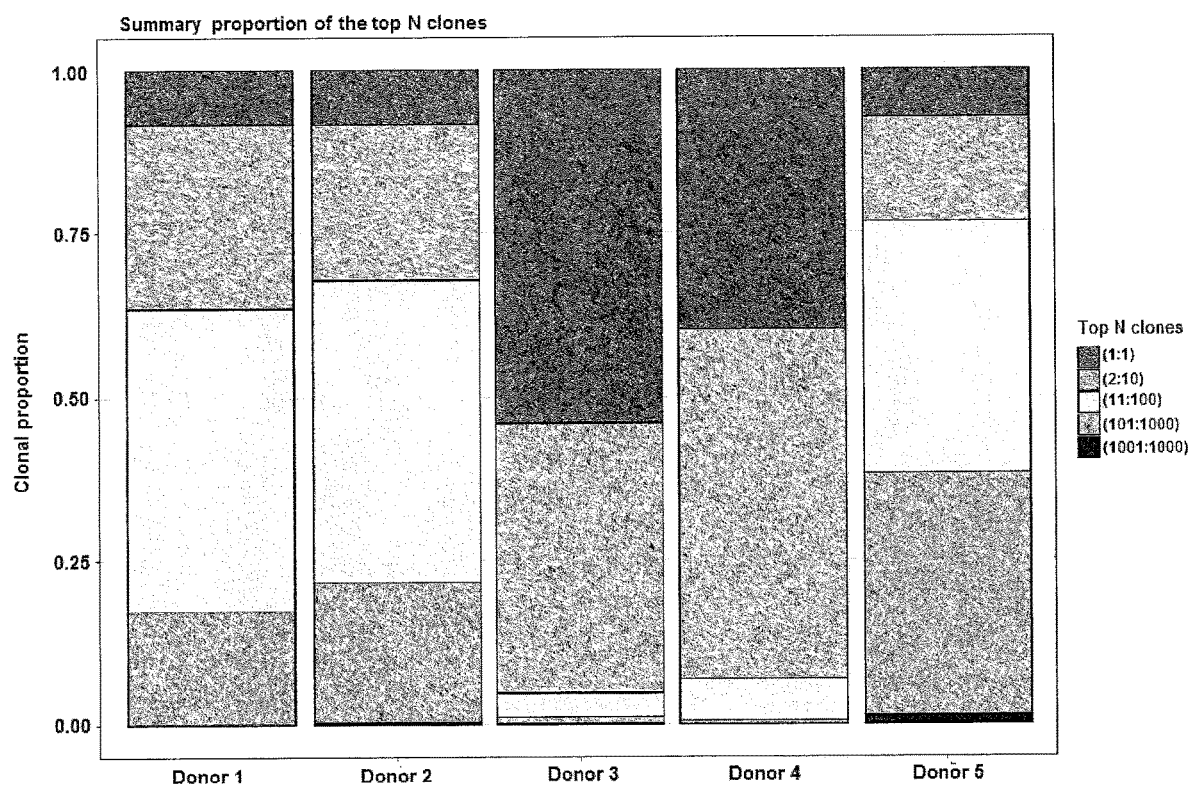

FIG. 14 shows the proportion of the top TCR-β sequences expressed in reactive *A. fumigatus*-specific T cells from 5 normal donors (CD4+CD154+ cells) after 16 h activation showing that 25% of sequences in all products were derived from up to only 10 clones and that a single clone was identified in 5-55% of TCR-β sequences. The ordering of each box in the legend on the right hand side of the graph is the same as the ordering of each segment in the graph.

Figure 15:
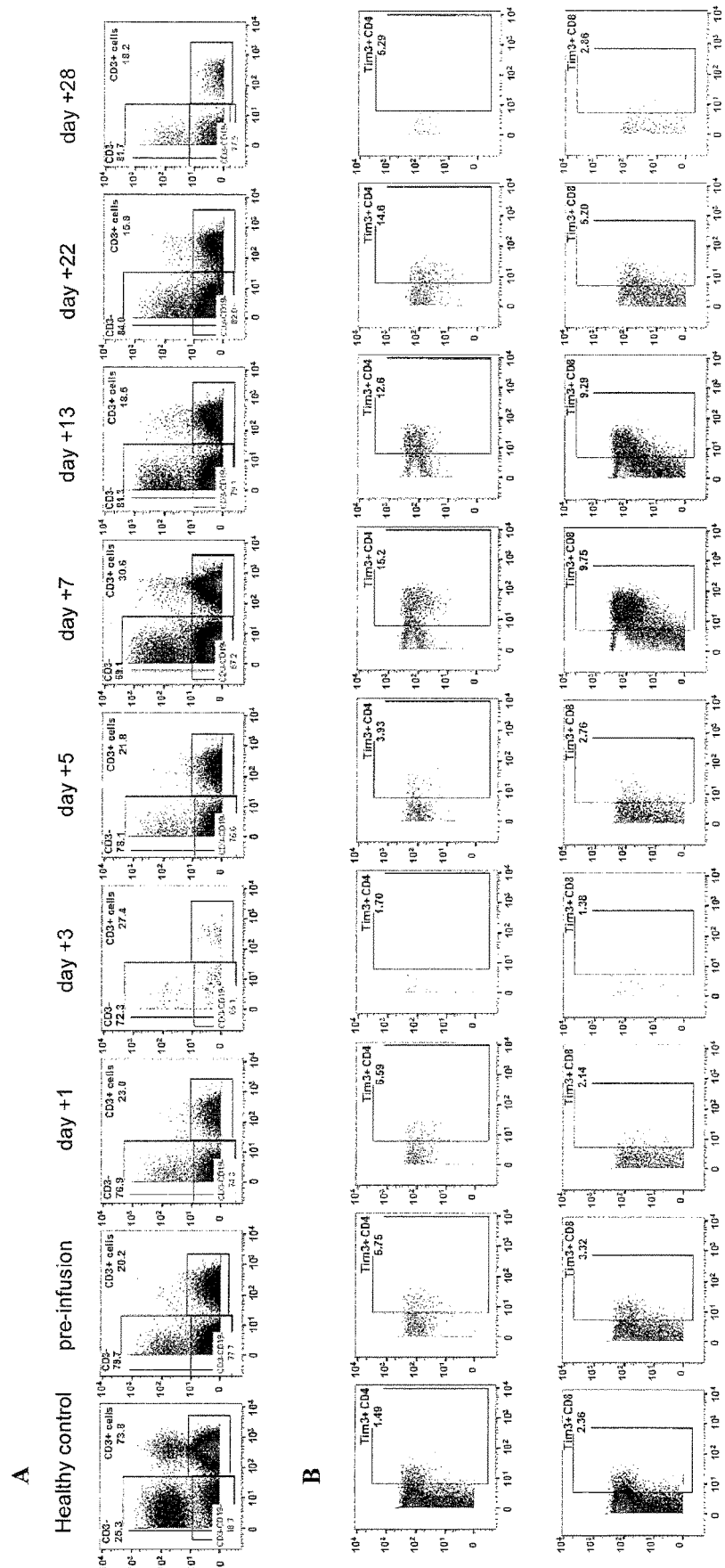
Figure 15:
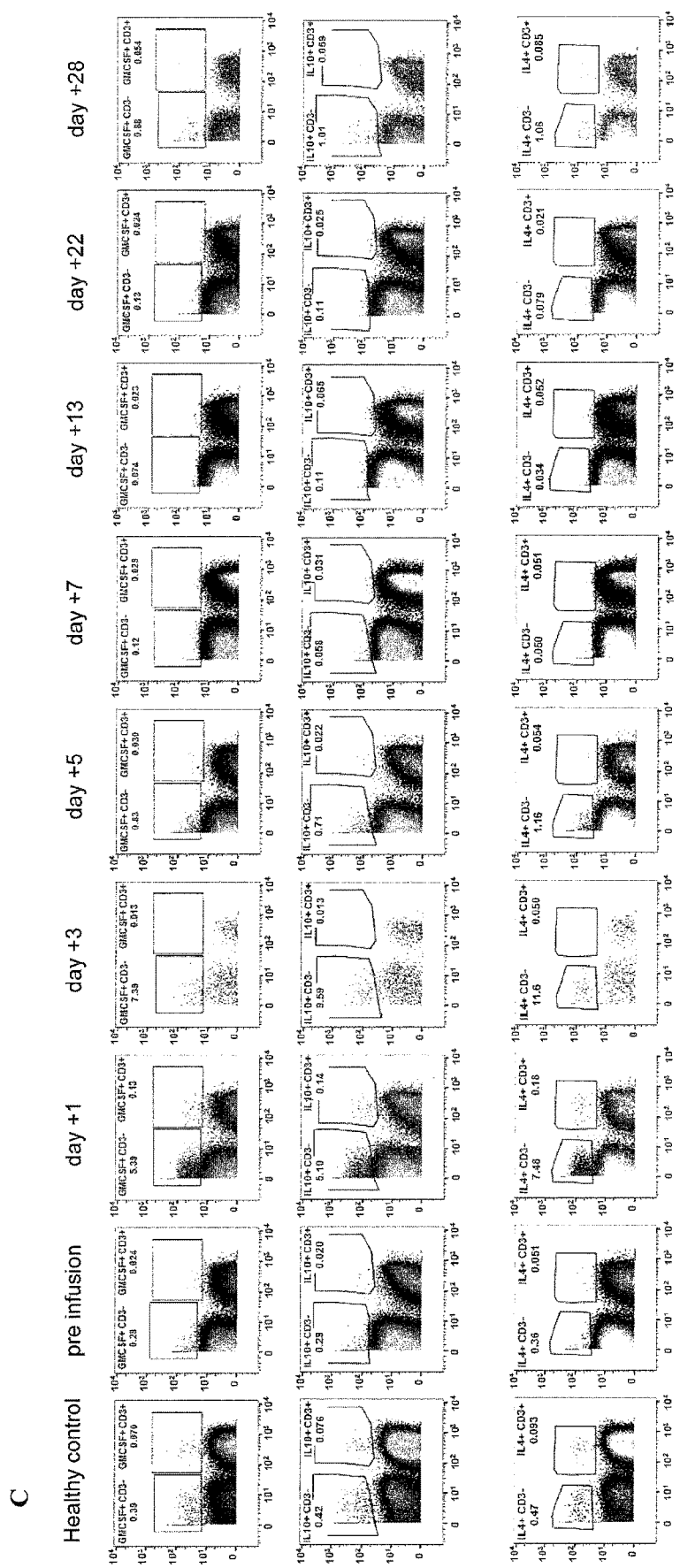
Figure 15:
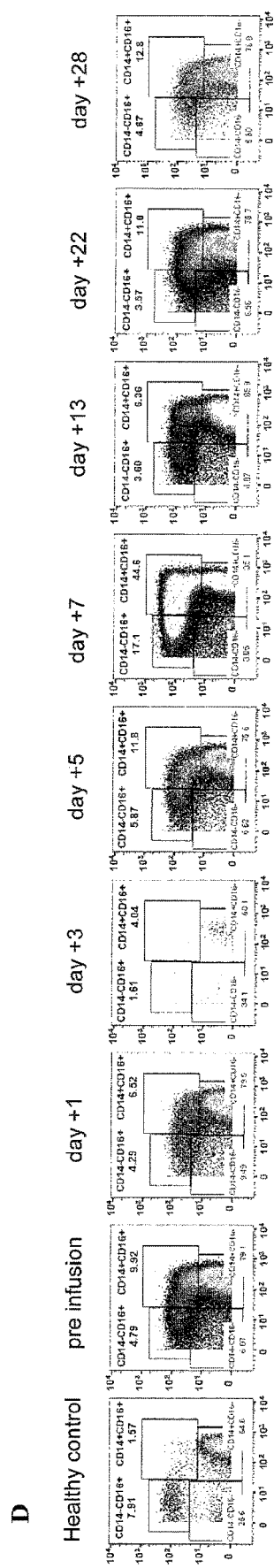

FIG. 15 is a graphical characterisation of peripheral blood mononuclear cells from a healthy male control aged 47 years, and from a male patient aged 51 years with disseminated *Scedosporium boydii* and treated with a composition comprising T cells. A. Plots show live cells gated and analysed as CD3 v CD20. B. Plots show gated CD4+ cells as CD45RO v CD366 (Tim3) (upper row) and gated CD8+ cells as CD45RO v CD366 (Tim3) (lower row). C. Plots show total live cells gated and analysed as CD3 v GM-CSF (upper row), CD3 v IL10 (middle row) and CD3 v IL4 (bottom row). D. Plots show live cells sequentially gated as CD3-CD20-HLA DR+CD56– and analysed as CD14 v CD16.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the present disclosure described herein is to be applied mutatis mutandis to each and every other example unless specifically stated otherwise.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure, as described herein.

The present disclosure is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; Benny K. C. Lo, Antibody Engineering: Methods and Protocols, (2004) Humana Press, Vol. 248; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, ppl-22; Atkinson et al., pp 35-81; Sproat et al., pp 83-115; and Wu et al., pp 135-151; Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara Biochem. Biophys. Res. Commun. 73: 336-342, 1976; Merrifield J. Am. Chem. Soc. 85: 2149-2154, 1963; Barany and Merrifield (1979) in The Peptides (Gross, E. and Meienhofer, J. eds.), vol. 2, pp. 1-284, Academic Press, New York. 12. Wünsch, E., ed. (1974) Synthese von Peptiden in Houben-Weyls Metoden der Organischen Chemie (Müler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky Int. J. Peptide Protein Res. 25: 449-474, 1985; Handbook of Experimental Immunology, Vols. I-IV (D. M. Weir and C. C. Blackwell, eds., 1986, Blackwell Scientific Publications); and Animal Cell Culture: Practical Approach, 3rd edn (John R. W. Masters, ed., 2000), ISBN 0199637970, whole of text.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

"T cells" belong to a group of white blood cells known as lymphocytes, and play a central role in cell-mediated immunity and, to a lesser degree the adaptive immune response. Generally, T cells are distinguished from other lymphocytes (e.g., B cells and natural killer cells) by the presence of T cell receptors (TCRs). T cells have diverse roles, which are accomplished by differentiation of distinct populations of T cells, recognizable by discrete gene expression profiles.

As used herein, the term "reactive" shall be taken to mean a T cell that is responsive to an antigen stimulus. For example, it refers to a T cell having antigenic reactivity against fungi, virus or tumour.

The term "fungi" or "fungus", as used herein, refers to a member of a large group of eukaryotic organisms that may include microorganisms, e.g., yeasts and moulds. These organisms may be classified as a kingdom of fungi, which is separate from plants, animals, and bacteria. One major difference between fungi and the others is that fungal cells have cell walls that contain chitin, unlike the cell walls of plants, which contain cellulose.

As used herein, the terms "fungi", "fungus", or "fungal" may refer to fungi which may cause infection in humans and animals. Such fungi may also be referred to as "pathogenic fungi".

As used herein, the term "extract" shall be taken to refer to a fungal extract obtained by any extraction method, whether or not the crude extract has been fractionated or purified. The term "extract" and "lysate" in relation to fungal extracts are used interchangeably herein.

As used herein, the term "water soluble lysate" shall be taken to mean a fungal lysate that substantially dissolved in water under the conditions of temperature and concentration at which the lysate is to be used.

The term "germinated spores" as used herein shall be taken to mean a fungal spore that has been subjected to germination conditions.

As used herein, the term "obtaining the lysate" shall be taken to include the process of homogenization of the germinated fungal spores and purification of the lysate.

The term "virus" or "viral" as used herein, refers to a small infectious agent that replicates only inside the living cells of other organisms. Exemplary viruses include cytomegalovirus (CMV), Epstein-Barr virus (EBV), adenovirus (AdV), varicella zoster virus (VZV), influenza and BK virus (BKV), John Cunningham (JC) virus, respiratory syncytial virus (RSV), parainfluenzae, rhinovirus, human metapneumovirus, herpes simplex virus (HSV) 1, HSV II, human herpes virus (HHV) 6, HHV 8, hepatitis A virus, hepatitis B virus, hepatitis C virus, hepatitis E virus, rotavirus, papillomavirus and parvovirus.

The term "viral antigen" as used herein refers to a protein encoded by the viral genome or a peptide derived therefrom. The viral antigen may be in the form of overlapping peptides from viral proteins, a lysate of virally infected cells. The viral antigen may also be presented by or expressed by recombinant cells (e.g., cells genetically engineered with retrovirus, lentivirus or other vectors).

The term "tumour antigen" as used herein refers to a protein encoded by a tumour genome or a peptide derived therefrom. The tumour antigen may be in the form of overlapping peptides from tumour proteins (e.g., a peptide pool). Examples of tumour antigens include wilms tumour antigen (WT1), beta chain of human chorionic gonadotropin (hCG beta) antigen, carcinoembryonic antigen (CEA), alphafetoprotein (AFP), CD19, CD20, CA-125, epithelial tumor antigen (ETA), abnormal products of ras, p53, glycosphingolipid GD2, prostatic acid phosphatase (PAP), preferentially expressed antigen in melanoma (PRAME), B melanoma antigen (BAGE), cancer-testis antigen (NY ESO-1), sarcoma antigen 1 (SAGE), helicase antigen (HAGE), cancer-germline antigen (GAGE), prostein (P501S), six-transmembrane epithelial antigen of the prostate (STEAP), Plu-1, human achaete-scute homolog-1 (hASH1), Cripto, Criptin, EGFRvIII antigen, Globo H antigen, GM2 antigen, GP100 antigen, HER2/neu antigen, KSA antigen, Le (y) antigen, Melanoma-associated antigen (MAGE), MUC1 antigen, MUC2 antigen, MUC3 antigen, MUC4 antigen, MUC5AC antigen, MUC5B antigen, MUC7 antigen, prostate specific antigen (PSA), PSCA antigen, early prostate cancer antigen (EPCA-2, prostate-specific membrane antigen (PSMA), Thompson-Friedenreich antigen (TF), Tn antigen, sTn antigen, tyrosinase-related protein 1 (TRP 1) antigen, tyrosinase-related protein 2 (TRP 2) antigen, tumor-specific immunoglobulin variable region and tyrosinase antigen.

As used herein, the term "defined number" refers to a set number or amount of cells or population of cells in the composition. As the skilled person will be aware, when dealing with a cell based composition, the definition a specific number does not mean that exact number of cells is to be included in a composition. For example, a variation of up to about 10% is encompassed by this term.

As used herein, the term "defined ratio" refers to the quantitative relationship between two or more amounts showing the number of times one value contains or is contained within the other. For example, the compositions described herein may comprise a defined ratio of two or more populations of T cells, each population being reactive to a particular antigen. As the skilled person will be aware, when dealing with a cell based composition, the definition a specific ratio does not mean that exact ratio of cells is to be included in a composition. For example, a variation of up to about 10% is encompassed by this term.

As used herein the term "enriched" or "enrich" in the context of a cell population shall be taken to encompass a population of CD137 T cells, including a population in which the number or percentage of CD137 T cells is greater than the number or percentage in a naturally occurring cell population. For example, a CD137 enriched population is made up of at least about 0.02% of said cells, or at least about 0.05% of said cells or at least about 0.1% of said cells or at least about 0.2% of said cells or at least about 0.5% of said cells or at least about 0.5% of said cells or at least about 0.8% of said cells or at least about 1% of said cells or at least about 2% of said cells or at least about 3% of said cells or at least about 4% of said cells or at least about 5% of said cells or at least about 10% of said cells or at least about 15% of said cells or at least about 20% of said cells or at least about 25% of said cells or at least about 30% of said cells or at least about 40% of said cells or at least about 50% of said cells or at least about 60% of said cells or at least about 70% of said cells or at least about 80% of said cells or at least about 85% of said cells or at least about 90% of said cells or at least about 95% of said cells or at least about 97% of said cells or at least about 98% of said cells or at least about 99% of said cells.

As used herein the term "*Mycoplasma*" refers to a genus of bacteria that lack a cell wall around their cell membrane. *Mycoplasma* can be parasitic or saprotrophic.

As used herein, the term "effective amount" shall be taken to mean a sufficient quantity of the composition to confer a therapeutic or protective immune response against fungi in a subject. The skilled artisan will be aware that such an amount will vary depending on, for example, the fungi and/or the particular subject and/or the type or severity of a condition being treated. Accordingly, this term is not to be construed to limit the disclosure to a specific quantity, for example, weight or number of population of cells of the composition of the present disclosure.

As used herein, the term "confers" shall be taken to mean that administration of the composition of the present disclosure initiates an immune response in a subject.

The term "therapeutic immune response" shall be taken to mean that administration of the composition is sufficient to induce an immune response that results in the reduction or inhibition of one or more symptoms of the infection.

The term "protective immune response" shall be taken to mean that administration of the composition is sufficient to induce an immune response that is capable of reducing or inhibiting, via IgG antibody production or T cell activation or enhancement of the actions of innate immune effectors such as monocytes, macrophages and/or neutrophils, infection.

As used herein, the term "condition" refers to a disruption of or interference with normal function, and is not to be limited to any specific condition, and will include diseases or disorders.

As used herein, the terms "treating", "treat" or "treatment" include administering a cell or cells described herein to thereby reduce or eliminate at least one symptom of a specified condition or disease.

As used herein, the term "subject" shall be taken to mean any animal, such as, a mammal. In one example, the mammal is a human or non-human primate. In one example, the mammal is a human.

As used herein, the term "donor" refers to a subject from whom cells are collected, said cells being intended for the preparation of a bank according to the present disclosure or for future preparation of a composition according to the present disclosure. The donor may be a stem cell donor from whom cells are collected as part of stem cell transplantation. Alternatively, the donor may be a solid organ donor from whom cells are collected as part of an organ transplant.

As used herein, the term "autologous" shall be taken to mean the cells are obtained from the subject that is undergoing treatment with the cells of the present disclosure.

As used herein, the term "non-autologous" shall be taken to mean the cells are from a donor. For example, the cells are obtained from a subject that is different from the subject receiving the treatment with the cells of the present disclosure.

As used herein, the term "major histocompatibility complex" or "MHC" refers to a set of cell surface molecules encoded by a large gene family in all vertebrates. MHC molecules may mediate interactions of leukocytes, also called white blood cells (WBCs), which are immune cells, with other leukocytes or body cells. MHC determines compatibility of donors for organ transplant as well as one's susceptibility to an autoimmune disease via cross-reacting immunization. In humans, MHC is also called human leukocyte antigen (HLA).

Antigens
Fungal Antigens

Exemplary fungi of the present disclosure include filamentous fungi, e.g., of the genera *Aspergillus, Fusarium, mucor/zygomycetes (Rhizopus)* and *Scedosporium/Lomentospora* species, and the yeast *Candida*. In one example, the fungus is of the *Aspergillus* genera. In one example, the fungus is yeast of the *C. krusei* genera. For example, the filamentous fungi include *A. fumigatus, A. flavus, A. terreus, F. oxysporum, F. solani, R. oryzae* and *L. prolificans*. In one example, the fungus is *A. terreus*. Exemplary yeast of the present disclosure includes *C. albicans* and *C. krusei*. In one example, the yeast is *C. krusei*.

In one example, the fungus is isolated from the environment. For example, *A. fumigatus, A. terreus* and *F. oxysporum* are isolated from the environment.

In one example, the fungus is isolated from a clinical specimen. For example, *A. fumigatus, A. terreus, F. oxysporum, F. solani, R. oryzae, L. prolificans, C. albicans, C. krusei, G. glabrata* are obtained from clinical specimens. Methods for isolating fungal lysates from clinical specimens are known in the art and described, for example, in Braedel et al. *British Journal of Haemotology*, 125: 392-399, 2004 or Gaundar et al. *Cytotherapy*, 14: 1119-1130, 2012.

In a further example, the fungus is obtained from a repository, such as the American Type Culture Collection (ATCC). For example, *A. flavus* is obtained from ATCC. In one example, the *A. flavus* is strain ATCC-204304.

In one example, a T cell of the disclosure is reactive with a fungal or yeast spore, e.g., a cultured and/or germinated spore. Methods for culturing and germinating fungal spores will be apparent to the skilled person. In one example, fungi isolated from the environment, clinical specimens or the ATCC are sub-cultured on potato dextrose agar plates for 3-7 days. Spores are removed by washing and separated from hyphal fragments by passing through 40 μm or 60 μm pore filters. Spores are germinated in potato dextrose medium for 16-72 hours at 25-37° C. with agitation at 200 rpm.

In one example, extracts or lysates of fungi or spores are produced. Methods for purification of fungal lysates or extracts will be apparent to the skilled person. In one example, the germinated spores of the fungi are lysed. For example, the lysates are obtained by homogenizing germinated spores of fungi. As exemplified herein, following germination of the spores, the mycelial mat is washed with sterile water and then homogenized using 0.5 mm zirconia-silica beads in a mini-beadbeater-8 cell homogenizer. Fungal lysates are clarified by centrifugation and passed through 0.22 μm sterile filters.

Methods for measuring the protein content of fungal lysates will be apparent to the skilled person and include the bicinchoninic acid (BCA) protein assay kit.

In one example, the lysate is not contaminated with bacteria or fungi. In one example, the sterility of lysates is confirmed by the absence of bacterial or fungal growth after incubation for two weeks at 30° C. in liquid culture medium.

Viral Antigens

Exemplary viruses of the present disclosure include cytomegalovirus (CMV), Epstein-Barr virus (EBV), adenovirus (AdV), varicella zoster virus (VZV), influenza and BK virus (BKV), John Cunningham (JC) virus, respiratory syncytial virus (RSV), parainfluenzae, rhinovirus, human metapneumovirus, herpes simplex virus (HSV) 1, HSV II, human herpes virus (HHV) 6, HHV 8, hepatitis A virus, hepatitis B virus, hepatitis C virus, hepatitis E virus, rotavirus, papillomavirus and parvovirus.

In one example, the viral antigen is in the form of overlapping peptides from viral proteins or a lysate of virally infected cells. For example, the viral antigen is a peptide pool that consists mainly of 15-mer peptides with 11-amino acid overlap (e.g., a PepTivator®). In one example, the viral antigen is presented by or expressed by recombinant cells (e.g., cells genetically engineered with retrovirus, lentivirus or other vectors).

Tumour Antigens

Exemplary tumour antigens of the present disclosure include wilms tumour antigen (WT1), beta chain of human chorionic gonadotropin (hCG beta) antigen, carcinoembryonic antigen (CEA), alphafetoprotein (AFP), CD19, CD20, CA-125, epithelial tumor antigen (ETA), abnormal products of ras, p53, glycosphingolipid GD2, prostatic acid phosphatase (PAP), preferentially expressed antigen in melanoma (PRAME), B melanoma antigen (BAGE), cancer-testis antigen (NY ESO-1), sarcoma antigen 1 (SAGE), helicase antigen (HAGE), cancer-germline antigen (GAGE), prostein (P501S), six-transmembrane epithelial antigen of the prostate (STEAP), Plu-1, human achaete-scute homolog-1 (hASH1), Cripto, Criptin, EGFRvIII antigen, Globo H antigen, GM2 antigen, GP100 antigen, HER2/neu antigen, KSA antigen, Le (y) antigen, Melanoma-associated antigen (MAGE), MUC1 antigen, MUC2 antigen, MUC3 antigen, MUC4 antigen, MUC5AC antigen, MUC5B antigen, MUC7 antigen, prostate specific antigen (PSA), PSCA antigen, early prostate cancer antigen (EPCA-2, prostate-specific membrane antigen (PSMA), Thompson-Friedenreich antigen (TF), Tn antigen, sTn antigen, tyrosinase-related protein 1 (TRP 1) antigen, tyrosinase-related protein 2 (TRP 2) antigen, tumor-specific immunoglobulin variable region and tyrosinase antigen.

In one example, the tumour antigen is in the form of overlapping peptides from tumour proteins. For example, the tumour antigen is a peptide pool that consists mainly of 15-mer peptides with 11-amino acid overlap (e.g., a PepTivator®).

T Cell Populations

From the description herein, the skilled person will be able to identify suitable T cells for use in the present disclosure. Exemplary T cells are isolated from peripheral blood mononuclear cells (PBMCs), cord blood, G-CSF mobilized hematopoietic progenitor cells (HPCs), bone marrow, splenic tissue, thymic tissue and lymph nodes. In one example, the T cells are isolated from PBMCs. In a further example, T cells are isolated from G-CSF mobilised HPCs. In another example, T cells are isolated from bone marrow.

In one example, PBMC are isolated from heparinised blood by gradient centrifugation over Ficoll-paque. In one example, the donors of peripheral blood are immunologically normal undergoing therapeutic venesection. In one example, 300-500 mL of peripheral blood is collected for isolation of PBMC. In one example, the PBMC are cryopreserved in 10% dimethylsulfoxide (DMSO) solution.

In one example, monocytes are isolated following mobilisation of stem cells by administration of granulocyte-colony stimulating factor (G-CSF). In one example, donors of stem cells are healthy individuals donating for allogeneic hematopoietic stem cell transplantation. In one example, the monocytes are freshly isolated. In another example, the PMSC or monocytes are cryopreserved in 10% DMSO solution.

In one example, monocytes are isolated following harvest of bone marrow. In one example, donors of bone marrow are healthy individuals donating for allogeneic hematopoietic stem cell transplantation. In one example, the bone marrow mononuclear cells are freshly isolated. In another example, the bone marrow mononuclear cells are cryopreserved in 10% DMSO solution.

In one example, HPC are isolated by washing in phosphate buffered saline containing 1% human albumin. In one example, the HPC are freshly isolated. In another example, the HPC are cryopreserved in 10% DMSO solution.

Exemplary T cell populations include naïve T cells, T helper cells ($T_H$ cells), terminally differentiated effector T cells ($T_{eff}$ cells), effector memory T cells ($T_{em}$ cells), central memory T cells ($T_{cm}$ cells), cytotoxic T cells (CTLs) and regulatory T cells ($T_{reg}$ cells). Exemplary T cell populations are at least 98% T cells and less than 2% B cells and monocytes. In one example, the T cells express at least CD3 and/or CD4.

Exemplary T cells are reactive with a fungal antigen, a viral antigen or a tumour antigen. In one example, the antigen-specific T cells are produced with G-CSF mobilised HSCs exposed to a fungal antigen, a viral antigen or a tumour antigen. For example, the T cells are produced with G-CSF mobilised HSCs exposed to a fungal extract of *C. krusei* or a fungal extract of *A. terreus*. In one example, the T cells are produced with G-CSF mobilised HSCs exposed to a viral antigen from cytomegalovirus or Epstein-Barr virus or varicella zoster virus or adenovirus. In one example, the T cells are produced with G-CSF mobilised HSCs exposed to a Wilms tumour 1 antigen In one example, the T cells are stimulated by culturing with direct addition of the fungal antigen, viral antigen or tumour antigen. In one example, the fungal extract is added at a concentration of 10 μg/ml. In one example, the viral antigen or tumour antigen is added in the form of a synthetic peptide pool. For example, the peptide pool is added at a concentration of 1 μg/ml.

In one example, the T cells are enriched for CD137 expressing cells following antigen stimulation. For example, the T cells are selected for using an antibody against CD137. In one example, the T cells are selected for using an immunomagnetic bead enrichment system (e.g., CliniMACS®).

In one example, the T cells are stimulated at least once. For example, the T cells are stimulated at least twice. For example, the T cells are stimulated twice.

Exemplary T cells are culture expanded following CD137 enrichment. In one example, the T cells are expanded in cell culture. Cells of the disclosure can be maintained under standard cell culture conditions.

Cell cultures can be incubated at about 37° C. in a humidified incubator. Cell culture conditions can vary considerably for the cells of the present disclosure. For example, the cells are maintained in an environment suitable for cell growth, e.g., comprising 5% $O_2$, 10% $CO_2$, 85% $N_2$ or comprising 10% $CO_2$ in air.

In one example, the T cells are co-cultured with CD137 negative cells. For example, the CD137 negative cells have been irradiated prior to co-culture. In one example, the T cells are expanded with one or more cytokines. For example, the T cells are expanded with interleukin-2 (IL-2). For example, the T cells are expanded with interleukin-15 (IL-15). For example, the T cells are expanded with interleukin-7 (IL-7). For example, the cells are expanded with IL-2, IL-15 and IL-7.

In one example, the T cells are cultured in AIM-V™ medium or any other appropriate cell culture medium known in the art. Other appropriate media include, Dulbecco's Minimal Essential Medium (DMEM), MCDB, Minimal Essential Medium (MEM), Iscove's Modified Dulbecco's Medium (IMDM) and Roswell Park Memorial Institute (RPMI) 1640 medium. In one example, the AIM-V™ medium is supplemented with 20 U/ml IL-2, 10 ng/ml IL-15 and 10 ng/ml IL-7. In one example, the AIM-V™ medium is supplemented with 10% heat inactivated autologous plasma.

In one example, the cultures are replenished about 2, or about 3 times per week using fresh medium containing the appropriate concentration of cytokines. Exemplary T cell cultures are maintained for a total of about 12-21 days. In one example, cell numbers are determined by counting in a haemocytometer.

In one example, the T cells express Th1 cytokines. For example, the T cells express a cytokine selected from the group consisting of TNFα, IFNγ, IL-17, RANTES, IL-2, MIP-1α, MIP-1β, IL-5, IL13, GM-CSF, IL-8 and combinations thereof.

In one example, the T cells are negative for bacterial and fungal contamination. For example, the T cells are negative for bacterial and fungal contamination for a period of at least 5 days.

In one example, the T cells are negative for *Mycoplasma* contamination.

In one example, the T cells are non-reactive for infectious disease markers, such as, the presence of endotoxin, hepatitis viruses A, B or C, human immunodeficiency viruses that can be present in blood.

Testing for Activity

Methods for testing activity of the T cells will be apparent to the skilled person based on the disclosure herein.

Testing for Lymphoproliferative Activity of Fungal Lysates

In one example, the lymphoproliferative activity of the fungal lysate is assessed.

One method for assessing the activity of fungal lysates on lymphoid cells is using a $^3$H-thymidine incorporation assay. Such a process may involve the stimulation of PBMC ($2\times10^5$ cells/200 µl) with 10 µg/ml of individual fungal lysate. IL-2 (25 U/ml) may be used as positive control and lysate from K562 cells (10 g/ml) may be used as an irrelevant control. The lymphoproliferative activity may be assessed by addition of one µCi of thymidine followed by overnight incubation at 37° C., lysing of cells and harvesting of the cellular material onto filter mats. $^3$H-thymidine incorporation can be assessed on a Microbeta™2 plate reader.

The reagents for determining lymphoproliferative activity are commercially available from Perkin Elmer.

Cell Phenotype Analysis

In one example, the T cells are phenotyped.

One method of phenotyping the T cells is staining the cells with fluorophore-conjugated antibodies to human CD3 (SK7), CD4 (RPA-T4), CD8 (SK1), CD19 (SJ25C1), CD14 (McpP9), CD56 (NCAM16.2), Vδ2TCR (B6), CD45RO (UCHL1), CD45RA (HI100), CD62L (Dreg56), CD25 (2A3), CD28 (L293), CD154 (TRAP1), CD161 (DX12) (all from BD; clones indicated in parentheses), Foxp3 (259D) (Biolegend) and CCR4 (205410) (R&D Systems).

Carboxyfluorescein Ester (CFSE) Proliferation Assay

In one example, the proliferative activity of the cultured T cells is assessed.

One method of assessing the proliferative activity of cultured T cells is to stain the cells with 1.5 µM carboxyfluorescein succinimidyl ester (CFSE) for 10 min at 37° C. then wash and culture the cells with individual antigen. The loss of CFSE fluorescence in cells after 7 days is then assessed by flow cytometry following co-staining with CD4 and CD8 antibodies.

Fungal Hyphal Damage Assay

In one example, the antifungal activity of the T cells is assessed.

One method of assessing the antifungal activity is using a calorimetric assay with 2,3-bis[2-methoxy-4-nitro-5-sulfophenyl]2H-tertrazolium-5-carboxyanilide sodium salt (XTT) and 2-methyl-1,4-napthoquinone (menadione). Such a process may involve germinating the fungal spores at 37° C. in 96-well microculture plates and incubating for a period of time. Exemplary incubation times include: *A. fumigatus* and *L. prolficans* 16-28 h, *A. terreus*, *C. albicans* and *C. krusei* 16-20 h. The hyphal masses are then washed twice in PBS by centrifuging at 15,000 g for 15 minutes in a plate centrifuge. PBMC, white blood cells (WBC) and fungus-specific T cells can then be added to appropriate wells at an effector to target ratio of 5:1 ($5\times10^4$ of each cell type). Following incubation at 37° C. for 2 hours, cells are lysed by washing twice in sterile water. The hyphal masses are resuspended in 200 µl sterile water and then 10 µl of XTT-menadione reagent is added to each well. The plate is vortexed gently then incubated at 37° C. for 2 hours. Following incubation, plates are centrifuged at 4,000 g for 10 minutes, the supernatant collected and the absorbance of the XTT reduction product (formazan) measured at 450 nm filter using a 620 nm reference on the Victor™ 3 plate reader. Absorbance may be standardized against unconverted XTT in wells containing only media and the XTT/menadione solution. Percent hyphal damage (HD) can be calculated as follows: % HD=(1−X/C)×100, where X is the absorbance of test well and C is the absorbance of the control wells with hyphae only.

Cytometric Bead Array

In one example the levels of cytokines in supernatants of antigen-stimulated T cells is assessed.

One method of assessing the levels of cytokines in supernatants of antigen-stimulated T cells is using a cytometric bead array. Such a process may involve stimulating cultured T cells with one or more or all fungal lysates or viral or tumour antigens (or no stimulation control). The levels of TNFα, IFNγ, IL-2, regulated upon activation, normal T cell expressed and secreted (RANTES), monocyte chemoattractant protein (MCP)-1, macrophage inhibitory protein (MIP)-1β, IL-4, IL-8 and IL-17 in the cell-free supernatants can be measured after 5 hours of stimulation by cytometric bead array.

A kit for performing the cytometric bead array is commercially available from BD.

T Cell Specificity and Function

In one example, the specificity of antigen-stimulated T cell cultures is assessed.

One method of assessing the specificity of antigen-stimulated T cell cultures is using flow cytometric analysis. Such a process may involve re-stimulating T cell cultures with antigen and incubating re-stimulated cells in the presence of anti-CD107a/b antibodies (to measure cytotoxic activity) for 5 hours and the co-stimulatory molecules CD28 and CD49d. Following 1 hour, monensin and brefeldin is added to allow intracellular accumulation of cytokines. Cells are then stained with antibodies to CD3, CD4 and CD8. After fixation and permeabilization, intracellular cytokines are stained with antibodies to IFNγ and TNFα. Cells are acquired and analysed on a fluorescence-activated cell sorting (FACS) machine (e.g., BD FACS Canto 2 using FACS diva software).

T Cell Compositions

The composition of the present disclosure is useful for parenteral administration for prophylactic or for therapeutic treatment of, e.g., superficial or invasive fungal disease, a viral infection, cancer, leukemia, lymphoma or other malignant disease.

In one example, the T cells are isolated following exposure to a fungal antigen or to a viral antigen or to a tumour antigen, and formulating the population(s) of cells into a pharmaceutically acceptable carrier.

In one example, the composition comprises one or more population(s) of T cells each population reactive with a fungal antigen.

In one example, the composition comprises one or more population(s) of T cells each population reactive with a viral antigen. For example, the viral antigen comprises overlapping peptides from viral proteins, a lysate of virally infected cells, cells genetically engineered with retrovirus, lentivirus or other vectors to express a viral protein.

In one example, the composition comprises one or more population(s) of T cells each population reactive with a tumour antigen. For example, the tumour antigen comprises overlapping peptides from tumour proteins, a lysate of tumour cells, cells genetically engineered to express a tumour protein.

In one example, the T cells are reactive with a fungal antigen from a fungal extract selected from the group consisting of *Aspergillus terreus, Candida krusei, Rhizopus oryzae, A. fumigatus, A. flavus, A. terreus, C. albicans, C. krusei, F. oxysporum, F. solani* and *L. prolificans*.

In one example, the T cells are reactive with a viral antigen from a virus selected from the group consisting of CMV, EBV, AdV, VZV, influenza, BK virus, JC virus, RSV, parainfluenzae, rhinovirus, human metapneumovirus, HSV 1, HSV II, HHV6, HHV8, hepatitis A virus, hepatitis B virus, hepatitis C virus, hepatitis E virus, rotavirus, papillomavirus and parvovirus.

In one example, the T cells are reactive with a tumour antigen selected from the group consisting of Wilms tumour antigen (WT1), beta chain of human chorionic gonadotropin (hCG beta) antigen, carcinoembryonic antigen (CEA), alphafetoprotein (AFP), CD19, CD20, CA-125, epithelial tumor antigen (ETA), abnormal products of ras, p53, glycosphingolipid GD2, prostatic acid phosphatase (PAP), preferentially expressed antigen in melanoma (PRAME), B melanoma antigen (BAGE), cancer-testis antigen (NY ESO-1), sarcoma antigen 1 (SAGE), helicase antigen (HAGE), cancer-germline antigen (GAGE), prostein (P501S), six-transmembrane epithelial antigen of the prostate (STEAP), Plu-1, human achaete-scute homolog-1 (hASH1), Cripto, Criptin, EGFRvIII antigen, Globo H antigen, GM2 antigen, GP100 antigen, HER2/neu antigen, KSA antigen, Le (y) antigen, Melanoma-associated antigen (MAGE), MUC1 antigen, MUC2 antigen, MUC3 antigen, MUC4 antigen, MUC5AC antigen, MUC5B antigen, MUC7 antigen, prostate specific antigen (PSA), PSCA antigen, early prostate cancer antigen (EPCA-2, prostate-specific membrane antigen (PSMA), Thompson-Friedenreich antigen (TF), Tn antigen, sTn antigen, tyrosinase-related protein 1 (TRP 1) antigen, tyrosinase-related protein 2 (TRP 2) antigen, tumor-specific immunoglobulin variable region and tyrosinase antigen.

In one example, the composition comprises at least two populations of T cells each population reactive with a fungal antigen, a viral antigen or a tumour antigen.

In one example, the composition comprises T cells reactive with fungal antigens only.

In one example, the composition comprises T cells reactive with viral antigens only.

In one example, the composition comprises T cells reactive with tumour antigens only.

In one example, the composition comprises one or more population(s) of T cells each population reactive with a fungal antigen and one or more population(s) of T cells each population reactive with a viral antigen.

In one example, the composition comprises one or more population(s) of T cells each population reactive with a fungal antigen and one or more population(s) of T cells each population reactive with a tumour antigen.

In one example, the composition comprises one or more population(s) of T cells each population reactive with a viral antigen and one or more population(s) of T cells each population reactive with a tumour antigen.

In one example, the composition comprises one or more population(s) of T cells each population reactive with a fungal antigen, one or more population(s) of T cells each population reactive with a viral antigen and one ore more population(s) of T cells each population reactive with a tumour antigen.

In one example, the composition comprises T cell products that meet the following release criteria:
Greater than 50% post thaw viability;
Less than 2% B cells and monocytes;
Negative for bacterial and fungal contamination at 5 days;
Negative for *Mycoplasma* contamination;
No evidence of alloreactivity defined as <10% specific cytotoxicity against recipient derived PHA blasts at a ratio of 20:1 effector cells to target cells in a standard $^{51}$CR assay;
Non-reactive for infectious disease markers.

In one example, the cells are autologous to the subject receiving the treatment. In one example, the cells are non-autologous to the subject.

Formulation of the composition to be administered will vary according to the route of administration and formulation (e.g., solution, emulsion) selected. An appropriate pharmaceutical composition comprising the composition of the present disclosure to be administered can be prepared in a physiologically acceptable carrier. A mixture of compositions can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate.

The optimum concentration of cell populations in the chosen medium can be determined empirically, according to procedures well known to the skilled artisan, and will depend on the ultimate pharmaceutical formulation desired.

In one example, the composition comprises a defined number or defined ratio of T cells in each population. For example, the composition comprises an equal number of T cells in each population. In another example, each population is combined in a ratio of between 1:1 and 1:99. For example, each population is combined in a ratio of about 1:1 to about 1:3.

In one example, the defined number or defined ratio is based on a subject's clinical situation or clinical diagnosis. For example, the number or ratio of cells in a population is based on the perceived likelihood of severe infection with varying types of transplant. For example, a subject undergoing cord blood transplantation can receive a product with specificities for all available pathogens, whilst a subject undergoing a matched sibling transplant can receive only T cell populations targeting pathogens based on the reduced likelihood of opportunistic infection following transplant. In another example, a subject with features of a specific infection that have or have not been confirmed by diagnostic investigations (e.g., CT scan, X-ray, blood test etc) can receive a higher number or ratio of fungal specific T cells in the composition due to the likelihood of systemic fungal infection. In a further example, a subject with a history of a known infection prior to a planned or unplanned period of immunosuppression can receive a higher number or ratio of T cells specific for that infection as part of a composition.

In another example, the defined number or defined ratio is based on a subject's serology or infectious status. For example, a subject seropositive and/or viral nucleic acid test positive for a pathogen can receive a composition comprising T cells reactive with the specific pathogen. In one example, the defined number or defined ratio is based on a subject's previous serology or infectious status. For example, a composition can be based on the detection of specific pathogens detected in a period prior to administration to target specific infections likely to become clinically apparent.

In another example, the defined number or defined ratio is based on a known profile for an infection. For example, if a pathogen is commonly associated with a disease or condition, T cells reactive with the pathogen can be included in the composition. In one example, the defined number or defined ratio is based on the age of patient undergoing allogeneic stem cell transplant. For example, a paediatric patient is more likely to develop systemic adenovirus infection and thus is more likely to receive a composition with a high number or ratio of adenovirus specific T cells.

In another example, the defined number or defined ratio is based on a known diagnosis of a tumor. For example, a patient with acute myeloid leukemia expressing the WT1 tumor antigen can receive a composition comprising an increased number or ratio of WT1 specific T cells. In another example, a patient with acute lymphoblastic leukemia expressing CD19 can receive a composition comprising an increased number or ratio of CD19 targeted T cells (e.g., CD19 chimeric antigen receptor bearing T cells).

Dosage and Administration

The dosage ranges for the administration of the composition of the disclosure are those large enough to produce the desired effect. For example, the composition comprises an amount sufficient to confer a therapeutic or protective immune response in the subject.

The dosage should not be so large as to cause adverse side effects, such as hyper viscosity syndromes, pulmonary edema, congestive heart failure, and the like. Generally, the dosage will vary with the age, condition, sex and extent of the disease in the subject and can be determined by one of skill in the art. The dosage can be adjusted by the individual physician in the event of any complication.

Dosage can vary from about $1\times10^3$ cells/kg to about $1\times10^{10}$ cells/kg. For example the composition can comprise about $1\times10^3$ cell/kg to about $1\times10^4$ cells/kg, or about $1\times10^4$ cell/kg to about $1\times10^5$, or about $1\times10^5$ cell/kg to about $1\times10^6$, or about $1\times10^6$ cell/kg to about $1\times10^7$, or about $1\times10^7$ cell/kg to about $1\times10^8$, or about $1\times10^8$ cell/kg to about $1\times10^9$, or about $1\times10^9$ cell/kg to about $1\times10^{10}$. Dosage can vary from about $1\times10^5$ cells/m$^2$ to about $1\times10^{10}$ cells/m$^2$. For example, about $1\times10^5$ cells/m$^2$ to about $1\times10^6$ cells/m$^2$, or about $1\times10^6$ cells/m$^2$ to about $1\times10^7$ cells/m$^2$, or about $1\times10^7$ cells/m$^2$ to about $1\times10^8$ cells/m$^2$, or about $1\times10^8$ cells/m$^2$ to about $1\times10^9$ cells/m$^2$, or about $1\times10^9$ cells/m$^2$ to about $1\times10^{10}$ cells/m$^2$. For example, about $1\times10^7$ cells/m$^2$, or about $2\times10^7$ cells/m$^2$, or about $3\times10^7$ cells/m$^2$, or about $4\times10^7$ cells/m$^2$ or about $5\times10^7$ cells/m$^2$.

In one example, the dosage of each population in the composition can vary from about $1\times10^3$ cells/kg to about $1\times10^{10}$ cells/kg. For example each population in the composition can comprise about $1\times10^3$ cell/kg to about $1\times10^4$ cells/kg, or about $1\times10^4$ cell/kg to about $1\times10^5$, or about $1\times10^5$ cell/kg to about $1\times10^6$, or about $1\times10^6$ cell/kg to about $1\times10^7$, or about $1\times10^7$ cell/kg to about $1\times10^8$, or about $1\times10^8$ cell/kg to about $1\times10^9$, or about $1\times10^9$ cell/kg to about $1\times10^{10}$. Dosage can vary from about $1\times10^5$ cells/m$^2$ to about $1\times10^{10}$ cells/m$^2$. For example, about $1\times10^5$ cells/m$^2$ to about $1\times10^6$ cells/m$^2$, or about $1\times10^6$ cells/m$^2$ to about $1\times10^7$ cells/m$^2$, or about $1\times10^7$ cells/m$^2$ to about $1\times10^8$ cells/m$^2$, or about $1\times10^8$ cells/m$^2$ to about $1\times10^9$ cells/m$^2$, or about $1\times10^9$ cells/m$^2$ to about $1\times10^{10}$ cells/m$^2$. For example, about $1\times10^7$ cells/m$^2$, or about $2\times10^7$ cells/m$^2$, or about $3\times10^7$ cells/m$^2$, or about $4\times10^7$ cells/m$^2$ or about $5\times10^7$ cells/m$^2$.

In one example, the dosage may be administered in one or more dose administrations. In one example, the dosage can be repeated at least once. For example, the dosage is repeated at intervals depending on the immune state of the subject and the response to the previous infusion. In this regard, the repeat dosage(s) need not be the same as previous dosage(s), e.g., it could be increased or decreased.

In one example, the composition is administered intravenously.

In the case of a subject that is not adequately responding to treatment, multiple doses may be administered. Alternatively, or in addition, increasing doses may be administered.

Conditions to be Treated

In one example, administration of the T cell population to a subject confers a therapeutic immune response against fungi or a virus or a tumour.

In one example, administration of the T cell population to a subject confers a protective immune response against fungi or a virus or a tumour.

In one example, the subject is suffering from a disease or condition. For example, the disease or condition is a cancer, such as a blood or bone marrow cancer, for example the cancer includes multiple myeloma, leukemia, lymphoma, neuroblastoma, Ewing sarcoma, myelodysplastic syndromes and gliomas. In another example, the disease or condition is a non-malignant condition, for example thalassemia, aplastic anemia, fanconi anemia and immune deficiency syndromes. In a further example, the condition or disease is associated with infection or graft-versus host disease.

In one example, the subject is undergoing treatment for a disease or condition. In one example, the subject is about to commence or has completed treatment for a disease or condition. In one example, the treatment is chemotherapy, hematopoietic stem cell transplantation or immunoablation. For example, the subject is undergoing or about to commence or has completed chemotherapy and/or hematopoietic stem cell transplantation and/or immunoablation therapy.

In one example, the subject is about to receive or has received transplantation of a solid organ such as a kidney, liver, pancreas, pancreatic islets, heart, lungs, small bowel or other solid organ.

In one example, the subject is receiving or has received immunosuppressive drug treatment or antibody treatment or soluble receptor treatment or another immunomodulating treatment for a disease such as, but not limited to, inflammatory bowel disease, rheumatoid arthritis, multiple sclerosis, hepatitis, glomerulonephritis and kidney failure, cancer, lymphoma, leukemia, myelodysplasia, myeloma.

In one example, the subject has inherited or been born with a deficiency of the immune system such as, but not limited to, severe combined immune deficiency, common variable immunodeficiency, alymphocytosis, Wiskott Aldrich syndrome, ataxia telangiectasia, di George syndrome, leucocyte adhesion defects, immunoglobulin deficiency.

In one example, the subject has an acquired immunodeficiency through infection with the human immunodeficiency virus or another pathogenic organism that has led to incompetence of the immune system.

In one example, the subject is suffering from chronic relapsing fungal infections such as, but not limited to, chronic or relapsing oral or vulvovaginal candidiasis, chronic or relapsing fungal skin infection, chronic or relapsing fungal nail infections, chronic or relapsing fungal bronchial infections, chronic or relapsing fungal sinus infections, chronic or relapsing fungal myocardial infections, chronic or relapsing fungal cerebral infections, chronic or relapsing fungal bone infections, chronic or relapsing fungal liver infections, chronic or relapsing fungal kidney or bladder infection.

Phenotyping of Cells for Use in Therapy and Banking

In one example, the cells of the present disclosure are HLA-allele phenotyped. For example, the cells are partially HLA-allele phenotyped.

In one example, the cells have alleles selected from major HLA, such as any Class I, II or III HLA, minor HLA, and non-polymorphic alleles, such as any member of the CD1 family members.

Major HLA alleles may more specifically be selected from any class I HLA such as HLA-A1, HLA-A2, HLA-A3, HLA-A24, HLA-A11, HLA-A28, HLA-A29, HLA-A32, HLA-B15, HLA-B5, HLA-B7, HLA-B8, HLA-B12, HLA-B14, HLA-B18, HLA-B35, HLA-B40, HLA-C group 1, HLA-C group 2 for example, any class II HLA-DPB9, HLA-DPB11, HLA-DPB35, HLA-DPB55, HLA-DPB56, HLA-DPB69 HLA-DPB84 HLA-DPB 87, HLA-DRB1, HLA-DQA1, HLA-DQB1, or any class III HLA. The knowledge of a HLA phenotype can facilitate subsequent selection of cells for the preparation of the composition of the present disclosure.

In one example, at least one class I HLA is phenotyped. For example, at least one HLA-A, HLA-B or HLA-C is phenotyped.

In one example, at least one class II HLA is phenotyped. For example, at least one of HLA-DR, HLA-DP or HLA-DQ is phenotyped.

In one example, at least one HLA-allele in the cells of the present disclosure is matched to at least one HLA-allele in the subject to which the composition is administered. For example, the matched HLA antigen is the antigen presenting an infection or tumour antigen to the T cells in the subject. For example, at least one class I HLA is matched. For example, at least one of HLA-A, HLA-B and HLA-C is matched. In another example, at least one class II HLA is matched. For example, at least one of HLA-DR, HLA-DP and HLA-DQ is matched.

In one example, the HLA antigen is the same for each population of cells in the composition. For example, the phenotype of the HLA antigen in the cells of the present disclosure is matched to a HLA antigen in the subject to which the composition is administered. In one example, the method of treating a subject comprises determining an HLA antigen in the subject, matching the HLA antigen to an HLA antigen in T cells in a composition in the bank and administering to the subject a composition comprising T cells having the same HLA antigen as that in the subject. In one example, the HLA is different for different infection and tumor specificities. For example, the HLA antigen in each population of T cells in the final composition matches different HLA antigen in the subject depending on the infection and tumor specificity. In one example, the HLA antigen is an HLA-DR antigen, or an HLA-A antigen, or an HLA-B antigen, or an HLA-C antigen, or an HLA-DP antigen, or an HLA-DQ antigen, or a combinations thereof.

In one example, the method additionally comprises testing the composition for anti-fungal activity. For example, the method comprises testing the composition for activity against a fungus with which a subject is infected.

Banking of T Cells

In one example, a plurality of T cell compositions are in a bank.

The cells for use in the present disclosure may be "banked" for future use, at a cell bank or depository or storage facility, or any place where such as cells are kept cryopreserved, e.g., in liquid nitrogen, for safekeeping. Furthermore, appropriate computer systems can be used for data processing, to maintain records relating to donor information and to ensure rapid and efficient retrieval of cells from the storage repositories.

In one example, each of the storage containers (e.g., bags or tubes) can be tagged with positive identification based on a distinctive property associated with the donor, lines or cell type, prior to storing in a bank according to the disclosure. For example, DNA genetic fingerprint and HLA typing may be used with secured identification mechanism such as acceptable methods using microchips, magnetic strip, and/or bar code labels. This identification step may be included in the banking process.

In one example, at least one of the HLA antigens in the T cells in each composition in the bank has been identified. In one example, the HLA is a HLA-DR antigen or an HLA-A antigen, or an HLA-B antigen, or an HLA-C antigen, or an HLA-DP antigen, or an HLA-DQ antigen.

In one example, the specificity of the T cells (i.e., the target antigen) has been identified. In one example, the target antigen is a viral antigen or a fungal antigen or a tumor antigen.

In one example, the HLA antigen presenting the target antigen to the T cell has been identified. In one example, the HLA antigen is HLA-0201 presenting a CMV peptide NLVPMVATV. In one example, the HLA antigen is HLA-DR04 presenting a fungal antigen. In one example, the HLA antigen is HLA-B7 presenting an EBV antigen.

At the time of use, only the required storage unit is retrieved, the number of units necessary to fulfil a desired dosage being selectable. Certain diseases may require cell therapy that includes a series of repeated treatments. The population of cells may be extracted from the bank and increased by cellular expansion before preparation of the pharmaceutical composition and administration to the subject.

Suitable cells for use in the preparation of the composition of the present disclosure may be obtained from existing cell banks, or may be directly collected from one or more donor subjects and later banked. In one example, cells are collected from healthy subjects. For example, cells from tissues that are non-essential to the subject may also be appropriate as they reduce the risk of induction of autoimmune disease.

Standards for donor selection may include one or more of the following considerations prior to collection, such as (a) absence of specific disease; (b) specific or general diseases; (c) parameters of the donor relating to certain diseases, for example a certain age, certain physical conditions and/or symptoms, with respect to certain specific diseases, with respect to certain prior treatment history and/or preventive treatment, etc.; (d) whether the donor fits into one or more established statistical and/or demographic models or profiles (e.g., statistically unlikely to acquire certain diseases); and (e) whether the donor is in a certain acceptable health condition as perceived based on prevailing medical practices, etc.

In one example, the cells are collected by apheresis from donor's peripheral blood, processed (to optimise the quantity and quality of the collected cells) and, optionally cryogenically preserved or maintained in culture under suitable conditions.

In one example, the donor is a stem cell donor. For example, the cells are collected by apheresis as part of the stem cell donation. In one example, the cells are collected after administration of G-CSF to the donor alone or in combination with chemotherapy or a stem cell mobilising agent. In one example, the cells are collected by bone marrow harvest.

In one example, the cells are collected by apheresis from the donor's peripheral blood or from the bone marrow by marrow harvest and are used for the preparation of the composition if the number of cells collected exceeds the number required for the purposes of stem cell transplantation. For example, the cells collected for the preparation of the composition are in excess of the cells required for stem cell transplantation.

The collected cells can be aliquoted into defined dosage fractions. The cells may be stored under any appropriate conditions, such as in culture or in a cryopreserved state. Methods of cell storage will be apparent to the skilled person. For example, cryopreservation of cells can be achieved using a variety of cryoprotecting agents, such as DMSO.

In one example, the cells may be cryopreserved at different stages. For example, the cells may be cryopreserved as PBMC, isolated monocytes, isolated CD137 selected cells, and CD137 selected cells after about 1 to 2 weeks culture.

As exemplified herein T cells are cryopreserved for adoptive T cell transfer. For example, a freezing mix containing 40% saline, 40% Albumex20 and 20% DMSO is prepared. The saline is added to the DMSO and chilled before adding the Albumex20. The freezing mix is kept chilled until required.

The cells for cryopreservation are resuspended, pooled and mixed thoroughly. The cells are counted using a haemocytometer and the cell concentration and total cell viability is determined.

The cells are spun at 1400 rpm for 5 mins and 10 mls of the supernatant is removed for sterility and *Mycoplasma* testing. The remaining supernatant is discarded.

The cells are washed with up to 200 ml of 0.9% saline supplemented with Albumex20 and spun at 1400 rpm for 5 mins.

The cells are resuspended in 0.9% saline at a concentration of $2\times10^7$ cells/ml.

For cryopreserving the T cells the maximum volume of cells to be added per bad is to be calculated using the formula. Maximum volume per bag (mL)=Max number of cells required per bag/$1\times10^7$ per ml.

The number of bags and quality assurance samples to be cryopreserved is determined. An equal volume of freezing mix is added to the T lymphocyte suspension and mixed. The required volume of cells is transferred into cryopreservation bags and/or vials. The bags and vials are immediately placed into pre-cooled rate controlled freezers to begin cryopreservation.

EXAMPLES

Example 1—Isolation of Fungal Antigens and PBMCs

Isolation of Fungal Antigens

Pure strains of fungi were isolated from the environment (*Aspergillus fumigatus* strain WMI-008, *A. terreus* WMI-026 and *Fusarium oxysporum* WMI-011), from clinical specimens (*Fusarium solani, Rhizopus oryzae, Lomentospora prolificans, Candida albicans, C. krusei* and *C. glabrata*) or from ATCC (*A. flavus* strain ATCC-204304).

Fungi were sub-cultured on potato dextrose agar plates for 3-7 days. Spores were removed by washing and separated from hyphal fragments by filtration (40 μm or 60 μm pore filters). Spores were germinated in potato dextrose medium for 16-72 hours at 25-37° C. with agitation at 200 rpm. The mycelial mat was washed with sterile water and then homogenized. Lysates were clarified by centrifugation and passed through 0.22 μm sterile filters. Protein content was measured.

Sterility of lysates was confirmed by the absence of bacterial or fungal growth after incubation for two weeks at 30° C. in liquid culture medium. Lysates were stored at −80° C. To use as negative control, water-soluble lysate was prepared from K562 cells using the same homogenization procedure used for the preparation of fungal lysates.

Isolation of PBMC and HPC

Peripheral blood mononuclear cells (PBMC) were isolated from heparinised blood by gradient centrifugation over Ficoll-paque.

Peripheral blood stem cells (PMSC) were isolated following mobilisation of stem cells by administration of granulocyte-colony stimulating factor (G-CSF). Hematopoietic progenitor cells (HPC) were isolated and platelet-reduced by washing in phosphate buffered saline containing 1% human albumin.

Example 2—Generation of Fungus Specific T Cell Cultures

Platelet-reduced HPCs were incubated with 40 μg (10 μg/mL) of each fungal lysate (*A. fumigatus, A. terreus, C. krusei* or *C. krusei* and *A. terreus*) and 1 μg/ml CliniMACS® anti-CD28 pure AB reagent in complete AIM-V™ medium supplemented with 10% heat-inactivated auto-plasma for 16-18 hours at 37° C. and 5% $CO_2$. Unstimulated cells served as a negative control.

Following the incubation period, cells were labelled with CliniMACS® CD137 antibody reagent conjugated to biotin, washed and then incubated with a magnetic anti-Biotin reagent. Activated antigen specific T cells ($CD137^+$) were then selected by immunomagnetic enrichment using a MS magnetic column (Miltenyi Biotec) according to manufacturer instructions. The $CD137^+$ enriched population was resuspended in complete AIM-V™ medium supplemented with 10% auto-plasma and plated in a G-Rex cell culture plate. All CD137-enriched fungal T cells comprised at least 50% $CD3^+CD137^+$ cells (63.6±14.4%) from which at least 75% (82.3±6.9%) were $CD4^+$ cells.

Figure 1:
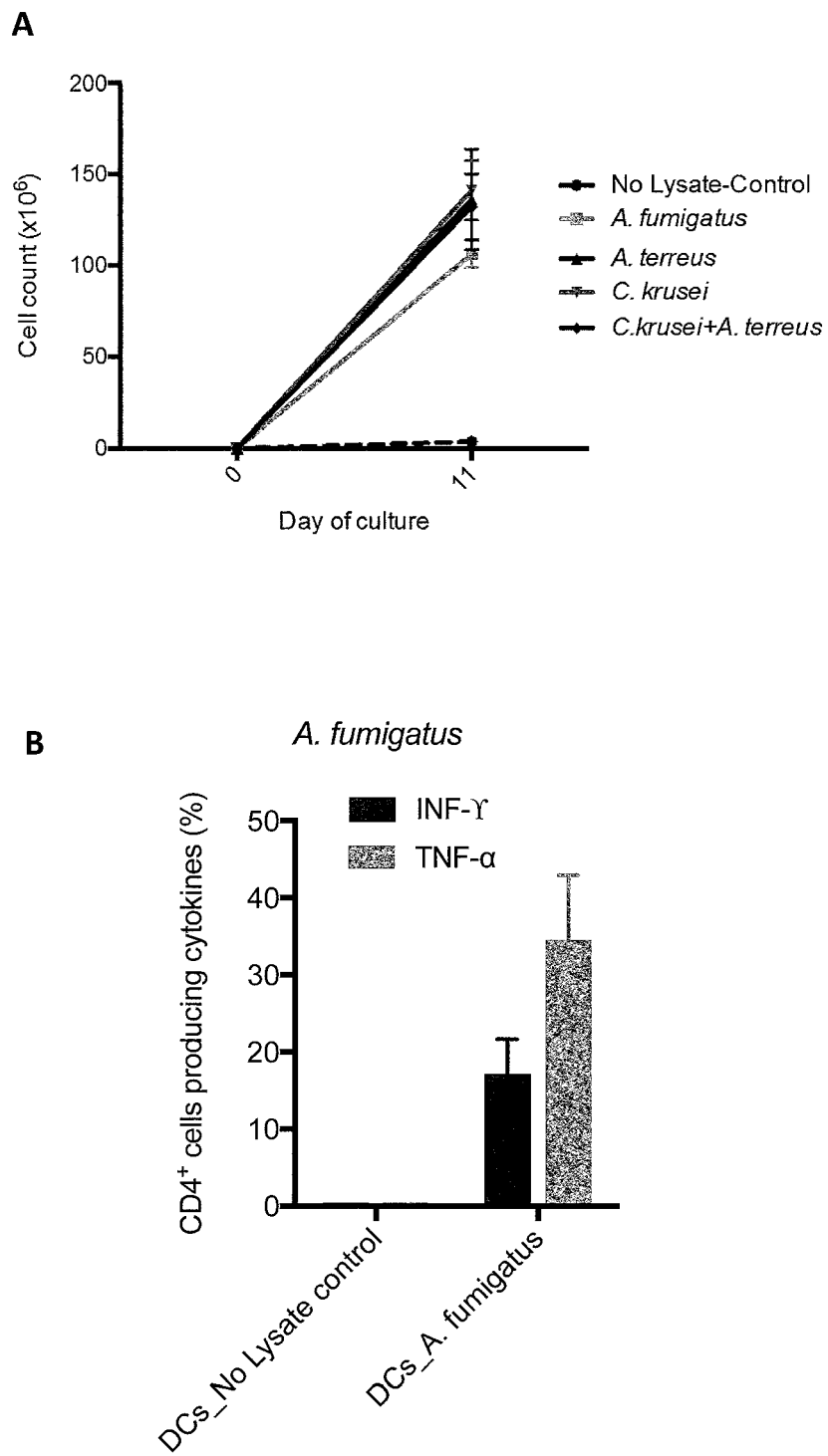
FIG. 1 is a graphical characterisation of individual fungal T cell cultures. A. Expansion of T cell cultures stimulated with individual fungal lysate followed by CD137 selection and expansion. Data expressed as mean±SEM (n=1-4). Percentage of responding $CD4^+$ cells from B. *A. fumigatus*, C. *A. terreus*, D. *C. krusei* following restimulation with the same lysate used to originate cultures or in the case of E. *A fumigatus*, F. *A terreus* G. *C krusei* following restimulation with the same lysate used to originate cultures or other lysates or all lysates together. Percentage of responding CD4+ cells from culture stimulated with a combination of *A* terreus and *C krusei* and H. rechallenged with *A terreus, C krusei* or all fungal lysates and I. as for H. but rechallenged with all individual lysates and all lysates combined (showing percentage of cells producing TNFα, INFγ and/or IL-17). Bars indicate means±SEM (n=3-6).
Figure 1:
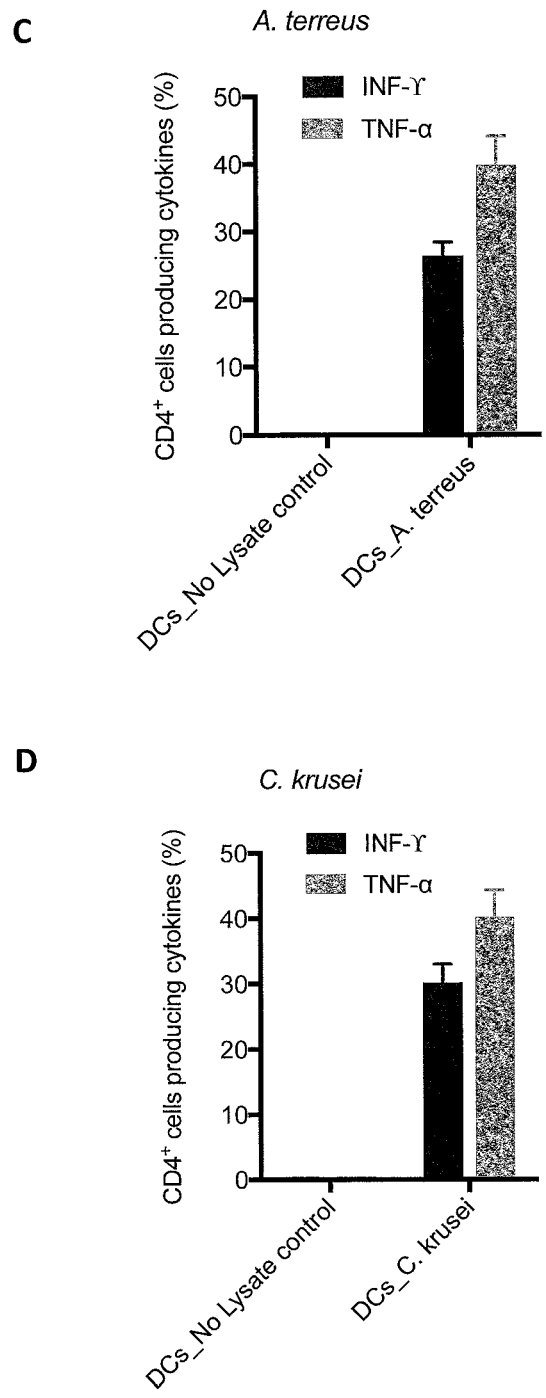
Figure 1:
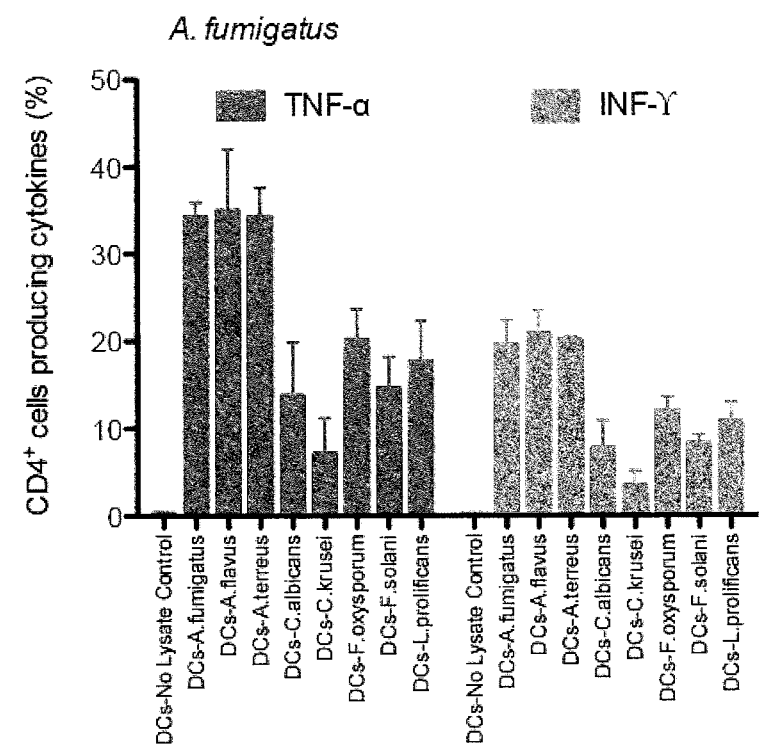
Figure 1:
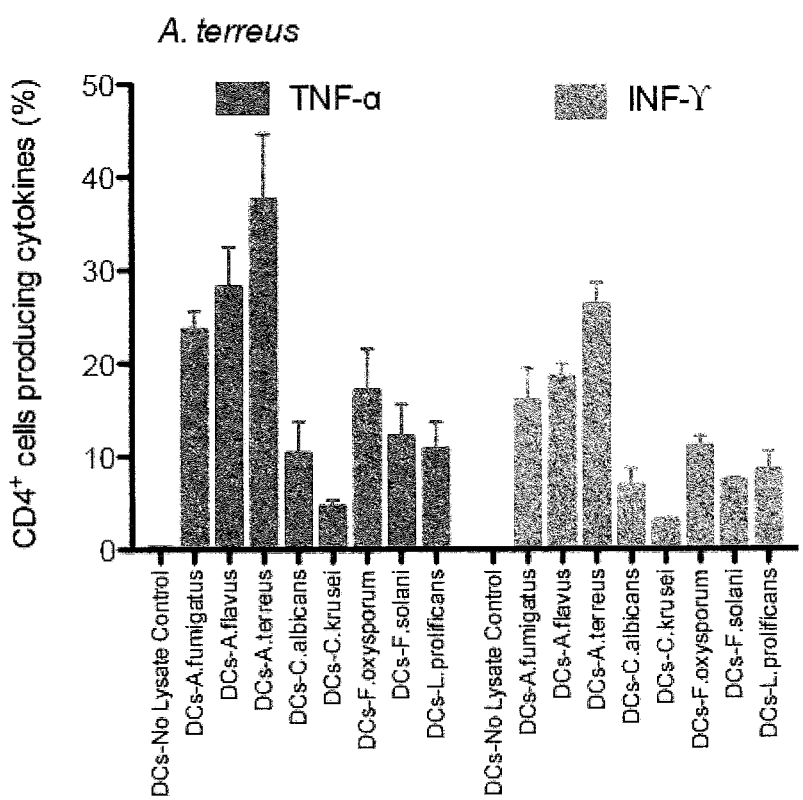
Figure 1:
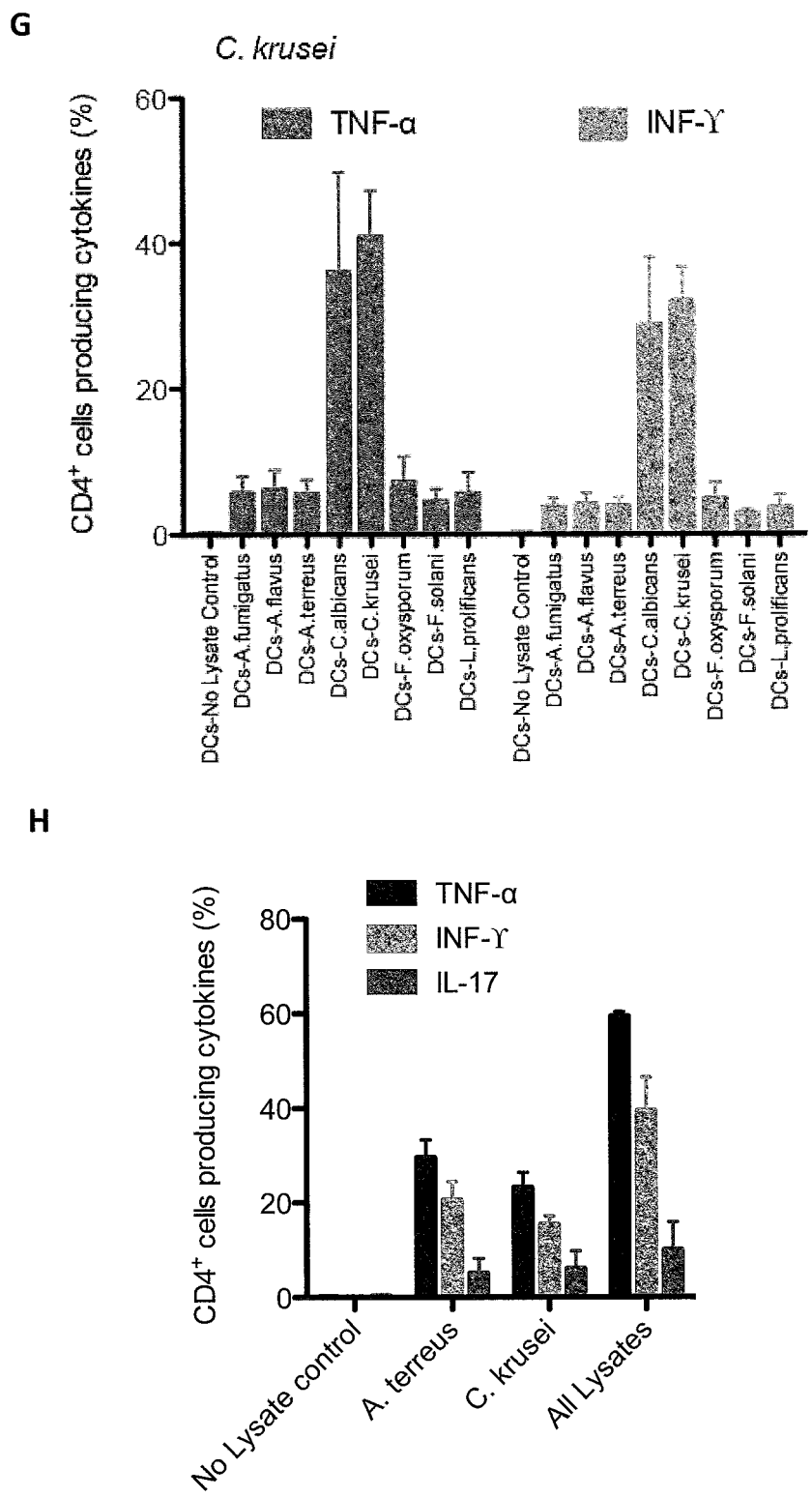
Figure 1:
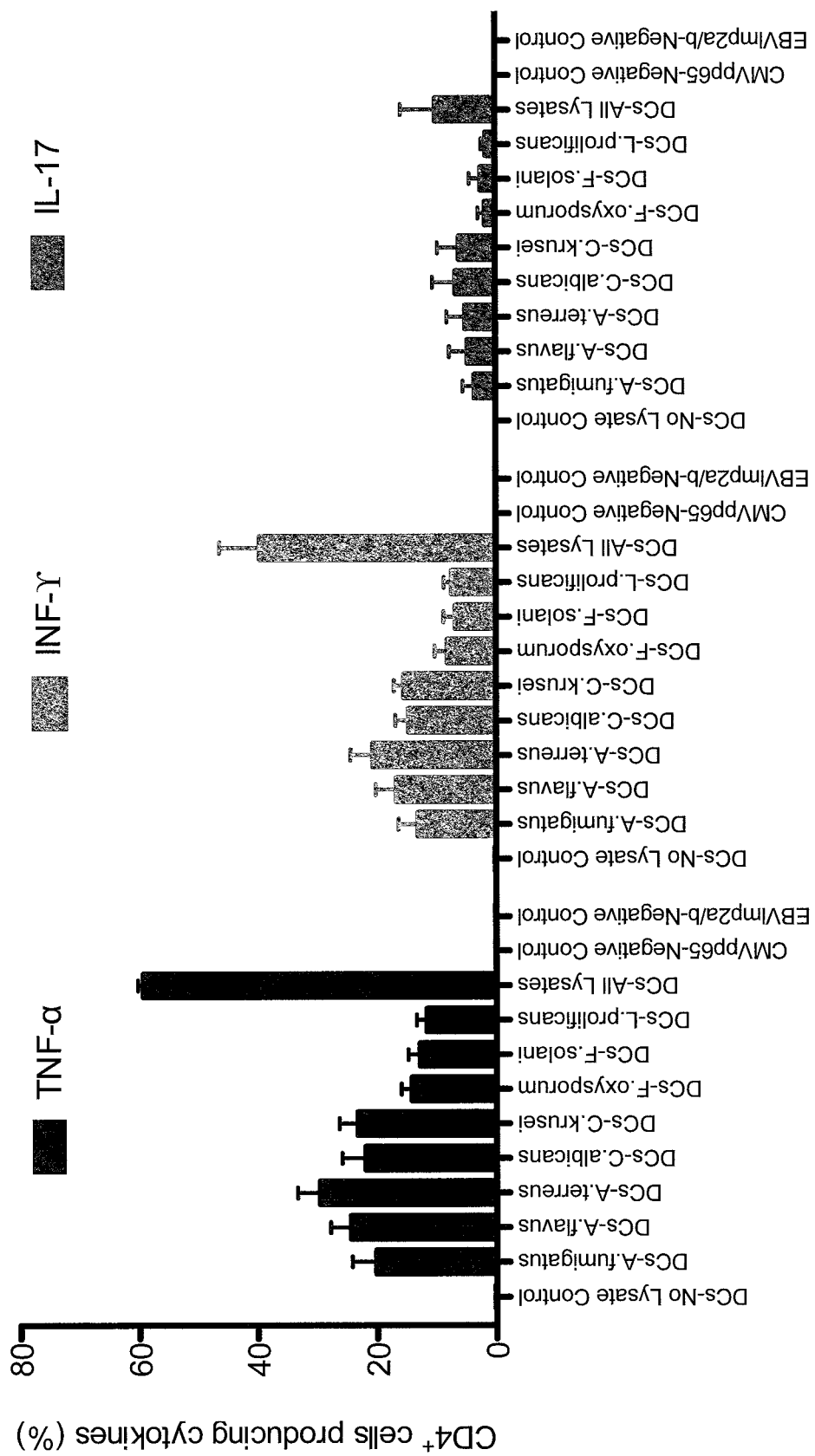

The CD137⁻ cell population was irradiated at 30 Gy and co-cultured with the corresponding CD137-enriched population in complete AIM-V™ medium supplemented with 20 U/mL IL-2, 200 U/mL IL-7 and 200 U/mL IL-15 at 37° C. and 5% $CO_2$. Cytokines were replenished every 2-3 days and half media exchanges were performed as required. All fungal T cell cultures were maintained for a total of 11 to 12 days (FIG. 1A). Individually stimulated T cell cultures generated greater than 96% $CD3^+$ cells (98.6%±0.8), of which greater than 85% (92.9%±2.8) were $CD4^+$ cells and less than 11% (3.2%±3.1) were $CD8^+$ cells. T cell cultures stimulated with multiple fungal lysates generated greater than 85% (97.3%±4.2) $CD3^+$ cells of which greater than 75% (91.7%±5.5) were $CD4^+$ cells and less than 11% (3.6%±3.1%) were $CD8^+$ cells. Results are mean±SD.

The presence of fungus specific T cells was assessed in cultures stimulated with lysates to *A. fumigatus, A. terreus, C. krusei* or *C. krusei* and *A. terreus* by measuring intracellular expression of INFγ, TNFα and/or IL-17 following re-stimulation with the same fungal lysate used to originate the T cell culture (FIGS. 1B-D, H).

Cross-reactivity of cultures stimulated with individual or multiple fungal lysates was also assessed. For individually initiated T cell cultures, the percentages of CD4+ cells that responded to restimulation with other individual lysates by production of TNFα and/or IFNγ is shown in FIG. 1E-G and Table 1. As shown in Table 2 and FIG. 1I, for cultures initiated with multiple fungal lysates the percentages of $CD4^+$ cells that responded to re-stimulation with individual lysates by production of at least one Th1 cytokine (TNFα, IFNγ or IL-17) was variable. TNFα was the predominant Th1 cytokine produced with the percentage of $CD4^+$ cells that expressed intracellular TNFα following stimulation varied from 11.72±1.71% for *L. prolificans* to 29.57±3.75% for *A. terreus*.

TABLE 1

Secretion of TNFα and IFN-γ cytokines from CD4+ T cells from cultures initially stimulated with *A. fumigatus, C. krusei* or *A. terreus*

| CD4+ T cells initially stimulated with: | Re-stimulation | TNF-α MEAN | SEM | n | INF-γ MEAN | SEM | n |
|---|---|---|---|---|---|---|---|
| *A. Fumigatus* | DCs-No Lysate Cnt | 0.30 | 0.06 | 3 | 0.20 | 0.10 | 3 |
| | DCs-*A. fumigatus* | 34.23 | 1.72 | 3 | 19.57 | 2.79 | 3 |
| | DCs-*A. flavus* | 34.93 | 7.08 | 3 | 20.83 | 2.66 | 3 |
| | DCs-*A. terreus* | 34.23 | 3.39 | 3 | 20.07 | 0.35 | 3 |
| | DCs-*C. albicans* | 13.70 | 6.17 | 3 | 7.60 | 3.23 | 3 |
| | DCs-*C. krusei* | 7.07 | 4.09 | 3 | 3.37 | 1.62 | 3 |
| | DCs-*F. oxysporum* | 20.13 | 3.51 | 3 | 11.87 | 1.68 | 3 |
| | DCs-*F. solani* | 14.53 | 3.65 | 3 | 8.20 | 1.01 | 3 |
| | DCs-*L. prolificans* | 17.60 | 4.68 | 3 | 10.63 | 2.24 | 3 |
| *A. terreus* | DCs-No Lysate Cnt | 0.20 | 0.10 | 3 | 0.13 | 0.03 | 3 |
| | DCs-*A. fumigatus* | 23.67 | 1.98 | 3 | 15.93 | 3.51 | 3 |
| | DCs-*A. flavus* | 28.17 | 4.34 | 3 | 18.53 | 1.40 | 3 |
| | DCs-*A. terreus* | 37.53 | 7.09 | 3 | 26.23 | 2.38 | 3 |
| | DCs-*C. albicans* | 10.30 | 3.50 | 3 | 6.87 | 1.84 | 3 |
| | DCs-*C. krusei* | 4.60 | 0.70 | 3 | 3.03 | 0.32 | 3 |
| | DCs-*F. oxysporum* | 17.07 | 4.53 | 3 | 11.03 | 1.13 | 3 |
| | DCs-*F. solani* | 12.13 | 3.45 | 3 | 7.30 | 0.38 | 3 |
| | DCs-*L. prolificans* | 10.73 | 3.00 | 3 | 8.43 | 2.11 | 3 |
| *C. krusei* | DCs-No Lysate Cnt | 0.23 | 0.09 | 3 | 0.20 | 0.15 | 3 |
| | DCs-*A. fumigatus* | 5.67 | 2.29 | 3 | 3.87 | 1.09 | 3 |
| | DCs-*A. flavus* | 6.20 | 2.61 | 3 | 4.13 | 1.57 | 3 |
| | DCs-*A. terreus* | 5.50 | 1.91 | 3 | 4.00 | 1.15 | 3 |
| | DCs-*C. albicans* | 36.10 | 13.61 | 3 | 28.77 | 9.22 | 3 |
| | DCs-*C. krusei* | 40.90 | 6.29 | 3 | 32.03 | 4.68 | 3 |
| | DCs-*F. oxysporum* | 7.17 | 3.46 | 3 | 4.90 | 2.16 | 3 |
| | DCs-*F. solani* | 4.57 | 1.66 | 3 | 2.90 | 0.51 | 3 |
| | DCs-*L. prolificans* | 5.60 | 2.84 | 3 | 3.67 | 1.73 | 3 |

TABLE 2

Secretion of cytokines TNFα, IFNγ, and IL-17 from CD4+ T cells from cultures initially stimulated with *C. krusei* and *A. terreus*

| | CD4+ T cells from *C. krusei* + *A. terreus* culture | | | | | | | | |
|---|---|---|---|---|---|---|---|---|---|
| | TNFα | | | INFγ | | | IL17 | | |
| Re-stimulation | MEAN | SEM | n | MEAN | SEM | n | MEAN | SEM | n |
| DCs-No Lysate Ctl | 0.227 | 0.05 | 6 | 0.23 | 0.09 | 6 | 0.10 | 0.00 | 3 |
| DCs-*A. fumigatus* | 20.17 | 4.04 | 6 | 13.08 | 3.28 | 6 | 3.50 | 2.04 | 3 |
| DCs-*A. flavus* | 24.38 | 3.49 | 6 | 16.72 | 3.50 | 6 | 4.73 | 3.09 | 3 |
| DCs-*A. terreus* | 29.57 | 3.75 | 6 | 20.63 | 3.809 | 6 | 5.10 | 3.13 | 3 |
| DCs-*C. albicans* | 21.93 | 3.97 | 6 | 14.67 | 2.27 | 6 | 6.70 | 3.86 | 3 |
| DCs-*C. krusei* | 23.25 | 3.14 | 6 | 15.45 | 1.71 | 6 | 6.13 | 3.64 | 3 |
| DCs-*F. oxysporum* | 14.20 | 1.76 | 6 | 8.15 | 2.23 | 6 | 1.73 | 1.19 | 3 |
| DCs-*F. solani* | 12.85 | 1.96 | 6 | 6.80 | 2.03 | 6 | 2.47 | 1.92 | 3 |
| DCs-*L. prolificans* | 11.72 | 1.71 | 6 | 7.45 | 1.31 | 6 | 1.60 | 0.78 | 3 |
| DCs-All Lysates | 59.37 | 0.94 | 3 | 39.60 | 6.90 | 3 | 10.07 | 5.85 | 3 |
| CMVpp65-Neg Ctl | 0.17 | 0.09 | 3 | 0.13 | 0.07 | 3 | 0.03 | 0.03 | 3 |
| EBVlmp2a/b-Neg Ctl | 0.13 | 0.07 | 3 | 0.13 | 0.09 | 3 | 0.00 | 0.00 | 3 |

Example 3—Generation of Multipathogen T Cell Cultures

Generation of Multipathogen T Cell Cultures in a Single Culture

T cell cultures were established from platelet-reduced HPCs using synthetic peptide mixes of CMV, EBV, AdV (1 µg/mL per peptide) and a water soluble lysate of *A. fumigatus* (10 µg/mL) for antigenic stimulation. CD137$^+$ cells were isolated using immunomagnetic enrichment and culture expanded as described above.

At the completion of the culture period, the predominant cell type observed was CD3$^+$ T cells (mean 99±0.6%). Pathogen specific T cells were measured as described above and T cells producing TNFα in response to antigenic stimulation was observed in all cultures but dominated by CMV (33.4±13.4%) and EBV (33.3±37.4%) (FIG. 2A). Comparatively, the mean percentage of T cells producing TNFα in response to adenoviral or *A. fumigatus* antigens was 2.4±3.5% and 0.9±1.1% respectively (FIG. 2A). The proportion of responding cells that were specific for either CMV or EBV exceeded 88% in all cultures (mean 95.7±3.2%; FIG. 2B). T cells producing IFNγ in response to antigenic stimulation was also dominated by CMV compared to AdV and *A. fumigatus* (FIG. 2C).

The dominance of CMV and EBV in the T cell culture is likely to reflect a higher frequency in the starting population compared to AdV and *A. fumigatus* specific T cells and/or a competitive advantage during cell expansion in culture.

Generation of Multipathogen T Cell Cultures in Separate Cultures

To increase the antigen specificity of cultures, T cell cultures were generated by stimulation with a single antigen (synthetic peptides of CMV, EBV, AdV (1 µg/mL per peptide) or a water soluble lysate of *A. fumigatus* (40 µg/mL)) as described above. A total of twenty-seven individual T cell cultures were generated (CMV n=8; EBV n=5; AdV n=7 and *A. fumigatus* n=7), CD137$^+$ immunoselected and culture expanded.

Significant differences in the capacity of cultured T cells to proliferate in response to stimulation with individual peptides/lysate were observed in multipathogen cultures compared to T cells of individual cultures (FIG. 3A).

The specificity of the individual T cell products was assessed by determining TNFα production in response to antigenic stimulation. The predominant cell type was CD3$^+$ T cells in all cultures (mean 98.6±1.4%). The mean percentage of T cells producing TNFα in response to CMV and EBV was 62.7±17.7% and 73±20.1% respectively. When stimulated separately, the proportion of T cells with AdV specificity was higher (59.3±16.4%) compared to responses when pooled with other pathogens (2.4±3.5%). Similarly, 38.4±23.1% of T cells produced TNF in response to an *A. fumigatus* lysate when prepared separately compared to 0.9±1.1% when prepared in a pooled culture (FIG. 3B). The proportion of responding cells (% of the highest of TNFα+ cells from CD4 population, INFγ+ cells from CD8 population or CD107a/b+ cells from CD8 population) that were specific for individual viral or fungal antigens was higher in the individual T cell cultures compared to the multipathogen (FIG. 3C).

Example 4—Generation of Tumour Antigen T Cell Cultures

Cultures from G-CSF mobilized peripheral blood stem cell harvests were prepared as described above. Platelet-reduced HPCs were incubated with 1 µg/ml WT1 Peptivator and 1 µg/ml CliniMACS® anti-CD28 pure AB reagent in complete AIM-V™ medium supplemented with 10% heat-inactivated auto-plasma for 16-18 hours at 37° C. and 5% $CO_2$. Following incubation, the cells were CD137 immunoselected and culture expanded as described above (FIG. 4A).

WT1 specificity was measured by CD107 expression after re-stimulation with WT1 peptide mixture (WT1 mean 14.6%±7.3; control mean 1.5%±0.3; FIG. 4B). The proportion of IFN-γ CD8 T cells specific for WT1 was also determined (FIG. 4C).

Example 5—Preparation of T Cell Product of Defined Composition

Based on Total Cell Number

T cell products prepared from single T cell pathogen products pooled in defined ratios were prepared and compared to T cell products prepared from multipathogen T cell cultures.

Individual T cell products were prepared using CMV, EBV, AdV or *A. fumigatus* alone or a combination of CMV, EBV, AdV and *A. fumigatus* as antigenic stimulation as previously described. Following stimulation cells were CD137 immunoselected and culture expanded as described above.

Based on the results described above, if the CMV, EBV, AdV and Asp T cell cultures were pooled in equal numbers (eg, $1 \times 10^7$ cells/pathogen) at the completion of the culture, the proportion of responding T cells would be more evenly distributed against the four pathogens (CMV 27-28%, EBV 31%, AdV 25% and Asp 16%) when compared with the multipathogen T cell culture where CMV and EBV were dominant. This is illustrated by the upper two pie charts in FIG. 5 which may be compared to FIG. 3B (single pathogen pooled) and FIG. 2A (multipathogen). Indeed, a more even distribution was observed when T cell cultures single pathogen pooled and multipathogen T cell cultures were prepared from two donors. T cell products were generated with a total of ~$2 \times 10^7/m^2$ (~$4 \times 10^7$ total nucleated cells). Cells from individual CMV, EBV, AdV and *A. fumigatus* T cell cultures were pooled in equal numbers (i.e., $1 \times 10^7$ cells/pathogen) at the completion of the culture period.

For donor 1, the multipathogen T cell culture was dominated by EBV (67%) and CMV (21%) specific responses, with 9% responding to AdV and 3% to Asp. For this donor, when single pathogen cultures were combined equally, the proportion of responding T cells was distributed more evenly in respect of each pathogen (CMV 26%, EBV 28%, AdV 25%, Asp 21%; FIG. 5). Similarly, for donor 2, 89% of responding T cells in the multipathogen T cell culture were specific for CMV, whereas when single pathogen cultures were combined with equal numbers, the proportion of responding T cells specific for CMV, EBV, AdV and Asp was more evenly distributed (CMV 32%, EBV 36%, AdV 25%, Asp 7%); FIG. 5).

Based on Clinical Situation

A T cell product is prepared, using methods described above, based on the likelihood of severe infection associated with demographics and the type of transplant and is constituted based on combining equal or varying numbers of cells from the individual pathogen and/or malignant directed cell cultures based on a specific number of:
a) total nucleated cells from individual cell culture; or
b) CD3$^+$ cells or CD4$^+$ cells or CD8$^+$ cells from individual cell cultures; or c) activation marker positive cells following re-stimulation from individual cell cultures: or d) cytokine producing cells following re-stimulation from individual cell cultures.

Based on Underlying Malignancy Diagnosis

A T cell product is prepared, using methods described above, based on the underlying malignancy diagnosis. A defined composition is prepared containing a varying (1-99%) proportion of cells from a culture known to contain T cells specific for the malignant cells relevant to the patient's diagnosis (e.g., acute myeloid leukemia, acute lymphoblastic leukemia, multiple myeloma or lymphoma) in combination with one or more infectious pathogen directed cells.

A patient receiving a blood stem cell transplant for acute myeloid leukemia is selected for treatment with T cell compositions reactive to both tumour and viral antigens. A T cell product is prepared from single T cell cultures specific to viral and/or fungal antigens CMV, EBV, AdV and VZV and multiple fungi and the tumour antigen WT1, as described above. Following transplant, the patient receives the T cell product to treat and prevent infection.

Based on Serology or Infectious Status of the Patient and/or Donor

A defined T cell product is prepared, using methods described above, based on the serology or infectious status of the patient and/or donor.

Following a seropositive status and/or virus nucleic acid test positive and/or galactomannan test and/or positive culture and/or other diagnostic clinical test for a pathogen (e.g., CMV, EBV, HHV6, VZV or fungal infection), a T cell product is prepared by varying the number of T cells based on the presence or likely presence of that pathogen.

In addition, if one or more pathogens are frequently identified in association with the first pathogen, T cells with specificity to those one or more pathogens may also be included in the composition.

Based on the Patient's Previous Infectious History

A defined T cell product is prepared, using the methods described above, based on a patient's history of infections. Cultures are established by exposure to pathogens to which the patient is known to have suffered an infection pre-transplant (e.g., a fungal infection or a viral infection, such as CMV, EBV, HSV, VZV, RSV, influenza or tuberculosis).

Based on Known Profiles of Infection in Groups of Transplant Patients

A defined T cell product is prepared, using the methods described above, based on a known profile of infection taking into consideration demographic parameters such as age and transplant type.

A composition for a paediatric transplantation patient is prepared using the methods described above and comprises T cells reactive to AdV.

A composition for a cord transplant recipient is prepared using methods described above and comprises T cells reactive to HHV6.

Example 6—Generation and Further Characterisation of Fungus-Specific T Cell Cultures Phenotypic Analysis T cell cultures were established from platelet-reduced HPCs and water soluble lysate of *A. terreus* and *C. krusei* for antigenic stimulation. CD137$^+$ cells were isolated using immunomagnetic enrichment and culture expanded as described above. Cells were stained with monoclonal antibodies to antigens of interest and analysed by flow cytometry.

At completion of the culture period, cells were predominantly CD4$^+$ T cells (FIG. 6A, 6B). The majority of the CD4$^+$ cells displayed an effector memory phenotype with smaller populations of central memory, terminal effector and naïve phenotype (FIG. 6D). The cells also expressed the inhibitory receptors Lag-3, Tim-3 and PD-1 (FIG. 6C).

Analysis of chemokine receptor expression also demonstrated that the majority of the CD4$^+$ cells had a Th1 type pattern, followed by Th9, Th2 and Th1/Th17 pattern, with a smaller percentage of Th22 and Th17 cells (FIG. 7).

Cytokine Profile

Supernatants of fungus-specific T cells cultured for 24 hours with non-pulsed (control) or fungus pulsed (activated) DCs were blotted onto membranes and probed with antibodies to cytokines. Detectable secondary antibodies were then layered and colour developed. The density of dots was read and a relative density measurement calculated for each cytokine by forming a ratio of density from fungus-pulsed DC stimulated cultures with density from non-pulsed DC stimulated cultures. A marked increase in the release of IL-2, GM-CSF, IL-10, IL4, IL-4, IL-5 and TNF was observed as a result of presentation of fungal antigens to cultured T cells by DCs (FIG. 8).

Cytokine expression was also analysed in T cells cultured for 5 hours with non-pulsed DCs or fungus-pulsed DCs. An increase in the proportion of CD4+ cells expressing interferon-gamma, GM-CSF, IL-2, IL-4, TNF-α, IL-13 and IL-17 was observed following fungal antigen presentation by DCs to fungus-specific T cells (FIG. 9). Together, these results show that fungus-specific T cells mediate a pro-inflammatory/antifungal response when exposed to fungi.

T cells that had been cultured for 5 hours with non-pulsed DCs or fungus lysate pulsed DCs were stained with a panel of monoclonal antibodies labelled with heavy metal ion tags and analysed by time-of-flight mass spectrometry. t-distribution stochastic neighborhood embedding (t-SNE) analyses indicated which cells in the landscape of antigen expression were producing GM-CSF, TNF-α and IFN-γ upon exposure to the fungal antigens. The highest expression of the three cytokines was observed in two subpopulations of CD4+ cells (FIG. 10). Responding fungus-specific T cells correspond to the cell cluster showing higher GM-CSF, IFN and TNF expression, indicative of a majority cells with similar phenotype.

Anti-Hyphal Activity

An XTT assay was performed to assess the anti-hyphal activity of cultured fungus-specific T cells stimulated with *A. terreus* and *C. krusei*. Conidia from *A. fumigatus* was incubated for 2 hours with fungus-specific T cells alone, peripheral blood white blood cells (WBC) that had not previously been cultured with fungi, and a combination of the two.

Some damage to fungal hyphae was observed using fungus-specific T cells alone and using white blood cells alone, but when used together, the level of hyphal damage was greater than either (FIG. 11). These results indicate that fungus-specific T cells are able to kill fungi directly and augment the fungus-killing ability of unprimed white blood cells, including innate effectors such as monocytes or neutrophils.

HLA DR Analysis

T cell cultures were exposed to *A. terreus* and *C. krusei* lysate, enriched for CD137 and in vitro expanded as described above. The fungus-specific T cells were incubated with DCs pulsed with fungal lysate and antibodies to various MHC proteins. After a period of incubation, CD4+ fungus-specific T cells were analysed for expression of TNF-α. Recognition of fungal antigens by CD4+ fungus-specific T cells was largely mediated by HLA DR (FIG. 12A). CD4+ fungus-specific T cells could recognise fungal antigens even when only one of the two HLA DR antigens was matched between the DC and CD4+ fungus-specific T cells (FIG. 12B). CD4+ fungus-specific T cells generated using cells from the most common HLA types (DRB1 01:01, 04:01, 11:01, 13:01 or 15:01) could still recognise fungal antigens presented by HLA DR subtypes that were allelic mismatches (HLA DRB1 01:02; 04:03, 04:04, 04:05; 11:04; 13:02; 15:02) indicating that a bank of fungus-specific T cells made using the most common HLA DR types may be valuable in treating patients with less common HLA DR allelic subtypes who have invasive fungal infection (FIG. 12C-G).

Intracellular flow cytometry was conducted to assess TNF-α production in fungus-specific T cells stimulated with HLA DR homozygous B cell lymphoblastoid cell lines (B-LCL). The B-LCL effectively presented fungal antigens to CD4+ T cells, highlighting a novel method for determining the HLA DR element of restriction of fungus-specific T cells (FIG. 13). Stimulation can be carried out with HLA DR homozygous B-LCL expressing one of the HLA DR molecules of the fungus-reactive cells. For example, if a fungus-reactive product is generated from a donor who is HLA DR 01:01 and 07:01, the product may be stimulated with B-LCL homozygous for HLA DR 01:01 and with B-LCL homozygous for HLA DR 07:01 to determine which one of the HLA DRs is restricting the activity (or to determine the relative contribution of each HLA DR). This approach may be used for other CD4+ dominated compositions, eg, adenovirus- and HHV6-specific T cell compositions.

TCR Analysis

T cell cultures were established from platelet-reduced HPCs and water soluble lysate of *Aspergillus fumigatus* for antigenic stimulation. CD137+ cells were isolated using immunomagnetic enrichment and culture expanded as described above.

Fungus-specific T cell products were subjected to PCR amplification of TCR-β, followed by sequencing and read frequency determination. A relatively small number of TCR clones made up the top 25% of TCR sequences (FIG. 14).

Example 7—Treatment Using a Composition Comprising T Cells

A 26 year old female patient displayed acute myeloid leukaemia secondary to chemotherapy for stage 4 large B cell lymphoma. Lymphoma was diagnosed at age 22 with bulky mediastinal mass, pericardial involvement with tamponade and SVC obstruction as well as disease in multiple areas above and below the diaphragm. The patient had been treated with 6 cycles of R-CHOP chemotherapy and 4 doses of intrathecal MTX with complete response. Lymphoma has remained in remission.

A diagnosis of trisomy 21 was made within 2 years following chemotherapy for lymphoma. The patient was treated with arabinoside and idarubicin chemotherapy but experienced complications of neutropenic infection and perianal infection.

A matched, allogenic stem cell transplant with myeloablative conditioning was performed in January 2018. The patient experienced early toxicity and was admitted to intensive care with hypoxic respiratory failure. The recipient and donor were CMV seronegative but EBV seropositive. qPCR also demonstrated that the patient expressed WT1.

Based on the low risk of CMV due to donor and recipient seronegativity, and the higher risk of EBV infection and invasive fungal infection post-transplant, a cell product directed against EBV and *Aspergillus*, and a separate cell product directed against WT1 was also generated.

The EBV and *Aspergillus* cell product was prepared using two separate cell cultures. $5 \times 10^7$ donor mononuclear cells were stimulated with an EBV consensus peptide pool and an *Aspergillus fumigatus* water soluble lysate. After 11 days of culture, EBV and *Aspergillus* cultures were enumerated and pooled to create a single multi-pathogen composition comprising $2 \times 10^7/m^2$ EBV-specific T cells and $2 \times 10^7/m^2$ *Aspergillus*-specific T cells (57% CD8, 42% CD4 with 86% of CD8 specific for EBV and 30.9% of CD4 specific for *Aspergillus*).

The WT1 cell product was prepared by stimulating $1 \times 10^8$ mononuclear cells with a WT1 overlapping peptide mix. Following an 18 hour incubation, activated antigen-specific T cells were isolated by magnetic selection of CD137-expressing T cells and expanded separately by co-culture with irradiated autologous feeder cells in media supplemented with IL-2, IL-7 and IL-15. WT1-specific T cells were cultured for 20 days and cryopreserved in four separate bags containing $4 \times 10^7/m^2$ WT1-specific T cells.

On day 35 post-transplant, the patient was infused with the composition comprising EBV- and *Aspergillus*-specific T cells at a dose of $1 \times 10^7/m^2$ EBV-specific T cells and $1 \times 10^7/m^2$ *Aspergillus*-specific T cells. The patient also received on day 35 post-transplant an infusion of the composition comprising WT1-specific T cells. An infusion of $2 \times 10^7/m^2$ WT1-specific T cells was performed on day 35 post-transplant with 3 additional infusions of the same dose being delivered 4 weeks apart (WT1-specific T cells were administered every four weeks after the first infusion). No infusion-related toxicities and no infectious complications were identified post-infusion. No graft versus host disease was detected. The patient remains well as an outpatient in morphological remission of her AML 4.5 months after transplant.

Example 8—Treatment of Disseminated Fungal Infection with Fungus-Specific T Cells Medical Background A 51 year old male was diagnosed with Hodgkin's lymphoma at age 27 and was treated with 6 cycles of adriamycin, bleomycin, vinblastine, dacarbazine (ABVD)/nitrogen mustard, vincristine, procarbazine, prednisone (MOPP) chemotherapy and radiation to the mediastinum. Hodgkin's disease was cured, but twenty years later the patient developed bilateral pleural effusions of unclear aetiology requiring pleurodesis. The patient suffered from chronic hepatitis B and received long term entecavir.

The patient was diagnosed with Waldenstrom's macroglobulinemia in 2006 after finding elevated levels of IgM. The patient was initially treated with chlorambucil and prednisone (4 cycles).

In 2008, the patient was administered rituximab plus cyclophosphamide, vincristine and prednisone (4 cycles+2 further cycles of rituximab).

In 2013, recurrence of Waldenstrom's macroglobulinemia was observed with pleural effusions. Single agent rituximab was recommenced with little effect.

In 2014, the patient was treated for immune-mediated thrombocytopenia with danazol. The patient was treated with rituximab plus bendamustine and idelalisib (2 cycles), but treatment was complicated by severe shingles, and hemolysis related to bendamustine. Bendamustine was ceased and rituximab was continued plus idelalisib maintenance.

In 2014, the patient developed neck swelling due to *Scedosporium boydii* infection in neck soft tissue. The patient was treated for three months with voriconazole, idelalisib was ceased for 10 months and recommenced in October 2015 in the setting of rising IgM.

In 2016, cerebral *Scedosporium* infection developed, and idelalisib was permanently ceased. Neck mass encasing vertebral arteries was biopsied, and biopsy showed lymphoplasmacytic lymphoma.

In 2017, the patient's left paravertebral deposit was treated with radiation therapy. BGB-3111 (zanubrutinib) was commenced as part of a clinical trial. The patient developed left fungal endophthalmitis and was treated with high dose voriconazole. Knee effusion was surgically washed out, and pan fungal PCR on a specimen from the effusion was positive for *Scedosporium*.

Prolonged admission in late 2017-2018 with disseminated *Scedosporium* infection and progression despite triple antifungal therapy (terbinafine, miltefosine and voriconazole). Issues during admission included multiple brain abscesses, left pleural effusion and possibly empyema, subcutaneous nodules which were biopsied and were positive for *Scedosporium*, prostate abscess (seen on CT), painful paravertebral abscesses drained and grew *Scedosporium* but recurred despite triple therapy, right knee effusion drained grew *Scedosporium* despite 4 weeks of triple therapy, pericardial effusion, development of multiple ring enhancing lesions within the supratentorial and infratentorial compartments favoured to reflect multiple intracranial abscesses.

Anti-Fungal T Cell Therapy

*Aspergillus fumigatus* lysate-stimulated T cells were generated from the patient's fully matched HLA, A, B, C, DR B1 healthy identical male sibling. The inventors had previously demonstrated that *Aspergillus fumigatus* lysate-stimulated T cells are reactive against *Scedosporium*.

Cells were produced by overnight incubation of donor mononuclear cells with *Aspergillus fumigatus* lysate, selection of CD137 expressing cells using antibody and magnetic bead isolation, and 12 day culture in medium supplemented with cytokines IL-2, IL-7 and IL-15. Following completion of the culture and quality testing, the cells were cryopreserved according to standard laboratory practice. Cells at the end of the culture had the following characteristics: CD3+ 97%, CD4+ 91.1%, CD8+ 7.8%, NK cells 0.4%, monocytes 0%, B cells 0%. Upon stimulation with *Aspergillus* lysate in vitro, cultured cells had the following characteristics by surface (CD107) and intracellular (interferon-$\gamma$, tumour necrosis factor-$\alpha$) flow cytometry:

CD3+: 7.7% CD107+, 24.6% interferon-$\gamma$+, 38.7% tumour necrosis factor-$\alpha$+;

CD8+: 7.3% CD107+, 11.3% interferon-$\gamma$+, 15.4% tumour necrosis factor-$\alpha$+; and CD4+: 11.5% CD107+, 26.3% interferon-$\gamma$+, 38.7% tumour necrosis factor-$\alpha$+.

$1\times10^6/m^2$ *Aspergillus*-specific T cells were infused to the patient without prior conditioning. Peripheral blood mononuclear cells were taken pre-infusion and at various times after infusion from day +1 to day +28 post-infusion. Cells were stained with antibodies complexed to heavy metal ions prior to analysis by mass cytometry time of flight (mass CyTOF). Cells were briefly incubated with monensin prior to staining, but were not restimulated in vitro. No acute infusion related toxicities were observed.

Absolute lymphocyte count of $0.3\times10^9$/L at the time of T cell infusion subsequently peaked at $1.0\times10^9$/L 15 days after infusion. Absolute monocyte count of $0.4\times10^9$/L subsequently peaked at $1.8\times10^9$/L 22 days after infusion.

Absolute lymphocyte counts in the patient's peripheral blood were pre-infusion 0.3, day +1 0.3, day 3 0.6, day 5 0.3, day 7 0.8, day 13 0.6, day 22 1.0 and day 28 $0.3\times10^9$/L (FIG. 15A). An increased percentage of CD3+ cells was detected in the patient from day +1 to +7 after T cell infusion, though remaining below control values (FIG. 15A). An increased percentage of CD4+ cells and CD8+ cells expressing the inhibitory marker Tim3 was observed from day +7 to day +22 post-infusion (FIG. 15B). An increased percentage of CD3+ and CD3− cells producing GM-CSF, IL-10 and IL-4 was observed between days +1 and +5 post-infusion (FIG. 15C). A marked increase in the percentage of CD14+CD16+ inflammatory monocytes was also observed commencing at day +5 post-infusion, peaking at day +7 and resolved by day +13 (FIG. 15D).

Example 9—Cryopreservation "Banking" of T Cells

Following T lymphocyte harvest, T cells are cryopreserved for adoptive T cell transfer.

A freezing mix containing 40% saline, 40% Albumex20 and 20% DMSO is prepared. The saline is added to the DMSO and chilled before adding the Albumex20. The freezing mix is kept chilled until required.

The cells for cryopreservation are resuspended, pooled and mixed thoroughly. The cells are counted using a haemocytometer and the cell concentration and total cell viability is determined.

The cells are spun at 1400 rpm for 5 mins and 5 mls of the supernatant is removed for *Mycoplasma* testing. The remaining supernatant is discarded.

The cells are washed with up to 50 ml of 0.9% saline supplemented with Albumex20 and spun at 1400 rpm for 5 mins.

The cells are resuspended in 0.9% saline at a concentration of $2\times10^7$ cells/mL.

For the cryopreservation of T cells, the maximum volume of cells to be added per bad is to be calculated using the formula:

$$\text{Maximum volume per bag (mL)} = \text{Max number of cells required per bag}/1\times10^7 \text{ per ml}$$

The number of bags and quality assurance samples to be cryopreserved is determined, noting that three pilot vials containing 200 µl of T lymphocyte suspension must be stored for post thaw analysis and endotoxin testing; 200 µl of T lymphocyte suspension is to be submitted for *Mycoplasma* testing; three 1 mL aliquots of T lymphocyte suspension must be stored for quality control testing of the product; and any excess that does not equal a complete dose can be stored in additional aliquots.

An equal volume of freezing mix is added to the T lymphocyte suspension and mixed. The required volume of cells is transferred into cryopreservation bags and/or vials. The bags and vials are immediately placed into pre-cooled rate controlled freezers to begin cryopreservation.

Example 10—Adoptive Transfer of T Lymphocyte Products

The T cell products are used in adoptive transfer provided they meet the following release criteria:
Greater than 50% post thaw viability;
Less than 2% B cells (CD19$^+$) and monocytes (CD14$^+$);
Negative for bacterial and fungal contamination;
Negative for *Mycoplasma* contamination and endotoxin;
No evidence of alloreactivity defined as <10% specific cytotoxicity against recipient derived PHA blasts at a ratio of 20:1 T cells to target cells in a standard $^{51}$CR assay.

The invention claimed is:

1. A composition comprising at least two populations of T cells, wherein each population has been separately contacted with at least one antigen from a different fungus, virus or tumor, wherein each population comprises T cells reactive with the at least one antigen from the different fungus, virus or tumor, wherein the composition comprises a defined number or defined ratio of T cells from each population, and wherein the defined number or defined ratio is based on a subject's clinical diagnosis, a subject's serology or infectious status, a subject's previous serology or infectious status, or a known antigen profile for a tumor or infection.

2. The composition of claim 1, wherein the defined number or defined ratio of T cells from each population is further based on at least one of the following:
   a) the total number of nucleated cells;
   b) the percentage of CD3+, CD4+ or CD8+ cells reactive with the at least one antigen from the different fungus, virus or tumor;
   c) the percentage of each population expressing CD4+; and
   d) the percentage of each population expressing CD8+.

3. The composition of claim 1, wherein each population is combined in a ratio of between 1:1 and 1:99.

4. The composition of claim 1, wherein the composition comprises a total of between about 1×10$^7$ cells/m$^2$ and about 10×10$^7$ cells/m$^2$.

5. The composition of claim 1, comprising:
   a) T cells reactive with fungal antigens only; or
   b) T cells reactive with viral antigens only; or
   c) T cells reactive with tumor antigens only; or
   d) one or more population(s) of T cells each population reactive with a fungal antigen and one or more population(s) of T cells each population reactive with a viral antigen; or
   e) one or more population(s) of T cells each population reactive with a fungal antigen and one or more population(s) of T cells each population reactive with a tumor antigen; or
   f) one or more population(s) of T cells each population reactive with a viral antigen and one or more population(s) of T cells each population reactive with a tumor antigen; or
   g) one or more population(s) of T cells each population reactive with a fungal antigen, one or more population(s) of T cells each population reactive with a viral antigen and one or more population(s) of T cells each population reactive with a tumor antigen.

6. The composition of claim 1, comprising:
   (a) a population of T cells reactive with cytomegalovirus and a population of T cells reactive with Epstein-Barr virus; or
   (b) a population of T cells reactive with cytomegalovirus and a population of T cells reactive with Epstein-Barr virus and a population of T cells reactive with BK virus; or
   (c) a population of T cells reactive with an extract of *Candida krusei* and a population of T cells reactive with an extract of *Aspergillus terreus*; or
   (d) a population of T cells reactive with an extract of *Candida krusei* and a population of T cells reactive with an extract of *Aspergillus terreus* and a population of T cells reactive with BK virus and a population of T cells reactive with adenovirus; or
   (e) a population of T cells reactive with an extract of *Candida krusei* and a population of T cells reactive with an extract of *Aspergillus terreus* and a population of T cells reactive with cytomegalovirus and a population of T cells reactive with Epstein Barr virus; or
   (f) a population of T cells reactive with Wilms tumor 1 (WT-1) and a population of T cells reactive with preferentially expressed antigen in melanoma (PRAME); or
   (g) a population of T cells reactive with cytomegalovirus and a population of T cells reactive with Epstein-Barr virus and a population of T cells reactive with WT-1 and a population of T cells reactive with PRAME; or
   (h) a population of T cells reactive with cytomegalovirus and a population of T cells reactive with Epstein-Barr virus and a population of T cells reactive with an extract of *Aspergillus terreus* and a population of T cells reactive with an extract of *Candida krusei* and population of T cells reactive with WT-1 and a population of T cells reactive with PRAME.

7. The composition of claim 6, wherein the populations of T cells are combined at a ratio of about 1:1 to about 1:3.

8. The composition of claim 6, wherein the composition of (c) additionally comprises a population of T cells reactive with WT-1.

9. The composition of claim 1, wherein upon administration to a subject the composition confers a therapeutic or protective immune response.

10. The composition of claim 1, wherein one of the at least two populations of T cells is enriched for CD137 expressing cells.

11. A method for producing the composition of claim 1, comprising:
   a) separately contacting each of at least two populations of cells comprising T cells with at least one antigen from a different fungus, virus or tumor;
   b) isolating the populations comprising T cells following the contacting; and
   c) combining the populations of T cells in a defined ratio or defined number,
   wherein the defined number or defined ratio is based on a subject's clinical diagnosis, a subject's serology or infectious status, a subject's previous serology or infectious status, or a known antigen profile for a tumor or infection.

12. The method of claim 11, comprising enriching at least one of the populations of calls comprising T cells for CD137 expressing cells.

13. The method of claim 11, comprising expanding the populations of cells comprising T cells in vitro prior to combining.

14. The method of claim 11, wherein the antigen from the fungus is comprised in a water soluble lysate.

15. The method of claim 11, wherein the antigen from the virus is a viral protein, or a peptide or peptides from a viral protein, or is within a lysate of a virus infected cell, or is expressed by a cell modified to express the antigen.

16. The method of claim 11, wherein the antigen from the tumor is a tumor protein, or a peptide or peptides from a tumor protein, or is expressed by a cell modified to express the tumor antigen.

17. A method of treating a subject in need thereof, the method comprising administering the composition of claim 1 to the subject and inducing a therapeutic or protective immune response in the subject.

18. The method of claim 17, wherein the subject is undergoing or is about to commence or has completed chemotherapy and/or hematopoietic stem cell transplantation and/or solid organ transplantation and/or immunoablation therapy and/or has an inherited familial or congenital immunodeficiency, syndrome and/or has an acquired immunodeficiency syndrome and/or is receiving or has received immunosuppressive therapy for an immune mediated disease.

19. The method of claim 17, additionally comprising matching at least one HLA antigen in the T cells to at least one HLA antigen in the subject.

20. The method of claim 17, wherein the T cells are non-autologous to the subject.

21. The composition of claim 1, wherein the composition comprises T cells reactive with all or almost all antigens used in said contacting.

22. The composition of claim 1, wherein, following said contacting, each population has been separately cultured for less than 21 days and then combined to form the composition.

* * * * *